(12) United States Patent
Imamura et al.

(10) Patent No.: US 7,408,017 B2
(45) Date of Patent: Aug. 5, 2008

(54) POLYHYDROXYALKANOATE CONTAINING UNIT WITH PHENYLSULFANYL STRUCTURE IN THE SIDE CHAIN, PROCESS FOR ITS PRODUCTION, CHARGE CONTROL AGENT, TONER BINDER AND TONER WHICH CONTAIN NOVEL POLYHYDROXYALKANOATE, AND IMAGE FORMING METHOD AND IMAGE-FORMING APPARATUS WHICH MAKE USE OF THE TONER

(75) Inventors: Takeshi Imamura, Kanagawa (JP); Etsuko Sugawa, Kanagawa (JP); Tetsuya Yano, Kanagawa (JP); Tsuyoshi Nomoto, Tokyo (JP); Tomohiro Suzuki, Kanagawa (JP); Tsutomu Honma, Kanagawa (JP); Takashi Kenmoku, Kanagawa (JP); Tatsuki Fukui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 362 days.

(21) Appl. No.: 11/155,599

(22) Filed: Jun. 20, 2005

(65) Prior Publication Data
US 2005/0250191 A1 Nov. 10, 2005

Related U.S. Application Data

(62) Division of application No. 10/084,172, filed on Feb. 28, 2002, now Pat. No. 7,045,321.

(30) Foreign Application Priority Data

| Mar. 1, 2001 | (JP) | ............................... 2001-057142 |
| Mar. 1, 2001 | (JP) | ............................... 2001-057145 |
| May 31, 2001 | (JP) | ............................... 2001-164774 |
| Jul. 10, 2001 | (JP) | ............................... 2001-210037 |
| Jul. 10, 2001 | (JP) | ............................... 2001-210049 |
| Feb. 15, 2002 | (JP) | ............................... 2002-039254 |

(51) Int. Cl.
*C08G 63/688* (2006.01)
(52) U.S. Cl. .................................................... 528/295
(58) Field of Classification Search ................. 528/271, 528/295
See application file for complete search history.

(56) References Cited

U.S. PATENT DOCUMENTS

| 4,393,167 | A | 7/1983 | Holmes et al. ................. 525/64 |
| 4,442,189 | A | 4/1984 | Lu et al. ....................... 430/45 |
| 4,480,021 | A | 10/1984 | Lu et al. .................... 430/106.6 |
| 4,795,690 | A | 1/1989 | Shindo et al. ................ 430/109 |
| 4,876,331 | A | 10/1989 | Doi ............................. 528/361 |
| 4,925,765 | A | 5/1990 | Madeleine ................... 430/110 |
| 5,004,664 | A | 4/1991 | Fuller et al. .............. 430/106.6 |
| 5,135,859 | A | 8/1992 | Witholt et al. ............... 435/135 |
| 5,200,332 | A | 4/1993 | Yamane et al. .............. 435/135 |
| 5,292,860 | A | 3/1994 | Shiotani et al. ............. 528/361 |
| 5,612,161 | A | 3/1997 | Watanabe et al. ........... 430/110 |
| 5,667,927 | A | 9/1997 | Kubota et al. ............... 430/109 |
| 6,808,854 | B2 | 10/2004 | Imamura et al. ............ 430/127 |

FOREIGN PATENT DOCUMENTS

| JP | 60-108861 | 6/1985 |
| JP | 61-3149 | 1/1986 |
| JP | 63-38958 | 2/1988 |
| JP | 63-88564 | 4/1988 |
| JP | 5-7492 | 1/1993 |
| JP | 5-93049 | 4/1993 |
| JP | 6-15604 | 3/1994 |
| JP | 6-289644 | 10/1994 |
| JP | 7-14352 | 2/1995 |
| JP | 7-72658 | 3/1995 |
| JP | 7-120975 | 5/1995 |
| JP | 7-265065 | 10/1995 |
| JP | 8-19227 | 2/1996 |

(Continued)

OTHER PUBLICATIONS

Park, et al., Epoxidation of Bacterial Polyesters with Unsaturated Side Chains. I. Production and Epoxidation of Polyesters from 10-Undecenoic Acid; Macromolecules, 31, 5 1480-1486.

(Continued)

*Primary Examiner*—Herbert J Lilling
(74) *Attorney, Agent, or Firm*—Fitzpatrick, Cella, Harper & Scinto

(57) ABSTRACT

A polyhydroxyalkanoate is disclosed which has in the molecule a unit represented by Chemical Formula (1).

$$\left[ O - \overset{H}{\underset{(CH_2)_x}{C}} - \overset{H_2}{C} - \overset{O}{\overset{\|}{C}} \right] \quad (1)$$

$x = 1-8$ wherein R is arbitrarily selected from a hydrogen atom, a halogen atom, CN, $NO_2$, COOR', $SO_2R''$, $CH_3$, $C_2H_5$, $C_3H_7$, $C(CH_3)_2H$ and $C(CH_3)_3$; where R' is H, Na, K, $CH_3$ or $C_2H_5$, and R'' is OH, ONa, OK, a halogen atom, $OCH_3$ or $OC_2H_5$; and x is an integer arbitrarily selected from 1 to 8; with the proviso that a polyhydroxyalkanoate is excluded which has a hydrogen atom as R and x in all the units is 2 or 4. Also disclosed is a process for producing the polyhydroxyalkanoate by the use of a microorganism having the ability to produce the polyhydroxyalkanoate and accumulate it in the bacterial body.

10 Claims, 26 Drawing Sheets

FOREIGN PATENT DOCUMENTS

| | | |
|---|---|---|
| JP | 8-179564 | 7/1996 |
| JP | 8-262796 | 10/1996 |
| JP | 2623684 | 6/1997 |
| JP | 9-191893 | 7/1997 |
| JP | 2642937 | 8/1997 |
| JP | 9-274355 | 10/1997 |
| JP | 9-281746 | 10/1997 |
| JP | 2807795 | 10/1998 |
| JP | 2989175 | 12/1999 |
| JP | 2001-178484 | 7/2001 |

OTHER PUBLICATIONS

Park, et al., Epoxidation of Bacterial Polyesters with Unsaturated Side Chains. II. Rate of Epoxidation and Polymer Properties; J. Polym. Sci; Part A; Polym. Chem. 36, 2381-2387 (1998).

Aróstegui, et al., "Bacterial Polyesters Produced by *Pseudomonas oleovorans* Containing Nitrophenyl Groups"; Macromolecules, 32, 9, 2889-2895 (1999).

Takagi, et al., Biosynthesis of Polyhydroxyalkanoate with a Thiophenoxy Side Group Obtained from *Pseudomonas putida*; Macromolecules, 32, 25, 8315-8318 (1999).

Fritzche, et al., "An Unusual Bacterial Polyester with a Phenyl Pendant Group"; Makromol. Chem. 191, 1957-1965 (1990).

Kim, et al., "Preparation and Characterization of Poly($\beta$)-hydroxyalkanoates Obtained from *Pseudomonas oleovorans* Grown with Mixtures of 5-Phenylvaleric Acid and n-Alkanoic Acids"; Macromolecules, 24, 5256-5260 (1991).

Lytle, et al., "Filtration Sizes of Human Immunodeficiency Virus Type 1 and Surrogate Viruses Used To Barrier Materials"; Appl. & Environ. Microbiol., 58, 2, 747-749 (1992).

Ritter, et al., "Bacterial Production of Polyesters Bearing Phenoxy Groups in the Side Chains, 1 Poly(3)-hydroxy-5-pnenoxypentanoate-co-3-hydroxy-9-phenoxy-nananoate ) from *Pseudomonas oleovorans*"; Macrol. Chem. Phys., 195, 1665-1672 (1994).

Gross, et al., "Cyanophenoxy-Containing Microbial Polyesters: Structural Analysis, Thermal Properties, Second Harmonic Generation and In-Vivo Biodegradability"; Polymer Int'l., 39, 205-213 (1996).

Curley, et al., Production of Poly(3-hydroxyalkanoates) Containing Aromatic Substituents by *Pseudomonas oleovorans*; Macromolecules, 29, 1762-1766 (1996).

POLYHYDROXYALKANOATE CONTAINING UNIT WITH PHENYLSULFANYL STRUCTURE IN THE SIDE CHAIN, PROCESS FOR ITS PRODUCTION, CHARGE CONTROL AGENT, TONER BINDER AND TONER WHICH CONTAIN NOVEL POLYHYDROXYALKANOATE, AND IMAGE FORMING METHOD AND IMAGE-FORMING APPARATUS WHICH MAKE USE OF THE TONER

CROSS-REFERENCE TO RELATED APPLICATIONS

This is a division of application Ser. No. 10/084,172, filed Feb. 28, 2002.

BACKGROUND OF THE INVENTION

1. Field of the Invention

This invention relates to a novel polyhydroxyalkanoate (hereinafter simply "PHA"), and also relates to a process for producing the PHA comprising the step of producing a PHA by the use of a microorganism having the ability to produce the PHA and accumulate it in the bacterial body.

This invention further relates to a charge control agent, a toner binder and a toner for developing electrostatic latent images, used in recording processes which utilize electrophotography, electrostatic recording, magnetic recording or the like, an image-forming method making use of the toner, and an image-forming apparatus therefore More particularly, it relates to a charge control agent, a toner binder and a toner for developing electrostatic latent images, used in electrophotographic, electrostatic-recording and electrostatic-printing apparatus such as copying machines, printers and facsimile machines, an image-forming method making use of the toner, and an image-forming apparatus therefor. Still more particularly, it relates to a negatively charging charge control agent having higher safety to human bodies and environment, a toner binder and a toner for developing electrostatic latent images, making use of such a charge control agent, an image-forming method making use of the toner, and an image-forming apparatus therefor.

2. Related Background Art

It has hitherto been reported that many microorganisms produce poly-3-hydroxybutyric acid.

(PHB) or other PHA and accumulate it in the bacterial body ("Handbook of Biodegradable Plastics", Biodegradable-Plastic Institute, K.K. N·T·S, pp. 178-197, 1995). Like conventional plastics, these polymers can be utilized for the production of various products by melt processing or the like. Also, since they are biodegradable, they have an advantage of being completely broken down by microorganisms in the natural world, and by no means remain in natural environment to cause pollution as many conventional synthetic polymeric compounds do. They also have superior adaptability to living bodies and are expected to be applicable as medical flexible members.

It is known that such PHAs produced by microorganisms may have various composition and structure depending on the type of microorganisms used for its production, the composition of culture medium, the conditions for culture and so forth. Researches on how to control such composition and structure have hitherto chiefly been made from the viewpoint of the improvement in physical properties of PHAs.

(1) In the first place, as biosyntheses of PHAs by the polymerization of a monomer unit having a relatively simple structure, including 3-hydroxybutyric acid (hereinafter simply "3HB"), the following cases are available.

(a) Those which contain 3HB and 3-hydroxyvaleric acid (hereinafter "3HV"):

Japanese Patent Publications No. 6-156.04, No. 7-14352, No. 8-19227, etc., and Japanese Patent Application Laid-Open No. 5-7492.

(b) Those which contain 3HB and 3-hydroxyhexanoic acid (hereinafter "3HHx"):

Japanese Patent Application Laid-Open No. 5-93049 and No. 7-265065.

(c) Those which contain 3HB and 4-hydroxybutyric acid (hereinafter "4HB"):

Japanese Patent Application Laid-Open No. 9-191893.

(d) Those which contain 3-hydroxyalkanoates having 6 to 12 carbon atoms:

Japanese Patent No. 2642937.

(e) Biosynthesis utilizing a simple fatty acid as a carbon source. Products are substantially the same as those of (d); Appl. Environ. Microbiol., 58(2), 746, 1992.

These are all PHAs each comprised of a monomer unit having an alkyl group in the side chain, i.e., "usual PHA", all synthesized by β-oxidation of hydrocarbons or synthesis of fatty acids from saccharides by the aid of microorganisms.

(2) When, however, broader application of such PHAs produced by microorganisms, e.g., application as functional polymers is taken into account, a PHA in which a substituent other than the alkyl group has been introduced in the side chain, i.e., "unusual PHA" is expected to be very useful. As examples of such a substituent, it may include those containing aromatic rings (such as a phenyl group and a phenoxy group), unsaturated hydrocarbons, an ester group, an ally group, a cyano group, halogenated hydrocarbons and epoxides. Of these, researches are energetically made especially on PHAs having aromatic rings.

(a) Those which contain a phenyl group or a partially substituted phenyl group:

Macromol. Chem. Phys., 191, 1957-1965 (1990) and Macromolecules, 24, 5256-5260 (1991) report that *Pseudomonas oleovorans* produces a. PHA containing 3-hydroxy-5-phenylvaleric acid as a unit, using 5-phenylvaleric acid as a substrate.

Macromolecules, 29, 1762-1766 (1996) reports that *Pseudomonas oleovorans* produces a PHA containing 3-hydroxy-5-(4'-tolyl)valeric acid as a unit, using 5-(4'-tolyl)valeric acid as a substrate.

Macromolecules, 32, 2889-2895 (1999) reports that *Pseudomonas oleovorans* produces a PHA containing 3-hydroxy-5-(2',4'-dinitrophenyl)valeric acid and 3-hydroxy-5-(4'-nitrophenyl)valeric acid as units, using 5-(2',4'-dinitrophenyl)valeric acid as a substrate.

(b) Those which contain a phenoxyl group or a partially substituted phenoxyl group:

Macromol. Chem. Phys., 195, 1665-1672 (1994) reports that *Pseudomonas oleovorans* produces a PHA copolymer of 3-hydroxy-5-phenoxyvaleric acid with 3-hydroxy-9-phenoxynonanoic acid, using 11-phenoxyundecanoic acid as a substrate.

Japanese Patent No. 2989175 discloses invention which is concerned with a homopolymer comprised of a 3-hydroxy-5-(monofluorophenoxy)pentanoate (3H5(MFP)P) unit or a 3-hydroxy-5-(difluorophenoxy)pentanoate (3H5(DFP)P) unit, and a copolymer containing at least the (3H5(MFP)P) unit or the (3H5(DFP)P) unit; *Pseudomonas putida* capable of synthesizing such a polymer; and a process of producing the above polymer by the use of the genus *Pseudomonas*. It is reported that as its effect a polymer the side-chain terminal of which has a phenoxyl group substituted with 1 or 2 fluorine atom(s) can be synthesized by utilizing a long-chain fatty acid having a substituent and that stereo-regularity (syndiotacticity) and water repellency can be imparted having a high melting point and retaining good processability.

In addition to such fluorine-group-substituted products, cyano-group- or nitro-group-substituted products are also on researches.

Can. J. Microbiol., 41, 32-43 (1995) and Polymer International, 39, 205-213 (1996) report that a PHA containing 3-hydroxy-p-cyanophenoxyhexanoic acid or 3-hydroxy-p-nitrophenoxyhexanoic acid as a monomer unit is produced using octanoic acid and p-cyanophenoxyhexanoic acid or p-nitrophenoxyhexanoic acid as a substrate by the use of *Pseudomonas oleovorans* strain ATCC 29347 and *Pseudomonas putida* strain KT 2442.

These reports are useful in order to obtain polymers which all have an aromatic ring in the side chain of PHA, different from the commonly available PHAs having an alkyl group in the side chain, and have physical properties arising therefrom.

(3) As a new category, without limitation merely to changes in physical properties, researches are also made intending to produce a PHA having a suitable functional group in the side chain.

For example, Macromolecules, 31, 1480-1486 (1996) and Journal of Polymer Science: Part A: Polymer Chemistry, 36, 2381-2387 (1998) report that a PHA containing at the side-chain terminal a unit having a vinyl group is synthesized and thereafter the product synthesized is epoxidized with an oxidizing agent and this has enabled synthesis of a PHA containing a highly reactive epoxy group at the side-chain terminal.

Besides the vinyl group, as an example of synthesizing a PHA containing a unit having a thioether (—S—; a sulfanyl linkage), expected to provide a high reactivity, Macromolecules, 32, 8315-8318 (1999) reports that *Pseudomonas putida* strain 27N01 produces a PHA copolymer of 3-hydroxy-5-thiophenoxyvaleric acid (3-hydroxy-5-(phenylsulfanyl)valeric acid) with 3-hydroxy-7-thiophenoxyheptanoic acid (3-hydroxy-7-(phenylsulfanyl)heptanoic acid), using (11-thiophenoxyundecanoic acid (11-(phenylsulfanyl)undecanoic acid) as a substrate.

A number of methods are also conventionally known as methods for electrophotography. In general, copied images are obtained by forming an electrostatic latent image on an image-bearing member (photosensitive member) by utilizing a photoconductive material and by various means, subsequently developing the latent image by the use of a toner to form a visible image (toner image), transferring the toner image to a transfer medium as occasion calls, and then fixing the toner image to the transfer medium by heating and/or pressing. As methods by which the electrostatic latent image is formed into a visible image, cascade development, magnetic brush development, pressure development and so forth are known in the art. Another method is also known in which, using a magnetic toner and a rotary developing sleeve provided with magnetic poles at the core, the magnetic toner is caused to fly from the developing sleeve to the photosensitive member by the aid of an electric field.

As development methods used when electrostatic latent images are developed, available are a two-component development method making use of a two-component type developer comprised of a toner and a carrier and a one-component development method making use of no carrier and comprised only of a toner.

Here, fine colored particles commonly called a toner are constituted of a binder resin and a colorant as essential components and besides optionally a magnetic material and so forth. As methods for imparting electric charges to the toner, the charging properties of the binder resin itself may be utilized without use of any charge control agent. If that is the case, however, the binder resin has poor charging stability with time and poor moisture resistance. Accordingly, a charge control agent is usually added for the purpose of charge retention and charge control of the toner.

Conventional charge control agents nowadays known in the present technical field include, e.g., as negative charge control agents, azo dye metal complexes, metal complexes of aromatic dicarboxylic acids and metal complexes of salicylic acid derivatives. Also, known as positive charge control agents are Nigrosine dyes, triphenylmethane dyes, organotin compounds such as quaternary ammonium salt dibutyltin oxides of various types, and so forth. Toners containing any of these as charge control agents, however, do not necessarily well satisfy quality characteristics such as charging performance and stability with time in some cases, depending on their composition; the characteristics being required in toners.

For example, toners containing the azo dye metal complexes known as negative charge control agents are on a reasonable level in respect of the highness of charge quantity. However, since the azo dye metal complexes are crystal compounds with a low molecular weight, they may have a poor dispersibility depending on the type of binder resins in which they are to be incorporated. In such as case, the negative charge control agents are not uniformly distributed in the binder resins, and the resultant toners also have a charge quantity distribution lacking in sharpness greatly, so that the images to be obtained may have a low gradation, showing a poor image formation performance. Moreover, the azo dye metal complexes have color tone specific thereto, and hence, under the existing conditions, they are used only in toners with hues limited mainly to black. When such toners are used as color toners, what is of a great problem is that they have not any sharpness of coloring agents which is required in order to obtain images having a high requirement for color toner.

As an example of nearly colorless negative charge control agents, the metal complexes of aromatic dicarboxylic acids are available, which, however, may have a problem of low dispersibility because of the fact that they are not perfectly colorless and that they are crystal compounds with a low molecular weight.

As for the Nigrosine dyes and the triphenylmethane dyes, known as positive charge control agents, they stand colored in themselves, and hence, under the existing conditions, they are also used only in toners with hues limited mainly to black, and also may have no good stability with time when such toners are used in continuous copying. Conventional quaternary ammonium salts may also have an insufficient moisture resistance when incorporated in toners. In such a case, such toners may have so poor a stability with time as not to afford any good images in their repeated use.

In recent years, from the viewpoint of environmental conservation, too, what has become a worldwide subject of discussion is how waste be curtailed and how the safety of waste be improved. Such a subject is likewise discussed also in the field of electrophotography. More specifically, with wide spread of image-forming apparatus, the disposal of printed paper, waste toner after use and copying paper is increasing year by year, and the safety of such waste is also an important subject from the standpoint of the conservation of global environment.

Taking account of such a point, studies are being made on polymer type charge control agents. They include compounds disclosed in, e.g., U.S. Pat. No. 4,480,021, No. 4,442,189 and No. 4,925,765 and Japanese Patent Application Laid-Open No. 60-108861, No. 61-3149, No. 63-38958 and No. 63-88564. Also, in general, as polymer type charge control agents used when toners are made to exhibit negative chargeability, there are many examples in which copolymers of styrene and/or α-methylstyrene with alkyl acrylates or methacrylates or alkyl acrylate or methacrylate amides having sulfonic acid groups are used (Japanese Patent Application Laid-Open No. 7-72658 and No. 8-179564 and Japanese Patents No. 2114410, No. 2623684 and No. 2807795). Such materials are advantageous in that they are colorless, but must be added in a large quantity in order to ensure charge quantity.

Thus, these compounds do not have any sufficient performance as charge control agents, and have problems on charge quantity, charging-rise performance, stability with time, environmental stability and so forth. Also, considering not only the aspect of function but also any influence on human bodies and environment, it is strongly sought in respect of compounds and organic solvents used in synthesis, too, to provide a safer compound, a safer and milder synthesis process, and a charge control agent which can achieve use of organic solvents in a smaller quantity.

From the viewpoint of environmental conservation, development is being made on resins degradable with time by the action of microorganisms, i.e., biodegradable resins. For example, as stated previously, it has been reported that many microorganisms are capable of producing the biodegradable resin PHA and accumulating it in the bacterial body. It is known that such PHA can have various composition and structure depending on the type of microorganisms used for its production, the composition of culture medium, the conditions for fermentation and so forth. Researches on how to control such composition and structure have hitherto chiefly been made from the viewpoint of the improvement in physical properties of PHA. With regard to its application, too, they have already given reasonable actual results especially in the field of materials for medical use. In the field of agriculture, too, the biodegradable resins are used in multifiles, gardening material and so forth, and also in sustained-release agricultural chemicals, fertilizers and so forth. In the field of leisure industry, too, the biodegradable resins are used in fishing lines, fishing articles, golf goods and so forth.

However, considering their wide application as plastics, under the existing conditions they can not still be said to be satisfactory in respect of physical properties. In order to make the PHA utilizable in much wider ranges, it is important to study the improvement of physical properties more widely. For that end, it is essential to make development and research on PHAs containing monomer units of various structures. Meanwhile, the PHA of the type a substituent has been introduced in the side chain can be expected to be expanded as a "functional polymer" having-very useful functions and properties attributable to the properties of the substituent introduced, by selecting according to the desired properties and so forth the substituent to be introduced. Namely, it is also an important subject to make development and research on such a PHA that can achieve both such functional factors and the biodegradability.

In the field of electrophotography, too, the application of biodegradable resins to binder resins is proposed especially in the production of toners. For example, U.S. Pat. No. 5,004,664 discloses a toner having as its composition a biodegradable resin, in particular, polyhydroxybutyric acid, polyhydroxyvaleric acid, or a copolymer or blend of these. Japanese Patent Application Laid-Open No. 6-289644 also disclose an electrophotographic toner particularly used for heat-roll fixing, which is characterized in that at least a binder resin contains a vegetable wax and a biodegradable resin (as exemplified by polyesters produced by microorganisms and natural polymeric materials derived from vegetables or animals), and the vegetable wax is added to the binder resin in an amount of from 5 to 50% by weight.

Japanese Patent Application Laid-Open No. 7-120975 also discloses an electrophotographic toner characterized by containing a lactic-acid resin as a binder resin. Japanese Patent Application Laid-Open No. 9-274355 still also discloses a toner for developing electrostatic latent images which is characterized by containing a polyester resin and a colorant; the former being obtained by dehydration polycondensation of a composition containing lactic acid and a tri- or more functional oxycarboxylic acid.

Japanese Patent Application Laid-Open No. 8-262796 also discloses an electrophotographic toner containing a binder resin and a colorant, and is characterized in that the binder resin comprises a biodegradable resin (as exemplified by aliphatic polyester resins) and the colorant comprises a water-insoluble coloring matter. Japanese Patent. Application Laid-Open No. 9-281746 still also discloses a toner for developing electrostatic latent images which is characterized by containing a urethanated polyester resin and a colorant; the former being obtained by cross-linking polylactic acid with a tri- or more functional polybasic isocyanate.

In all the electrophotographic toners stated above, biodegradable resins are used as their binder resins, and they are understood to have the effect of contributing to the environmental safeguard and so forth.

However, any report on an example in which biodegradable resins are used in charge control agents is still unknown. Thus, there is room for further progress in respect of the contribution to the environmental safeguard and so forth.

When taking note of the PHA containing a 3-hydroxy-thiophenoxyalkanoic acid (3-hydroxy-(phenylsulfanyl)alkanoic acid) unit, it is expected that researches are hereafter made more and more in order for the functional PHA to be developed on, in view of the highness of reactivity of the thioether (—S—; a sulfanyl linkage). However, with regard to such a kind of PHA, there is nothing but one report given above. Moreover, the above method employs as a raw material the carboxylic acid having a large carbon chain length, utilizes the β-oxidation system in which the carbon chain becomes short two by two in the microorganism, and incorporates as a polymer unit the 3-hydroxyalkanoic acid having shorter carbon chain than the raw material. Hence, there has been a problem that it is difficult to control polymer structure.

Furthermore, in order that the PHA having-such a unit is made to have various uses, the PHA must have physicochemical properties corresponding to such uses. For that purpose, a PHA containing a 3-hydroxy-(phenylsulfanyl)alkanoic acid unit having a functional substituent of various types in the aromatic-ring moiety must be developed. However, such a PHA has not been reported.

SUMMARY OF THE INVENTION

An object of the present invention is to provide a novel polyhydroxyalkanoate containing a 3-hydroxy-(phenylsulfanyl)alkanoic acid unit having a phenylsulfanyl structure at the side chain, a novel polyhydroxyalkanoate containing a 3-hydroxy-(phenylsulfanyl)alkanoic acid unit having a functional substituent in the aromatic-ring moiety, and a process for producing the same. Another object of the present invention is to provide a raw-material thereof, a (phenylsulfanyl)alkanoic acid having a functional substituent in its aromatic-ring moiety, and a process for producing the same.

A further object of the present invention is, in order to solve the above problems in electrophotographic processes, to provide a negatively charging charge control agent which is more highly contributory to the environmental safeguard and so forth from the aspect of function and also has high performances (i.e., high charge quantity, quick rise in charging, good stability with time and high environmental stability), and has been improved in dispersibility, utilizing the above novel polyhydroxyalkanoate containing a 3-hydroxy-(phenylsulfanyl)alkanoic acid unit having a functional substituent in the aromatic-ring moiety; and a toner binder comprising such a charge control agent, a toner for developing electrostatic latent images which comprises the charge control agent, and an image-forming method and an image-forming apparatus which make use of the toner for developing electrostatic latent images.

Accordingly, the present inventors have repeated extensive researches aiming at the development of a novel polyhydroxyalkanoate containing a 3-hydroxy-(phenylsulfanyl)alkanoic acid unit having a phenylsulfanyl structure at the side chain, a novel polyhydroxyalkanoate containing a 3-hydroxy-(phenylsulfanyl)alkanoic acid unit having a functional substituent in the aromatic-ring moiety, which is considered useful as materials in the field of high-technology, such as device materials and medical materials. As the result, they have accomplished the invention as described below. That is, the summary of the present invention is as follows:

The present invention provides a polyhydroxyalkanoate characterized by having in the molecules a unit represented by Chemical Formula (1).

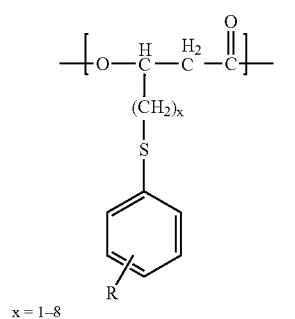

wherein R is arbitrarily selected from a hydrogen atom, a halogen atom, CN, $NO_2$, COOR', $SO_2R''$, $CH_3$, $C_2H_5$, $C_3H_7$, $C(CH_3)_2H$ and $C(CH_3)_3$; where R' is H, Na, K, $CH_3$ or $C_2H_5$, and R" is OH, ONa, OK, a halogen atom, $OCH_3$ or $OC_2H_5$; and x is an integer arbitrarily selected from 1 to 8, with the proviso that a polyhydroxyalkanoate is excluded which has a hydrogen atom as R and x in all the units is 2 or 4.

The present invention still also provides a process for producing a polyhydroxyalkanoate having in the molecule the unit represented by Chemical Formula (1); the process comprising culturing a microorganism in a culture medium containing at least one compound represented by Chemical Formula (14). Here, a polyhydroxyalkanoate is excluded which consists of the two units which are present in a molecule chain at the same time where R is hydrogen atom and x is 2 or 4.

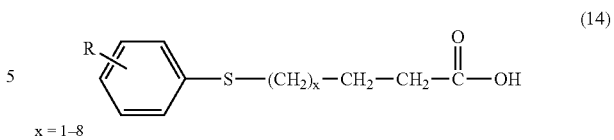

wherein R is arbitrarily selected from a hydrogen atom, a halogen atom, CN, $NO_2$, COOR', $SO_2R''$, $CH_3$, $C_2H_5$, $C_3H_7$, $C(CH_3)_2H$ and $C(CH_3)_3$; where R' is H, Na, K, $CH_3$ or $C_2H_5$, and R" is OH, ONa, OK, a halogen atom, $OCH_3$ or $OC_2H_5$; and x may assume any one integral value within the range shown in the chemical formula.

The present invention further provides a process for producing a polyhydroxyalkanoate having in the molecule the unit represented by Chemical Formula (1) the process comprising the step of preparing a culture medium containing at least one compound represented by Chemical Formula (14) and polypeptone, and the step of culturing a microorganism in the culture medium. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule a unit represented by Chemical Formula (1); the process comprising the step of preparing a culture medium containing at least one compound represented by Chemical Formula (14) and yeast extract, and the step of culturing a microorganism in the culture medium. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule a unit represented by Chemical Formula (1); the process comprising the step of preparing a culture medium containing at least one compound represented by Chemical Formula (14) and saccharide, and the step of culturing a microorganism in the culture medium. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule a unit represented by Chemical Formula (1); the process comprising the step of preparing a culture medium containing at least one compound represented by Chemical Formula (14) and an organic acid or a salt thereof, and the step of culturing a microorganism in the culture medium. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule a unit represented by Chemical Formula (1); the process comprising the step of preparing a culture medium containing at least one compound represented by Chemical Formula (14) and amino acid or a salt thereof, and the step of culturing a microorganism in the culture medium. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule a unit represented by Chemical Formula (1); the process comprising the step of preparing a culture medium containing at least one compound represented by Chemical Formula (14) and a straight-chain alkanoic acid having 4 to 12 carbon atoms or a salt thereof, and the step of culturing a microorganism in the culture medium. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule a unit represented by Chemical Formula (1); the process comprising the steps of: (step 1-1) culturing a microorganism in a culture medium containing at least one compound represented by Chemical Formula (14) and containing polypeptone; and subsequently thereto; (step 2-1) further culturing the microorganism cultured in the step 1-1, in a culture medium containing at least one compound represented by Chemical Formula (14) and containing an organic acid or a salt thereof. The culturing step of (step 2-1) may be a culturing step in which nitrogen source content is low or is not contained. Here, a polyhydroxyalkanoate is excluded which consists of the two units which are present in a molecule chain at the same time where R is hydrogen atom and x is 2 or 4.

The present invention further provides a process for producing a polyhydroxyalkanoate having in the molecule the unit represented by Chemical Formula (1); the process comprising the steps of:

(step 1-2) culturing a microorganism in a culture medium containing at least one compound represented by Chemical Formula (14) and containing a saccharide;

and subsequently thereto; (step 2-2) further culturing the microorganism cultured in the step 1-2, in a culture medium containing at least one compound represented by Chemical Formula (14) and containing a saccharide. The culturing step of (step 2-2) may be a culturing step in which nitrogen source content is low or is not contained. Here, a polyhydroxyalkanoate is excluded which consists of the two units which are present in a molecule chain at the same time where R is hydrogen atom and x is 2 or 4.

The present invention still further provides a process for producing the polyhydroxyalkanoate in which the microorganism is cultured in a culture medium containing a 4-[(4-fluorophenyl)sulfanyl]butyric acid (hereinafter, may be simply "3HFTPxB") represented by Chemical Formula (18), to produce a polyhydroxyalkanoate containing a 3-hydroxy-4-[(4-fluorophenyl)sulfanyl]butyric acid unit represented by Chemical Formula (8).

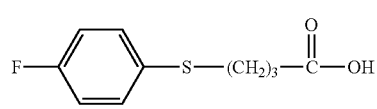
(18)

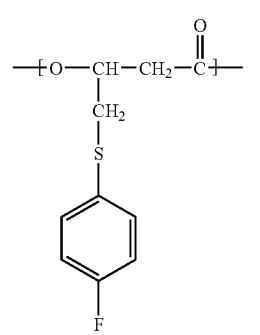
(8)

In addition, the present invention provides the process comprising the step of recovering a polyhydroxyalkanoate from the microorganism cells.

The present invention still further provides, in a process for producing a polyhydroxyalkanoate having in the molecule the unit represented by Chemical Formula (1), in particular, a polyhydroxyalkanoate having in the molecule a 3-hydroxy-[(4-sulfophenyl)sulfanyl]alkanoic acid unit represented by Chemical Formula (20), a process for producing a polyhydroxyalkanoate having in the molecule the unit represented by Chemical Formula (20); the process comprising the step of sulfonating with chlorosulfuric acid a polyhydroxyalkanoate having in the molecule a 3-hydroxy-(phenylsulfanyl)alkanoic acid unit represented by Chemical Formula (19).

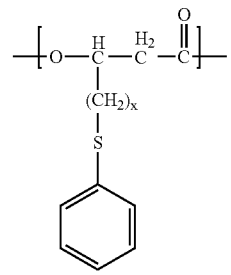
(19)

x = 1–8 wherein x may assume any one integral value within the range shown in the chemical formula.

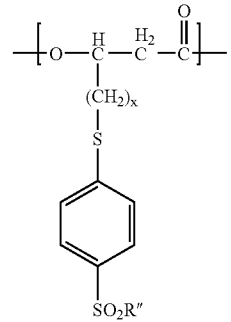
(20)

x = 1–8 wherein R" is arbitrarily selected from OH, ONa and OK; and x may assume any one integral value within the range shown in the chemical formula.

The present invention still further provides a process for producing a polyhydroxyalkanoate having in the molecule a unit represented by Chemical Formula (1); the process comprising the step of allowing a polyhydroxyalkanoate having in the molecule a 3-hydroxy-ω-bromoalkanoic acid unit represented by Chemical Formula (22), to react with a substituted benzenethiol represented by Chemical Formula (23).

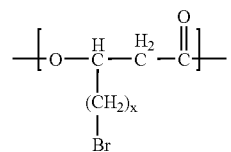

(22)

x = 1–8 wherein x may assume any one integral value within the range shown in the chemical formula.

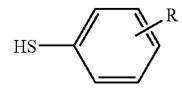

(23)

wherein R is arbitrarily selected from a hydrogen atom, a halogen atom, CN, NO$_2$, COOR' and SO$_2$R', CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$.

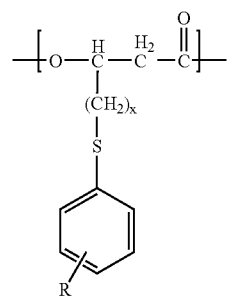

(1)

x = 1–8 wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$; and x is an integer arbitrarily selected from 1 to 8; with the proviso that a polyhydroxyalkanoate is excluded which has a hydrogen atom as R and x in all the units is 2 or 4.

The present invention still further provides a process for producing a polyhydroxyalkanoate having in the molecule a unit represented by Chemical Formula (1); the process comprising the step of allowing a polyhydroxyalkanoate having in the molecule a 3-hydroxy-ω-alkenoic acid unit represented by Chemical Formula (28), to react with a substituted benzenethiol represented by Chemical Formula (23).

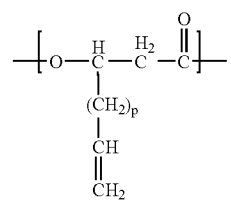

(28)

p = 0–6 wherein p may assume any one integral value within the range shown in the chemical formula.

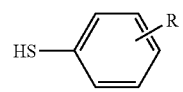

(23)

wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$.

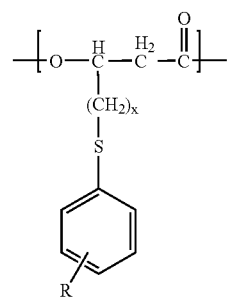

(1)

X = 2–8 wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$; and x is an integer arbitrarily selected from 2 to 8; with the proviso that a polyhydroxyalkanoate is excluded which has a hydrogen atom as R and x in all the units is 2 or 4.

A novel polyhydroxyalkanoate according to the present invention has monomer unit which is 3-hydroxyalkanoic acid itself aromatic ring or thioether(sulfanyl) structure. The structure provides a high reactivity, and the substituent of the aromatic ring moiety contributes various physicochemical properties. The polyhydroxyalkanoate is produced directly from, using a microorganism having PHA productivity, a culture medium containing the corresponding (phenylsulfanyl)alkanoic acid or [(substituted phenyl)sulfanyl]alkanoic acid and a carbon source for multiplication, or is obtained by chemically modifying the aromatic ring moiety of 3-hydroxy-(phenylsulfanyl)alkanoic acid, or is obtained by reacting 3-hydroxy-ω-bromoalkanoic acid or 3-hydroxy-ω-alkenoic acid with substituted a substituted benzenethiol.

The present inventors have made further extensive studies aiming at the development of such a charge control agent which is more highly contributory to the environmental safeguard and so forth and also has high performances. As the result, they have accomplished the present invention.

That is, the present invention is a charge control agent comprising a polyhydroxyalkanoate having in the molecule at least one unit of units represented by Chemical Formula (1).

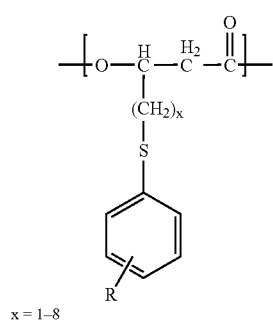

(1)

$x = 1-8$ wherein R is arbitrarily selected from COOR' and $SO_2R''$; where R' is H, Na, K, $CH_3$ or $C_2H_5$, and R" is OH, ONa, OK, a halogen atom, $OCH_3$ or $OC_2H_5$; and x may assume any one integral value within the range shown in the chemical formula.

The polyhydroxyalkanoate contained in the charge control agent of the present invention may contain, in addition to the unit represented by Chemical Formula (1), each independently or the both of units represented by Chemical Formulas (2) and (3).

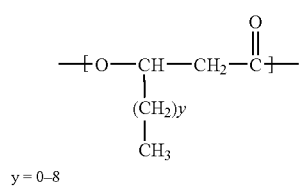

(2)

$y = 0-8$

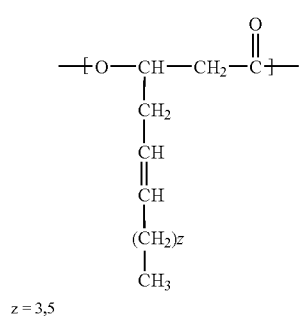

(3)

$z = 3, 5$ wherein y and z may assume any one integral value within the range shown in the chemical formulas, independently from the unit represented by Chemical. Formula (1).

The polyhydroxyalkanoate contained in the charge control agent of the present invention may have a number-average molecular weight in the range of from 1,000 to 500,000.

The present invention also provides a toner binder comprising a charge control agent having the above polyhydroxyalkanoate.

The present invention further provides a toner for developing electrostatic latent images which comprises a binder resin, a colorant and a charge control agent having the above polyhydroxyalkanoate.

The present invention still further provides an image-forming method comprising:

a charging step of applying a voltage to a charging member from its outside to charge an electrostatic-latent-image-bearing member electrostatically;

a latent-image-forming step of forming an electrostatic latent image on the electrostatic-latent-image-bearing member thus charged;

a developing step of developing the electrostatic latent image by the use of a toner for developing electrostatic latent images, to form a toner image on the electrostatic-latent-image-bearing member;

a transfer step of transferring to a recording medium the toner image formed on the electrostatic-latent-image-bearing member; and a heat fixing step of fixing by heat the toner image held on the recording medium;

wherein the toner for developing electrostatic latent images comprises a binder resin, a colorant and a charge control agent containing the above polyhydroxyalkanoate.

The present invention still further provides an image-forming apparatus comprising:

a charging means for applying a voltage to a charging member from its outside to charge an electrostatic-latent-image-bearing member electrostatically;

a latent-image-forming means for forming an electrostatic latent image on the electrostatic-latent-image-bearing member thus charged;

a developing means for developing the electrostatic latent image by the use of a toner for developing electrostatic latent images, to form a toner image on the electrostatic-latent-image-bearing member;

a transfer means for transferring to a recording medium the toner image formed on the electrostatic-latent-image-bearing member; and a heat fixing means for fixing by heat the toner image held on the recording medium;

wherein the toner for developing electrostatic latent images comprises a binder resin, a colorant and a charge control agent containing the above polyhydroxyalkanoate.

DETAILED DESCRIPTION OF THE PREFERRED EMBODIMENTS

Figure 1:
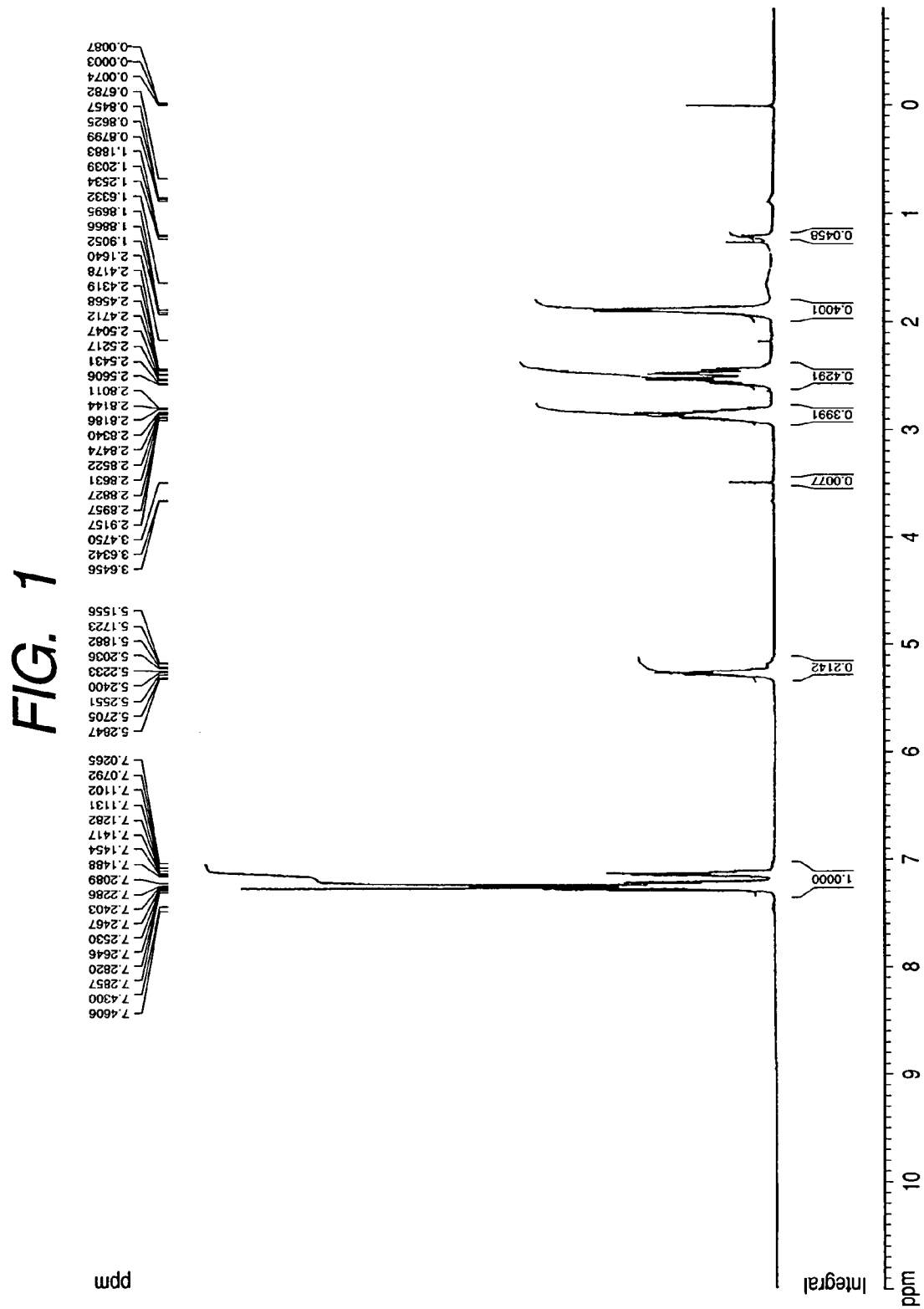
FIG. 1 is a $^1$H-NMR spectrum chart of a polymer obtained according to Example 1.

The microorganism used in the process of the present invention may be any microorganism as long as it is a microorganism capable of producing the polyhydroxyalkanoate having in the molecule the unit represented by Chemical Formula (1), by culturing the microorganism in a culture medium containing the compound represented by Chemical Formula (14). As an example thereof, it may include microorganisms belonging to the genus. *Pseudomonas*. Stated more specifically, the microorganism may include *Pseudomonas cichorii* strain YN2 (FERM BP-7375), *Pseudomonas cichorii* strain H45 (FERM BP-7374), *Pseudomonas jessenii* strain P161 (FERM BP-7376) and *Pseudomonas putida* strain P91 (FERM BP-7373). These four kinds of microorganisms have been deposited in International Patent Organization Depositary (IPOD) in National Institute of Advanced Industrial Science and Technology (AIST) and are microorganisms disclosed in Japanese Patent Application Laid-Open No. 2001-178484.

(Culturing Process)

For usual culture of microorganisms used in the the PHA production process according to the present invention, e.g., for the preparation of storage strains and for the proliferation to ensure the number of microorganism and active state which are required to produce the PHA, a culture medium containing ingredients necessary for the proliferation of microorganisms to be used may be used under appropriate selection. For example, any type of culture mediums such as commonly available natural culture mediums (such as nutrient broth and yeast extract) and synthetic mediums to which nutrient sources have been added may be used as long as they do not adversely affect the growth and existence of microorganisms. Culture conditions such as temperature, aeration and stirring may appropriately be selected according to microorganisms to be used.

To produce the desired polyhydroxyalkanoate by using the PHA-productive microorganism described above, an inorganic culture medium may be used which contains at least i) the compound represented by Chemical Formula (14), corresponding to the monomer unit, as a material for producing the PHA and ii) a carbon source for the proliferation of microorganisms. The compound represented by Chemical Formula (14) may preferably be contained in a proportion of from 0.01% to 1% (w/v), and more preferably from 0.02% to 0.2% (w/v), per culture medium. It is not necessarily well water-soluble, but has no problem at all even when it is in the state of being suspended, as long as the microorganism shown in the present invention is used. Also, in some cases, it may be contained in the culture medium in the form that it has been dissolved or suspended in a solvent such as 1-hexane or n-hexadecane. In such a case, it is necessary for the solvent to be in a concentration of 3% or less based on the culture medium solution or suspension.

As a substrate for proliferation, a nutrient source such as yeast extract, polypeptone or meet extract may be used. The substrate may also appropriately be selected from, e.g., saccharides, organic acids occurring as intermediates of the TCA (tricarboxylic acid) cycle, or organic acids obtained by biochemical reaction of further one stage to two stages from the TCA cycle, or salts thereof, amino acids or salts thereof, and straight-chain alkanoic acids having 4 to 12 carbon atoms or salts thereof, taking account of the utility required as substrates for strains to be used.

Of these, the saccharides may include aldoses such as glyceraldehyde, erythrose, arabinose, xylose, glucose, galactose, mannose and fructose; alditols such as glycerol, erythritol and xylitol; aldones such as gluconic acid; uronic acids such as glucuronic acid and galacturonic acid; and disaccharides such as maltose, sucrose and lactose. At least one compound selected from these may preferably be used.

The organic acids or salts thereof may include pyruvic acid, malic acid, lactic acid, citric acid, succinic acid, oxalacetic, isocitric acid, ketoglutaric acid and fumaric acid, or salts of these, and at least one compound selected from these may preferably be used.

The amino acids or salts thereof may include glutamic acid and aspertic acid, or salts of these, and at least one compound selected from these may preferably be used.

In particular, it is preferable to use polypeptones and saccharides. Of the saccharides, at least one selected from the group consisting of glucose, fructose and mannose is preferred. Any of these substrates may usually preferably be contained in a proportion of from 0.1% to 5% (w/v), and more preferably from 0.2% to 2% (w/v), per culture medium.

As a method for making the microorganism produce and accumulate the PHA, the PHA may first sufficiently be proliferated and thereafter the bacterial body may be moved to a culture medium in which a nitrogen source such as ammonium chloride has been restricted, followed by further culturing in the state the compound serving as the substrate of the desired unit has been added. This may bring about an improvement in productivity. Stated specifically, a multistage method in which the above step is connected in a multiple stage may be employed.

It is exemplified by;

a method in which the step of (step 1-1) culturing the microorganism in a culture medium containing the compound represented by Chemical Formula (14) and a polypeptone is continued from the latter phase of logarithmic growth up to a point of time of the stationary phase, and the bacterial body formed is collected by centrifugation or the like, subsequently followed by the step of (step 2-1) further culturing the microorganism cultured in the step 1-1, in a culture medium containing the compound represented by Chemical Formula (14) and an organic acid or a salt thereof; and a method in which the step of (step 1-2) culturing the microorganism in a culture medium containing the compound represented by Chemical Formula (14) and a saccharide is continued from the latter phase of logarithmic growth up to a point of time of the stationary phase, and the bacterial body formed is collected by centrifugation or the like, subsequently followed by the step of (step 2-2) further culturing the microorganism cultured in the step 1-2, in a culture medium containing the compound represented by Chemical Formula (14) and a saccharide.

In the case of these culture methods, the culture medium used in the second-stage culturing (steps 2-1 and 2-2) may be brought into a condition in which the compound serving as a nitrogen source has greatly been restricted or is not contained. This enables the polyhydroxyalkanoate to be produced in a larger quantity in some cases.

As culture temperature, it may be temperature at which the above strain can well be proliferated. For example, it may suitably be from 15° C. to 40° C., preferably from 20° C. to 35° C., and more preferably from 20° C. to 30° C., in approximation.

The culture may be carried out by any culturing method as along as it is a culturing method in which the microorganism proliferates to produce the PHA, such as solid culture. Also usable are batch culture, fed batch culture, semi-continuous culture and continuous culture, without regard to types, As forms of liquid batch culture, a method is available in which the culture medium is shaken in a shaking flask, and a method in which oxygen is fed by a stirring aeration system using a jar fermenter.

The inorganic culture medium used in the above culture methods may be any of those which contain ingredients necessary for the proliferation of the microorganism, such as a phosphorus source (e.g., phosphate) and a nitrogen source (e.g., ammonium salt or nitrate), and may include, e.g., MSB medium and M9 medium.

Composition of an inorganic-salt culture medium (M9 medium) used in one method of the present invention is shown below.

| M9 medium: | |
|---|---|
| $Na_2HPO_4$ | 6.2 g |
| $KH_2HPO_4$ | 3.0 g |
| NaCl | 0.5 g |
| $NH_4Cl$ | 1.0 g |

(in 1 liter of the culture medium; pH: 7.0)

For the purpose of good proliferation and PHA production, about 0.3% (v/v) of a trace-ingredient solution shown below must be added to the above inorganic salt culture medium.

| Trace-ingredient solution: | |
|---|---|
| Nitrilotriacetic acid | 1.5 g |
| $MgSO_4$ | 3.0 g |
| $MnSO_4$ | 0.5 g |
| NaCl | 1.0 g |
| $FeSO_4$ | 0.1 g |
| $CaCl_2$ | 0.1 g |
| $CoCl_2$ | 0.1 g |
| $ZnSO_4$ | 0.1 g |
| $CuSO_4$ | 0.1 g |
| $AlK(SO_4)_2$ | 0.1 g |
| $H_3BO_3$ | 0.1 g |
| $Na_2MoO_4$ | 0.1 g |
| $NiCl_2$ | 0.1 g |

(in 1 liter of solution)

(Separation Step)

In the present invention, as a method for separating the desired PHA from microorganism cells thus cultured, any method usually carried out may be used. For example, extraction with an organic solvent such as chloroform, dichloromethane or acetone is most simple. Besides, dioxane, tetrahydrofuran or acetonitrile is used in some cases. Also, in an environment which should be kept from use of organic solvents, a method may be used in which bacterial-body components other than the PHA are removed to collect the PHA, by treating microorganism cells with a surface-active agent such as SDS (sodium dodecyl sulfate), treating them with an enzyme such as lysozyme, treating them with a chemical such as EDTA (ethylenediaminetetraacetic acid), or physically crushing them using a method of any of ultrasonic crushing, homogenizer crushing, pressure crushing, beads impact crushing, frictional crushing, automated-mortar crushing and freeze-thaw processing.

The culturing of microorganisms according to the present invention, the production of the PHA and its accumulation in the bacterial body according to the present invention, and the collection of the PHA from the bacterial body in the present invention are by no means limited to the above methods.

As a process for producing the PHA of the present invention, a process is also available in which a PHA serving as a precursor of the end product is chemically treated. This process is described below.

(Sulfonation Process)

As a process for producing the PHA of the present invention, in particular, a polyhydroxyalkanoate having in the molecule a 3-hydroxy-[(4-sulfophenyl)sulfanyl]alkanoic acid unit represented by Chemical Formula (20), a process is available which comprises the step of sulfonating with chlorosulfuric acid a polyhydroxyalkanoate having in the molecule a 3-hydroxy-(phenylsulfanyl)alkanoic acid unit represented by Chemical Formula (19).

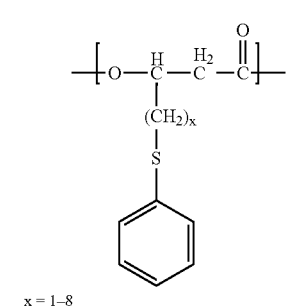

(19)

x = 1–8 wherein x may assume any one integral value within the range shown in the chemical formula (198).

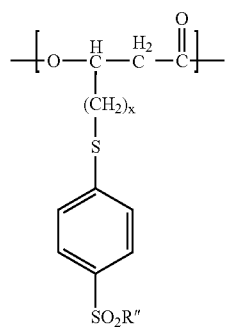

(20)

x = 1–8 wherein R" is arbitrarily selected from OH, ONa and OK; and x may assume any one integral value within the range shown in the chemical formula.

Stated specifically, the polyhydroxyalkanoate having in the molecule the 3-hydroxy-(phenylsulfanyl)alkanoic acid unit represented by Chemical Formula (19) is dissolved in a solvent such as chloroform, and chlorosulfuric acid is dropwise added to the resultant solution under ice cooling, whereby the aromatic ring of the 3-hydroxy-(phenylsulfanyl)alkanoic acid unit can selectively be sulfonated at the 4-position (para-position). With further progress of the reaction, there is a possibility that the sulfone group is introduced also to the 2-position or 6-position (ortho-position).

In this case, the chlorosulfuric acid may dropwise be added in an amount of approximately from 0.5 mL to 5 mL per 1 g of the polymer. The reaction may preferably be carried out at a temperature of approximately from −20 to 20° C., and more preferably approximately from −10 to 10° C.

In this process, the polyhydroxyalkanoate having in the molecule the 3-hydroxy-(phenylsulfanyl)alkanoic acid unit represented by Chemical Formula (19) may also be produced by a process comprising the step of culturing a microorganism in a culture medium containing at least one (phenylsulfanyl)alkanoic acid represented by Chemical Formula (21).

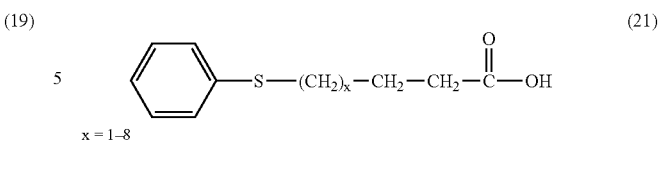

x = 1–8 wherein x may assume any one integral value within the range shown in the chemical formula.

The microorganism used in this process, the culturing of the microorganism, the production of the PHA and its accumulation in the bacterial body by the microorganism, and the collection of the PHA from the bacterial body may be the same as those in the process described previously.

Such a process enables production of, e.g., a polyhydroxyalkanoate having in the molecule a 3-hydroxy-5-[(4-sulfophenyl)sulfanyl]valeric acid unit represented by Chemical Formula (9), from a polyhydroxyalkanoate having in the molecule a 3-hydroxy-5-(phenylsulfanyl)valeric acid unit represented by Chemical Formula (4).

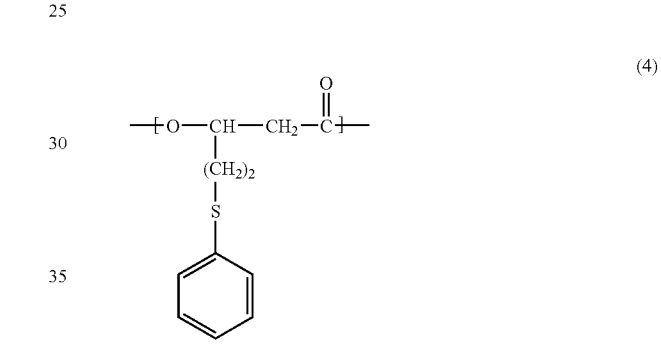

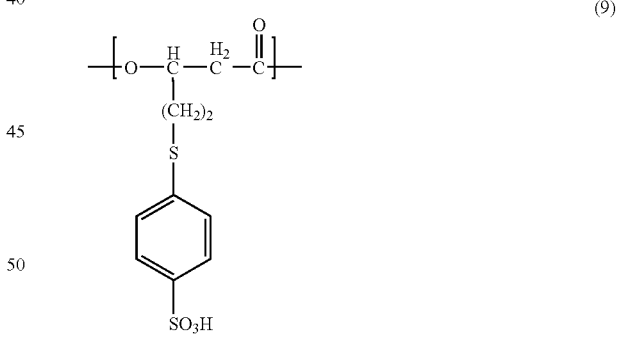

(Reaction of Bromo Group or Vinyl Group with Benzenethiol)

As a process for producing the polyhydroxyalkanoate having in the molecule the unit represented by Chemical Formula (1), a process is available which comprises the step of allowing a polyhydroxyalkanoate having in the molecule a 3-hydroxy-ω-bromoalkanoic acid unit represented by Chemical Formula (22), to react with a substituted benzenethiol represented by Chemical Formula (23).

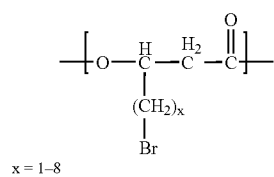

(22)

x = 1–8 wherein x may assume any one integral value within the range shown in the chemical formula.

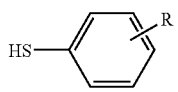

(23)

wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$.

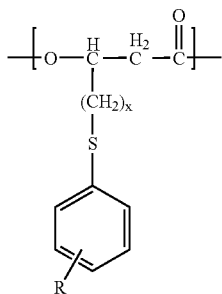

(1)

x = 1–8 wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$; and x is an integer arbitrarily selected from 1 to 8; with the proviso that a polyhydroxyalkanoate is excluded which has a hydrogen atom as R and x in all the units is 2 or 4.

The reaction may preferably be carried out under a basic condition. Stated more specifically, a process is available in which a solution of the polyhydroxyalkanoate having in the molecule the 3-hydroxy-ω-bromoalkanoic acid unit represented by Chemical Formula (22) is dissolved in acetone, followed by reaction with the substituted benzenethiol represented by Chemical Formula (23) in the presence of potassium carbonate, and preferably further in the presence of sodium iodide; or a process in which a solution of the polyhydroxyalkanoate having in the molecule the 3-hydroxy-ω-bromoalkanoic acid unit represented by Chemical Formula (22) is dissolved in dimethylformamide (hereinafter often "DMF"), followed by reaction with the substituted benzenethiol represented by Chemical Formula (23) in the presence of diethylamine.

In this case, the substituted benzenethiol to react with may suitably be in an amount which is equimolar to 2-fold-molar with respect to the 3-hydroxy-ω-bromoalkanoic acid unit. The reaction may preferably be carried out at a temperature of approximately from 15° C. to 30° C.

In this process, the polyhydroxyalkanoate having in the molecule the 3-hydroxy-ω-bromoalkanoic acid unit represented by Chemical Formula (22) may also be produced by a process comprising the step of culturing a microorganism in a culture medium containing at least one ω-bromoalkanoic acid represented by Chemical Formula (24).

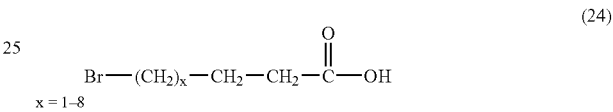

(24)

x = 1–8 wherein x may assume any one integral value within the range shown in the chemical formula.

The microorganism used in this process, the culturing of the microorganism, the production of the PHA and its accumulation in the bacterial body by the microorganism, and the collection of the PHA from the bacterial body may be the same as those in the process described previously.

Such a process enables production of, e.g., a polyhydroxyalkanoate having in the molecule at least one of a 3-hydroxy-8-[(4-carboxyphenyl)sulfanyl]octanoic acid unit represented by Chemical Formula (10) and a 3-hydroxy-6-[(4-carboxyphenyl)sulfanyl]hexanoic acid unit represented by Chemical Formula (11), from a polyhydroxyalkanoate having at least one of a 3-hydroxy-8-bromooctanoic acid unit represented by Chemical Formula (25) and a 3-hydroxy-6-bromohexanoic acid unit represented by Chemical Formula (26), and 4-mercaptobenzoic acid represented by Chemical Formula (27).

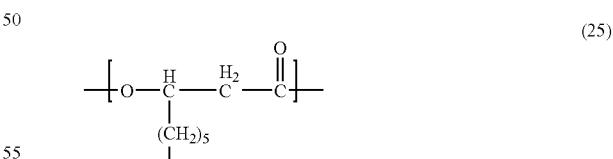

(25)

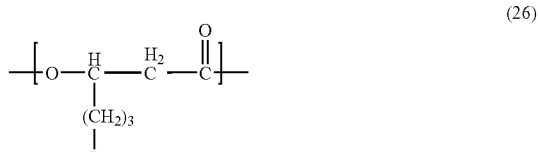

(26)

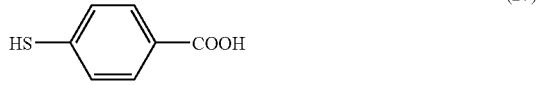

(27)

-continued

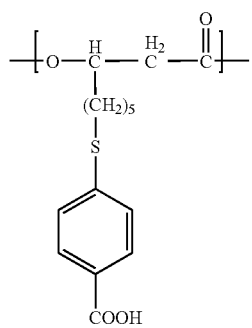
(10)

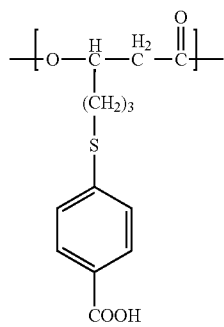
(11)

As a process for producing the polyhydroxyalkanoate having in the molecule the unit represented by Chemical Formula (1), a process is further available which comprises the step of allowing a polyhydroxyalkanoate having in the molecule a 3-hydroxy-ω-alkenoic acid unit represented by Chemical Formula (28), to react with a substituted benzenethiol represented by Chemical Formula (23).

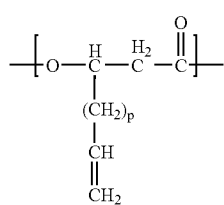
(28)

p = 0–6 wherein p may assume any one integral value within the range shown in the chemical formula.

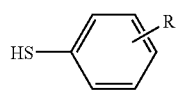
(23)

wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$.

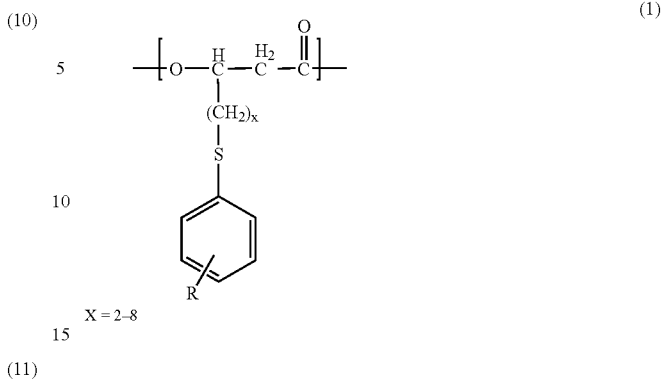
(1)

X = 2–8 wherein R is arbitrarily selected from a hydrogen atom, a halogen atom, CN, NO$_2$, COOR' and SO$_2$R", CH$_3$, C$_2$H$_5$, C$_3$H$_7$, C(CH$_3$)$_2$H and C(CH$_3$)$_3$; where R' is H, Na, K, CH$_3$ or C$_2$H$_5$, and R" is OH, ONa, OK, a halogen atom, OCH$_3$ or OC$_2$H$_5$; and x is an integer arbitrarily selected from 2 to 8; with the proviso that a polyhydroxyalkanoate is excluded which has a hydrogen atom as R and x in all the units is 2 or 4.

Making this reaction proceed requires a free-radical polymerization initiator such as a diacyl peroxide compound. Stated more specifically, a process is available in which the polyhydroxyalkanoate having in the molecule the 3-hydroxy-ω-alkenoic acid unit represented by Chemical Formula (28) is dissolved in a solvent such as chloroform, followed by reaction with the substituted benzenethiol represented by Chemical Formula (23) in the presence of benzoyl peroxide (hereinafter often "BPO").

In this case, the substituted benzenethiol to react with may suitably be in an amount which is equimolar to 2-fold-molar with respect to the 3-hydroxy-ω-alkenoic acid unit. The reaction may preferably be carried out at a temperature which allows the solvent to be refluxed, e.g., in the case of chloroform, of about 70° C.

In this process, the polyhydroxyalkanoate having in the molecule the 3-hydroxy-ω-alkenoic acid unit represented by Chemical Formula (28) may also be produced by a process comprising the step of culturing a microorganism in a culture medium containing at least one ω-alkenoic acid represented by Chemical Formula (29).

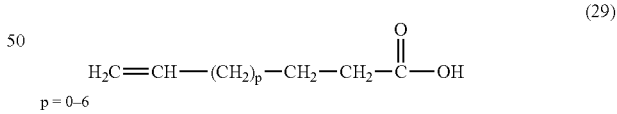
(29)

p = 0–6 wherein p may assume any one integral value within the range shown in the chemical formula.

The microorganism used in this process, the culturing of the microorganism, the production of the PHA and its accumulation in the bacterial body by the microorganism, and the collection of the PHA from the bacterial body may be the same as those in the process described previously.

The present inventors have also made extensive studies aiming at the development of a charge control agent which is highly contributory to the environmental safeguard and so forth and also has high performances. As the result, they have discovered that the polyhydroxyalkanoate described above has very good properties as a charge control agent and has a high safety to human bodies and environment, and also that a remarkable effect is brought about when a toner for developing electrostatic latent images which contains this charge control agent is used and such a toner for developing electrostatic latent images is used in an image-forming apparatus having a certain latent-image-developing system. Thus, they have accomplished the present invention.

More specifically, the present invention is a electrostatic latent image comprising the polyhydroxyalkanoate described above, and also a toner for developing electrostatic latent images which comprises the charge control agent. The present invention is further an image-forming method comprising a charging step of applying a voltage to a charging member from its outside to charge an electrostatic-latent-image-bearing member electrostatically; a developing step of developing an electrostatic latent image on the electrostatic-latent-image-bearing member by the use of the above toner for developing electrostatic latent images, to form a toner image thereon; a transfer step of transferring to a recording medium the toner image formed on the electrostatic-latent-image-bearing member, via, or not via, an intermediate transfer member; and a heat fixing step of fixing by heat the toner image held on the recording medium. The present invention is still further an image-forming apparatus having means corresponding respectively to the steps of this method, i.e., a charging means, a developing means, a transfer means and a heat fixing means.

Here, the polyhydroxyalkanoate used in the present invention has a fundamental structure as a biodegradable resin. Hence, like conventional plastic, it can be utilized in the manufacture of various products by melting, and, different from synthetic polymers derived from petroleum, has a striking property that it is broken down by microorganisms and taken into the circulation of substances in the natural world. Accordingly, it does not require any disposal by combustion, and is an effective material also from the viewpoint of the prevention of air pollution and global warming. Thus, it can be utilized as a plastic which enables environmental safeguard.

The polyhydroxyalkanoate preferable as the charge control agent, used in the toner for developing electrostatic latent images according to the present invention is specifically described below.

The charge control agent used in the present invention is a polyester resin having a 3-hydroxyalkanoate as a monomer unit, and is a polyhydroxyalkanoate having in the molecule at least one unit of units represented by Chemical Formula (1).

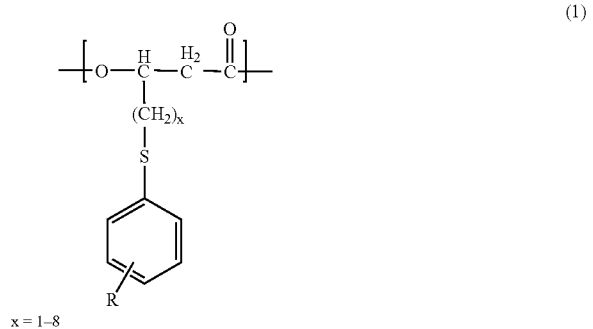

(1)

wherein R is arbitrarily selected from COOR' and SO$_2$R"; where R' is H, Na, K, CH$_3$ or C$_2$H$_5$, and R" is OH, ONa, OK, a halogen atom, OCH$_3$ or OC$_2$H$_5$; and x may assume any one integral value within the range shown in the chemical formula.

Here, where such a compound is produce by the process having the step of producing it by the aid of a microorganism, the above polyhydroxyalkanoate is an isotactic polymer of only R-configuration. As long as the object of the present invention is achievable on both aspects of physical properties and function, it need not especially be the isotactic polymer. An atactic polymer may also be used. Also, the above polyhydroxyalkanoate may also be obtained by a process having in its steps chemical synthesis utilizing, e.g., ring-opening polymerization of a lactone compound.

Examples of the process for producing the polyhydroxyalkanoate used as the charge control agent of the present invention are as described previously.

What is important in the structure of the polyhydroxyalkanoate used in the present invention is that as shown in Chemical Formula (1) it has a phenylsulfanyl structure in the side chain and has a structure in which the aromatic ring moiety has been substituted with sulfonic acid or a derivative thereof or carboxlic acid or a derivative thereof. The unit having such an anionic or electron-attracting functional group is preferable in order to more improve the negatively charging performance. In fact, the charge control agent of the present invention has a superior negatively charging performance.

The polyhydroxyalkanoate used in the present invention has a good compatibility with the binder resin. In particular, it has a very good compatibility with a polyester type binder resin. The toner incorporated with the polyhydroxyalkanoate of the present invention has a high specific charge quantity and its stability with time is also good. Hence, even after the toner has been stored over a long period of time, it can stably provide sharp images in the formation of images by electrostatic recording. It also has colorless negatively charging performance, and hence it can be employed for any of negatively chargeable black toners and color toners.

In addition, appropriate selection of the types and compositional ratio of monomer units constituting the polyhydroxyalkanoate of the present invention enables control of compatibility over a wide range. Here, the resin composition may be so selected that the charge control agent assumes a microscopically phase-separated structure in the toner binder, where the toner does not come to have any electrical continuity and hence it can stably retain electric charges. Also, the polyhydroxyalkanoate of the present invention does not contain any heavy metal. Hence, when the toner is produced by suspension polymerization or emulsification polymerization, the charge control agent does not have any polymerization inhibitory action which may be seen in heavy-metal-containing charge control agents, and hence the toner can stably be produced.

<Addition of PHA to Toner>

In the present invention, as a method of Incorporating the above compound in the toner, a method of adding it internally to toner particles and a method of adding it externally to toner particles are available. When it is internally added, it may usually be added in an amount ranging from 0.1 to 50% by weight, preferably from 0.3 to 30% by weight, and more preferably from 0.5 to 20% by weight, as weight proportion between the toner binder and the charge control agent. Its addition in an amount of less than 0.1% by weight is not preferable because the toner may not be improved in chargeability in any remarkable extent. On the other hand its addition in an amount of more than 50% by weight is not preferable from an economical viewpoint. Also, when it is externally added, it may usually be added in an amount of from 0.01 to 5% by weight as weight proportion between the toner binder and the charge control agent, and may particularly preferably be made to adhere to toner particle surfaces mechanochemically. The polyhydroxyalkanoate of the present invention may further be used in combination with any known charge control agent.

The polyhydroxyalkanoate of the present invention may usually have a number-average molecular weight of from 1,000 to 500,000, and preferably from 1,000 to 300,000. If it has a number-average molecular weight less than 1,000, it may completely dissolve in the toner binder to form a discontinuous domain with difficulty, resulting in an insufficient charge quantity and also affecting the fluidity of toner adversely. If it has a number-average molecular weight of more than 500,000, it may be dispersed in the toner with difficulty.

The molecular weight of the polyhydroxyalkanoate is measured by GPC (gel permeation chromatography). As a specific method for the measurement by GPC, the molecular weight of a sample prepared by dissolving the polyhydroxyalkanoate previously in dimethylformamide (DMF) containing 0.1% by weight of LiBr is measured through a like mobile phase, and its molecular weight distribution is determined from a calibration curve of a standard polystyrene resin.

In the present invention, as the ratio of weight-average molecular weight (Mw) to number-average molecular weight (Mw) as measure as described above, the polyhydroxyalkanoate may also have an Mw/Mn in the range of from 1 to 10, which may preferably be used.

The polyhydroxyalkanoate used in the present invention may preferably have a melting point of from 20 to 150° C., and particularly from 40 to 150° C. or, though having no melting point, may preferably have a glass transition point of from 20 to 150° C., and particularly from 40 to 150° C. If it has a melting point below 20° C., or has no melting point and has a glass transition point below 20° C., it may adversely affect the fluidity or storage stability of toner. If on the other hand it has a melting point above 150° C., or has no melting point and has a glass transition point above 150° C., the toner may be kneaded in the toner with difficulty, tending to result in a broad charge quantity distribution.

The melting point Tm and the glass transition point Tg in this case may be measured with, e.g., a differential scanning calorimeter of a highly precise, inner-heat input compensation type, such as DSC-7, manufactured by Perkin Elmer Co.

In the toner binder and toner for developing electrostatic latent images according to the present invention, the toner binder and the charge control agent may usually be in a weight proportion of from 0.1 to 50% by weight, preferably from 0.3 to 30% by weight, and more preferably from 0.5 to 20% by weight. The toner for developing electrostatic latent images according to the present invention may have a compositional proportion that usually the charge control agent is in an amount of from 0.1 to 50% by weight, the toner binder from 20 to 95% by weight, and a coloring material from 0 to 15% by weight, on the basis of toner weight. The toner may optionally contain a magnetic powder (such as a powder of a ferromagnetic metal such as iron, cobalt or nickel or a compound such as magnetite, hematite or ferrite) in an amount of 60% by weight or less so as to have also the function as a coloring material. It may further contain various additives such as a lubricant (e.g., polytetrafluoroethylene, a low-molecular weight polyolefin, a fatty acid, or a metal salt or amide thereof), and other charge control agent (e.g., a metal-containing azo dye or a salicylic acid metal salt). Also, in order to improve the fluidity of toner, a fine hydrophobic colloidal silica powder or the like may also be used. Any of these may usually be added in an amount of 10% by weight or less.

In the toner of the present invention, it is preferable that at least part of the toner binder forms a continuous domain and at least part of the charge control agent forms a discontinuous domain. Compared with a case in which the charge control agent completely dissolves in the toner binder without forming any discontinuous domain, the charge control agent added tends to come uncovered to toner particle surfaces, so that it can exhibit the intended effect in its addition in a small quantity. Also, the domains may preferably be dispersed in a particle diameter of from 0.01 to 4 µm, and more preferably from 0.05 to 2 µm. If they are dispersed in a particle diameter larger than 4 µm, they may stand dispersed insufficiently, resulting in a broad charge quantity distribution and also causing a problem that the toner may have a poor transparency. If on the other hand they are dispersed in a particle diameter smaller than 0.01 µm, they stand like the case in which the charge control agent completely dissolves in the toner binder without forming any discontinuous domain, making it necessary to add the charge control agent in a large quantity.

Whether or not at least part of the charge control agent forms a discontinuous domain and what dispersion particle diameter it has can be ascertained by observing slices of toner particles on a transmission electron microscope or the like. To observe interfaces clearly, it is also effective to dye the slices of toner particles with ruthenium tetraoxide or osmium tetraoxide and thereafter observe them on the electron microscope.

For the purpose of making small the discontinuous domain which the polyhydroxyalkanoate of the present invention forms, a polymer having compatibility with the polyhydroxyalkanoate of the present invention and having compatibility also with the toner binder may also be incorporated as a compatibilizer. The compatibilizer may include polymers in which a polymer chain containing 50 mol % or more of a monomer having substantially the same structure as the constituent monomer of the polyhydroxyalkanoate of the present invention and a polymer chain containing 50 mol % or more of a monomer having substantially the same structure as the constituent monomer of the toner binder are combined in the form of a graft or in the form of a block. The compatibilizer may usually be used in an amount of 30% by weight or less, and preferably from 1 to 10% by weight, based on the weight of the polyhydroxyalkanoate of the present invention.

<Other Materials>

Other constituent materials which constitute the toner for developing electrostatic latent images according to the present invention are described below.

(Binder Resin)

First, as the binder resin, any of those usually used when toners are produced may be used without any particular limitations. Also, before the toner is made up, the charge control agent of the present invention may previously be mixed with the binder resin so that it can be used as a toner binder composition (the toner binder) of the present invention, having a charge controlling ability. For example, the binder resin may include styrene type polymers, polyester type polymers, epoxy type polymers, polyolefin type polymers and polyurethane type polymers, any of which may be used alone or in the form of a mixture.

The styrene type polymers may include copolymers of styrene with acrylate or methacrylate and copolymers of other monomers copolymerizable with these, and copolymers of styrene with diene monomers (such as butadiene and isoprene) and copolymers of other monomers copolymerizable with these. The polyester type polymers may include polycondensation products of aromatic dicarboxylic acids with alkylene oxide addition products of aromatic diols. The epoxy type polymers may include reaction products of aromatic diols with epichlorohydrin, and modified products thereof. The polyolefin type polymers may include polyethylene, polypropylene, and copolymers of any of these with other copolymerizable monomers The polyurethane type polymers may include polyaddition products of aromatic diisocyanates with alkylene oxide addition products of aromatic diols.

As specific examples of the binder resin used in the present invention, it may include polymers of the following polymerizable monomers, or mixtures of any of these, or copolymerization products obtained using two or more of the following polymerizable monomers. Such resins may specifically include, e.g., styrene type polymers such as styrene-methacrylic acid type polymers, as well as the polyester type polymers, epoxy type polymers, polyolefin type polymers and polyurethane type polymers.

As specific examples of the polymerizable monomers, it may include, e.g., styrene; styrene derivatives such as o-methylstyrene, m-methylstyrene, p-methylstyrene, p-methoxystyrene, p-phenylstyrene, p-chlorostyrene, 3,4-dichlorostyrene, p-ethylstyrenee, 2,4-dimethylstyrene, p-n-butylstyrene, p-tert-butylstyrene, p-n-hexylstyrene, p-n-octylstyrene, p-n-nonylstyrene, p-n-decylstyrene and p-n-dodecylstyrene; ethylene unsaturated monoolefins such as ethylene, propylene, butylene and isobutylene; unsaturated polyenes such as butadiene; vinyl halides such as vinyl chloride, vinylidene chloride, vinyl bromide and vinyl fluoride; vinyl esters such as vinyl acetate, vinyl propionate and vinyl benzoate; α-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate and diethylaminoethyl methacrylate; acrylic esters such as methyl acrylate, ethyl acrylate, n-butyl-acrylate, isobutyl acrylate, propyl acrylate, n-octyl acrylate, dodecyl acrylate, 2-ethylhexyl acrylate, stearyl acrylate, 2-chloroethyl acrylate and phenyl acrylate; vinyl ethers such as methyl vinyl ether, ethyl vinyl ether and isobutyl vinyl ether; vinyl ketones such as methyl vinyl ketone, hexyl vinyl ketone and methyl isopropenyl ketone; N-vinyl compounds such as N-vinylpyrrole, N-vinylcarbazole, N-vinylindole and N-vinylpyrrolidone; vinylnaphthalenes; acrylic acid or methacrylic acid derivatives such as acrylonitrile, methacrylonitrile and acrylamide; esters of the above α,β-unsaturated acids and diesters of dibasic acids; dicaroxylic acids such as maleic acid, methyl maleate, butyl maleate, dimethyl maleate, phthalic acid, succinic-acid and terephthalic acid; polyol compounds such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A and polyoxyethylene type bisphenol A; isocyanates such as p-phenylenediisocyanate, p-xylylenediisocyanate and 1,4-tetramethylenediisocyanate; amines such as ethylamine, butylamine, ethylenediamine, 1,4-diaminobenzene, 1,4-diaminobutane and monoethanolamine; and epoxy compounds such as diglycidyl ether, ethylene glycol diglycidyl ether, bisphenol-A diglycidyl ether and hydroquinone diglycidyl ether.

(Cross-linking Agent)

When the binder resin used in the present invention is made up, a cross-linking agent as shown below may optionally be used.

For example, it may include, as bifunctional cross-linking agents, divinylbenzene, bis(4-acryloxypolyethoxyphenyl) propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates (MANDA, trade name; available from Nippon Kayaku Co., Ltd.), and the above diacrylates whose, acrylate moiety has been replaced with methacrylate.

As polyfunctional cross-linking agents it may include, e.g., pentaerythritol triacrylate, trimethylolethane triacrylate, trimethylolpropane triacrylate, tetramethylolmethane tetraacrylate, oligoester acrylate, and these compounds whose acrylate moiety has been replaced with methacrylate, and also 2,2-bis(4-methacyloxypolyethoxyphenyl)propane, diallyl phthalate, triallyl cyanurate, triallyl asocyanurate triallyl isocyanurate, triallyl trimellitate and diaryl chlorendate.

(Polymerization Initiator)

When the binder resin used in the present invention is made up, a polymerization initiator as shown below may also optionally be used.

For example, it may include di-t-butyl peroxy-2-ethylhexanoate, cumin perpivalate, t-butyl peroxylaurate, benzoyl peroxide, lauroyl peroxide, octanoyl peroxide, di-t-butyl peroxide, t-butylcumyl peroxide, dicumyl peroxide, 2,2'-azobis (2-isobutyronitrile), 2,2'-azobis(2-methylbutyronitrile), 2,2'-azobis(2,4-dimethylvaleronitrile), 2,2'-azobis(4-methoxy-2,4-dimethylvaleronitrile), 1,1-bis(t-butylperoxy)-3,3,5-trimethylcyclohexane, 1,1-bis(t-butylperoxy)cyclohexane, 1,4-bis(t-butylperoxycarbonyl)cyclohexane, 2,2-bis(t-butylperoxy)octane, n-butyl-4,4-bis(t-butylperoxy)valylate, 2,2-bis(t-butylperoxy)butane, 1,3-bis(t-butylperoxy-isopropyl)benzene, 2,5-dimethyl-2,5-di(t-butylperoxy)hexane, 2,5-dimethyl-2,5-di(t-butylperoxy)hexane, 2,5-dimethyl-2,5-di (benzoylperoxy)hexane, di-t-butyl peroxyisophthalate, 2,2-bis(4,4-di-t-butylperoxycyclohexyl)propane, di-t-butylperoxy-α-methylsuccinate, di-t-butyl peroxydimethylglutarate, di-t-butyl peroxyhexahydroterephthalate, di-t-butyl peroxyazelate, 2,5-diemthyl-2,5-di(t-butylperoxy)hexane, diethylene glycol-bis(t-butylperoxycarbonate), di-t-butyl peroxytrimethyladipate, tris(t-butylperoxy)triazine and vinyl tris(t-butylperoxy)silane. Any of these may used alone or in combination. The initiator may be used in an amount of not less than 0.05 part by weight, and preferably from 0.1 part by weight to 15 parts by weight, based on 100 parts by weight of the monomer.

(Other Biodegradable Plastic)

In the present invention, a biodegradable plastic may also preferably be used. The biodegradable plastic may include ECOSTAR and ECOSTAR PLUS (trade names; available from Hagiwara Kogyo), BIOPOLE (trade name; available from I.C.I Japan), AJICOAT (trade name; available from Ajinomoto), PLACCELL and POLYCAPROLACTONE (trade names; available from Daicell Chemical), SHOREX and BIONORE (trade names; available from Showa Denko), LACTY (trade name; available from Shimadzu Corporation), and RAYCIA (Mitsui Chemical).

In the combination of any of these resins with the charge control agent of the present invention, the polymer structure of the binder resin and the polymer structure of the polymer chain of the charge control agent may preferably be similar to each other as far as possible. If the polymer structure of the binder resin and the polymer structure of the polymer chain of the charge control agent are greatly different from each other, the charge control agent tends to be insufficiently dispersed in the binder resin.

The charge control agent of the present invention may usually internally be added to the binder resin in a weight proportion of from 0.1 to 50% by weight, preferably from 0.3 to 30% by weight, and more preferably from 0.5 to 20% by weight. Here, if the weight proportion of the charge control agent internally added is less than 0.1% by weight, a low charge quantity may result. It it is more than 50% by weight, the toner may have a poor charging stability.

<Colorant>

As the colorant that constitutes the toner for developing electrostatic latent images according to the present invention, any colorants may be used as long as they are those usually used when toners are produced. For example, carbon black, titanium white and any other all pigments and/or dyes may be used.

For example, when the toner for developing electrostatic latent images according to the present invention is used as a magnetic color toner, the colorant may include, e.g., C.I. Direct Red 1, C.I. Direct Red 2, C.I. Acid Red 1, C.I. Basic Red 1, C.I. Mordant Red 1, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4 and C.I. Basic Green 6. As the pigments, usable are chrome yellow, cadmium yellow, mineral fast yellow, navel yellow, Naphthol Yellow S, Hanza Yellow G, Permanent Yellow NCG, Tartrazine Yellow Lake, chrome orange, molybdenum orange, Permanent Orange GTR, Pyrazolone Orange, Benzidine Orange G, cadmium red, Permanent Red 4R, Watching Red calcium salt, Eosine Lake, Brilliant Carmine 3B, manganese violet, Fast Violet B, Methyl Violet Lake, Prussian blue, cobalt blue, Alkali Blue Lake, Victoria Blue Lake, Phthalocyanine Blue, Fast Sky Blue, Indanthrene Blue BC, chrome green, chromium oxide, Pigment Green B, Malachite Green Lake, Final Yellow Green G and so forth.

When the toner for developing electrostatic latent images according to the present invention is used as toners for full-color two-component developers, those shown below may be used as colorants. For example, color pigments for a magenta toner may include, C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209; C.I. Pigment Violet 1.9; and C.I. Vat Red 1, 2, 10, 13, 15, 23, 29, 35.

In the present invention, any of the pigments listed above may be used alone, or dyes may be used in combination with such pigments so that color sharpness can be improved. This is preferable in view of image quality of full-color images. Magenta dyes usable in such a case may include oil-soluble dyes such as C.I. Solvent Red 1, 3, 8, 23, 24, 25, 27, 30, 49, 81, 82, 83, 84, 100, 109, 121, C.I. Disperse Red 9, C.I. Solvent Violet 8, 13, 14, 21, 27, and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39, 40, and C.I. Basic Violet 1, 3, 7, 10, 14, 15, 21, 25, 26, 27, 28.

As other color pigments, cyan color pigments may include C.I. Pigment-Blue 2, 3, 15, 16, 17, C.I. Vat Blue 6, C.I. Acid Blue 45, or copper phthalocyanine pigments whose phthalocyanine skeleton has been substituted with 1 to 5 phthalimide methyl group(s).

Yellow color pigments may include C.I. Pigment Yellow 1, 2, 3, 4, 5, 6, 7, 10, 11, 12, 13, 14, 15, 16, 17, 23, 65, 73, 83, and C.I. vat Yellow 1, 3, 20.

The dyes and pigments as described above may each be used alone. Otherwise, any of them may arbitrarily be mixed and then used, in order to obtain the desired color tone of toners. Taking account of the environmental conservation and the safety to human bodies, food dyes of various types may preferably be used.

The content of the above colorant in the toner may be changed in a wide range in accordance with the desired coloring effect and so forth. Usually, in order to attain the best toner characteristics, i.e., taking account of coloring power for printing, shape stability of toner particles, toner scattering and so forth, any of these colorants may usually be used in an amount of from 0.1 to 60 parts by weight, and preferably from 0.5 to 20 parts by weight, based on 100 parts by weight of the binder resin.

<Other Components of Toner>

In the toner for developing electrostatic latent images according to the present invention, in addition to the binder resin and colorant components described above, the following compounds may be added as long as they do not adversely influence the effect of the present invention (i.e., in the proportion smaller than the content of the binder resin component). Such compounds are exemplified by silicone resin, polyester, polyurethane, polyamide, epoxy resin, polyvinyl butyral, rosin, modified rosin, terpene resin, phenolic resin, aliphatic hydrocarbon resin such as low-molecular weight polyethylene or low-molecular weight polypropylene or alicyclic hydrocarbon resin, aromatic petroleum resin and chlorinated paraffin or paraffin wax. Waxes preferably usable among these may specifically include low-molecular weight polypropylene and by-products thereof, low-molecular weight polyester, ester waxes, and aliphatic derivatives. Waxes obtained from these waxes by fractionating the waxes by various methods may also preferably be used. Also, after the fractionation, the waxes may be subjected to oxidation, block copolymerization or graft modification.

In the toner for developing electrostatic latent images according to the present invention, a toner having superior performance can be obtained especially when it contains the above wax component and such a wax component stands dispersed in the binder resin in the form of spherical and/or spindle-shaped islands in its cross-sectional observation of toner particles using a transmission electron microscope (TEM).

<Toner Production Process>

As a specific process for producing the toner for developing electrostatic latent images according to the present invention, constituted as described above, any conventionally known process may be used. The toner for developing electrostatic latent images according to the present invention may be produced by, e.g., what is called a pulverization process, which produces the toner according to the following steps. That is, stated specifically, the polyhydroxyalkanoate, resins such as the binder resin, and other components such as the wax optionally added are thoroughly mixed by means of a mixing machine such as a Henschel mixer or a ball mill, and then the mixture is melt-kneaded using a heat kneading machine such as a heating roll, a kneader or an extruder to make the resin and so on melt one another, in which the pigment, dye or magnetic material as the colorant and additives such as a metal compound optionally added are then dispersed or dissolved, followed by cooling for solidification. Thereafter, the solidified product is pulverizes by means of a grinding machine such as a jet mill or a ball mill, followed by classification. Thus, the toner for developing electrostatic latent images according to the present invention, having the desired particle diameter, can be obtained. Incidentally, in the step of classification, a multi-division classifier may preferably be used in view of production efficiency.

The toner for developing electrostatic latent images according to the present invention, having the desired particle diameter, may also be obtained by mixing the binder resin and the polyhydrokyalkanoate in the form of a solution using a solvent (including, aromatic hydrocarbons such as toluene and xylene; halogenated products such as chloroform and ethylene dichloride, ketones such as acetone and methyl ethyl ketone, and amides such as dimethylformamide), stirring the solution, and thereafter introducing the resultant solution into water to effect reprecipitation, followed by filtration and then drying, and thereafter pulverizing the solidified product by means of a grinding machine such as a jet mill or a ball mill, followed by classification. Incidentally, in the step of classification, a multi-division classifier may preferably be used in view of production efficiency.

The toner for developing electrostatic latent images according to the present invention may still also be produced by what is called a polymerization process as described below. That is, in this case, materials such as the polyhydroxyalkanoate, the polymerizable monomer, the pigment, dye or magnetic material as the colorant, and optionally the cross-linking agent, the polymerization initiator, the wax and other additives are mixed and dispersed to prepare a polymerizable monomer composition, which is then subjected to suspension polymerization in an aqueous dispersion medium to synthesize polymerized color resin particles. The resin particles thus obtained are solid-liquid separated, followed by drying and then optionally classification to obtain the toner for developing electrostatic-latent images according to the present invention.

As another method, colored fine particles not containing any charge control agent may be prepared by the above process, and then the polyhydroxyalkanoate may be added thereto alone, or together with an external additive such as colloidal silica, by a mechanochemical method to cause the latter to adhere to the former's particle surfaces.

(Silica External Additive)

In the present invention, to the toner produced by the process as described above, it is preferable to add a fine silica powder in order to improve toner's charging stability, fluidity and running performance. As the fine silica powder used here, a fine silica powder having a specific surface area of 20 $m^2/g$ or more, and particularly in the range of from 30 to –400 $m^2/g$, as measured by nitrogen adsorption according to the BET method, gives good results. In this case, the fine silica powder may be used in an amount of from 0.01 to 8 parts by weight, and preferably from 0.1 to 5 parts by weight, based on 100 parts by weight of the toner particles. For the purpose of making hydrophobic and controlling chargeability, the fine silica powder used here may preferably optionally be treated with a treating agent such as a silicone varnish, a modified silicone varnish of various types, a silicone oil, a modified silicone oil of various types, a silane coupling agent, a silane coupling agent having a functional group or other organosilicon compound. Use of such a treated powder is preferred. Any of these treating agents may be used in the form of a mixture.

(Inorganic Powder)

In order to improve toner's developing performance and running performance, it is also preferable to add the following inorganic powder. It may include, e.g., oxides of metals such as magnesium, zinc, aluminum, cerium, cobalt, iron, zirconium, chromium, manganese, strontium, tin and antimony; composite metal oxides such as calcium titanate, magnesium titanate and strontium titanate; metal salts such as calcium carbonate, magnesium carbonate and aluminum carbonate; clay minerals such as kaolin; phosphoric acid compounds such as apatite; silicon compounds such as silicon carbide and silicon nitride; and carbon powders such as carbon black and graphite powder. In particular, fine powder of zinc oxide, aluminum oxide, cobalt oxide, manganese dioxide, strontium titanate or magnesium titanate may preferably be used.

(Lubricant)

A lubricant powder as shown below may also be added to the toner. It may include, e.g., fluorine resins such as Teflon and polyvinylidene fluoride; fluorine compounds such as carbon fluoride; fatty acid metal salts such as zinc stearate; fatty acids, and fatty acid derivatives such as fatty esters; and molybdenum sulfide.

<Carrier>

The toner for developing electrostatic latent images according to the present invention, constituted as described above, may be used alone as a non-magnetic one-component developer, or may be applied to conventionally known various toners such as a non-magnetic toner which constitutes a magnetic two-component developer together with a magnetic carrier, and a magnetic toner used alone as a magnetic one-component developer. Here, as a carrier used in two-component development, any of conventionally known carriers may be used. Stated specifically, particles formed of metals such as iron, nickel, cobalt, manganese, chromium and rare earth elements, and alloys or oxides thereof, having been surface-oxidized or unoxidized and having an average particle diameter of from 20 to 300 μm, may be used. Also, it is preferable to use carriers comprising such carrier particles to or on the surfaces of which a material such as a styrene resin, an acrylic resin, a silicone resin, a fluorine resin or a polyester resin has been made to adhere or coated.

<Magnetic Toner>

The toner for developing electrostatic latent images according to the present invention may also be made usable as a magnetic toner by incorporating a magnetic material into toner particles. In this case, the magnetic material may also be made to serve as the colorant. The magnetic material used here may include iron oxides such as magnetite, hematite and ferrite; magnetic metals such as iron, cobalt and nickel, or alloys of any of these metals with a metal such as aluminum, cobalt, copper, lead, magnesium, tin, zinc, antimony, beryllium, bismuth, cadmium, calcium, manganese, selenium, titanium, tungsten or vanadium, and mixtures of any of these. As these magnetic material usable in the present invention, those having an average particle diameter of from 2 μm or less, and preferably approximately from 0.1 to 0.5 μm, are preferred. As its quantity in which it is incorporated in the toner, it may preferably be used in an amount of from 20 to 200 parts by weight based on 100 parts by weight of the binder resin, and particularly in an amount of from 40 to 150 parts by weight based on 100 parts by weight of the binder resin.

In order to achieve much higher image quality, it must be made possible to develop finer latent image dots faithfully. For that end, it is preferable that, e.g., the toner for developing electrostatic latent images according to the present invention has toner particles so regulated as to have a weight-average particle diameter of from 4 µm to 9 µm Namely, toner particles having a weight-average particle diameter smaller than 4 µm are not preferable because they may cause a lowering of transfer efficiency and hence transfer residual toner tends to remain on the photosensitive member in a large quantity, tending to cause non-uniform or uneven images due to fog and faulty transfer. Also, toner particles having a weight-average particle diameter larger than 9 µm tend to cause spots around characters or line images.

In the present invention, the average particle diameter and particle size distribution of the toner are measured with a Coulter counter Model TA-II or Coulter Multisizer (manufactured by Coulter Electronics, Inc.). An interface (manufactured by Nikkaki k.k.) that outputs number distribution and volume distribution and a personal computer PC9801 (manufactured by NEC) are connected. As an electrolytic solution used in the measurement, an aqueous 1% NaCl solution is prepared using first-grade sodium chloride. For example, commercially available, ISOTON R-II (available from Coulter Scientific Japan Co.) may be used. As a specific method, measurement is made by adding as a dispersant from 0.1 to 5 mL of a surface active agent (preferably an alkylbenzene sulfonate) to from 100 to 150 ml of the above aqueous electrolytic solution, and further adding from 2 to 20 mg of a sample to be measured. The electrolytic solution in which the sample has been suspended is subjected to dispersion for about 1 minute to about 3 minutes in an ultrasonic dispersion machine. The volume distribution and number distribution are calculated by measuring the volume and number of toner particles with particle diameters of not smaller than 2 µm by means of the above Coulter counter Model TA-II, using an aperture of 100 µm as its aperture. Then the values according to the present invention are determined, which are the volume-based, weight-average particle diameter (D4) determined from the volume distribution and the number-based, number-average particle diameter (D1) determined from number distribution.

<Charge Quantity>

The toner for developing electrostatic latent images according to the present invention may preferably have a charge quantity (two-component method) per unit weight, of from −10 to −80 µC/g, and more preferably from −15 to −70 µC/g. This is preferable in order to improve transfer efficiency in a transfer method making use of a transfer member to which a voltage is kept applied.

Figure 26:
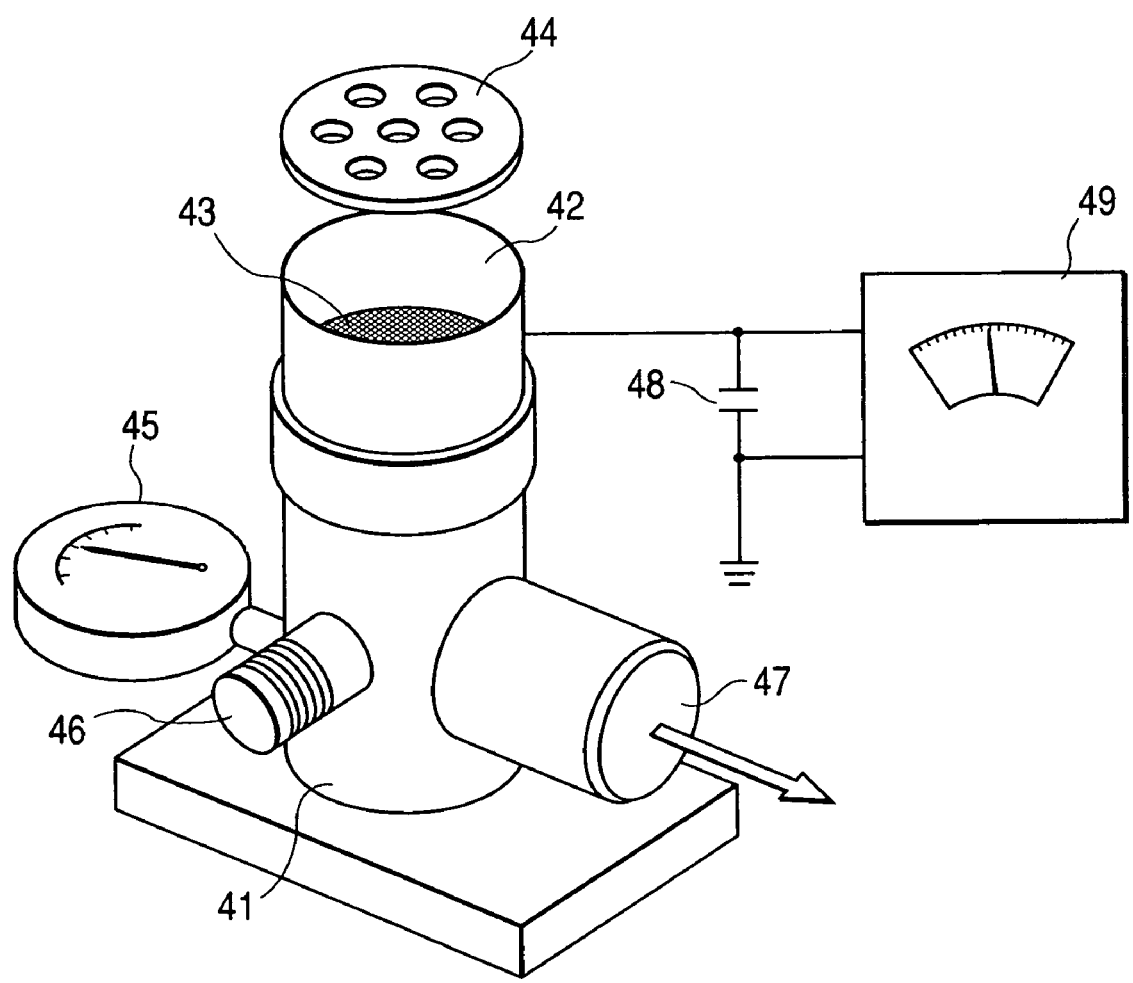
FIG. 26 is a perspective view of a device for measuring the quantity of triboelectricity of toners, used in the present invention.

A method of measuring the charge quantity quantity (two-component triboelectricity) by the two-component method used in the present invention is described below. In the measurement, a charge quantity measuring device shown in FIG. 26 is used.

First, in a fixed environment and using an iron powder EFV200/300 (available from Powder Teck Co.) as the carrier, a mixture prepared by adding 0.5 g of the measuring-object toner to 9.5 g of the carrier is put in a bottle with a volume of 50 to 100 mL, made of polyethylene, and is set on a shaker having a fixed shaking width, followed by shaking for a fixed time, setting shaking conditions at a shaking width of 100 mm and a shaking speed of 100 to-and-fro times per minute. Then, the resulting mixture is put in a measuring container 42 made of a metal at the bottom of which a screen 43 of 500 meshes is provided, and the container is covered with a plate 44 made of a metal. The total weight of the measuring container 42 at this time is weighed and is expressed as W1 (g). Next, in a suction device (not shown; made of an insulating material at least at the part coming into contact with the measuring container 42), air is sucked from a suction opening 47 and an air-flow control valve 46 is operated to control the pressure indicated by a vacuum indicator 45 to be 2,450 Pa (250 mmAq). In this state, suction is carried out for 1 minute to remove the toner by suction. The potential indicated by a potentiometer 49 at this time is expressed as V (volt). Herein, numeral 48 denotes a capacitor, whose capacitance is expressed as C (µF). The total weight of the measuring container after completion of the suction is also weighed and is expressed as W2 (g). The quantity of triboelectricity (µC/g) of the toner is calculated from these measured values according to the following expression.

Quantity of triboelectricity (µC/g)=$C \times V/(W1-W2)$

<Molecular Weight Distribution of Binder Resin>

The binder resin used as a constituent material of the toner for developing electrostatic latent images according to the present invention may preferably be made to have, in its molecular weight distribution as measured by GPC, a peak in the range of from 3,000 to 150,000 in the low-molecular weight region especially when the toner is produced by pulverization. Namely, if the binder resin has the GPC peak at more than 150,000 in the low-molecular weight region, it may be difficult to obtain a toner improved sufficiently in transfer efficiency. Also, the use of a binder resin having the GPC peak at less than 3,000 in the low-molecular weight region is not preferable because it tends to cause melt adhesion when toner particles are surface-treated.

In the present invention, the molecular weight of the binder resin is measured by GPC (gel permeation chromatography). As a specific method for measurement by GPC, a sample obtained by beforehand subjecting the toner to extraction with a THF (tetrahydrofuran) solvent for 20 hours by means of a Soxhlet extractor is used for the measurement. As column constitution, A-801, A-802, A-803, A-804, A-805, A-806 and A-807, available from Showa Denko K.K., are connected, and the molecular weight distribution is measured using a calibration curve of standard polystyrene resin.

In the present invention, it is also preferable to use as the binder resin a binder resin having a ratio of weight-average molecular weight (Mw) to number-average molecular weight (Mn), Mw/Mn, of from 2 to 100, as measured in the manner as described above.

<Glass Transition Point of Toner>

It is further preferable for the toner of the present invention to be so prepared as to have a glass transition point Tg of from 40° C. to 75° C., and more preferably from 52° C. to 70° C., in view of fixing performance and storage stability The glass transition point Tg in this case may be measured with, e.g., a differential scanning calorimeter of a highly precise, inner-heat input compensation type, such as DSC-7, manufactured by Perkin Elmer Co. It is measured according to ASTM D3418-82. In the present invention, a measuring sample is once heated to take a previous history and thereafter cooled rapidly. Then, the sample is again heated at a heating rate of 10° C./min. within the temperature range of 0 to 200° C., where the DSC curve thus measured may be used.

<Image-forming Method>

The toner for developing electrostatic latent images according to the present invention, constituted as described above, may particularly preferably be applied to;

an image-forming method having at least a charging step of applying a voltage to a charging member from its outside to charge an electrostatic-latent-image-bearing member electrostatically; a latent-image-forming step of forming an electrostatic latent image on the electrostatic-latent-image-bearing member thus charged; a developing step of developing the electrostatic latent image by the use of a toner to form a toner image on the electrostatic-latent-image-bearing member; a transfer step of transferring to a recording medium the toner image formed on the electrostatic-latent-image-bearing member; and a heat fixing step of fixing by heat the toner image held on the recording medium; or an image-forming method in which the transfer step comprises a first transfer step of transferring to an intermediate transfer member the toner image formed on the electrostatic-latent-image-bearing member and a second transfer step of transferring to a recording medium the toner image held on the intermediate transfer member.

Examples are given below. In the following, "%" is by weight unless particularly noted.

EXAMPLES

First, PHA producing microorganism was cultured in the medium containing 5-thiophenoxy valeric acid to produce PHA mainly containing 3-hydroxy-5-thiophenoxy valeric unit (Example 1 to 9).

Example 1

In 200 mL of M9 medium containing 0.5% of polypeptone and 0.1% of 5-thiophenoxy valeric acid, the YN2 strain was inoculated to effect shaking culture in a 500 mL shaking flask under condition of 30° C. After 30 hours, the bacterial body was collected by centrifugation, and then washed with methanol, followed by freeze-drying. The resultant freeze-dried pellets were weighed. Acetone was added to the dried pellets to extract a polymer and the liquid was stirred at room temperature (23° C.) for 72 hours. The acetone extract obtained was filtered and thereafter concentrated by means of rotary evaporator. The concentrated liquid was re-precipitated with cold methanol, and further only the precipitate formed was collected followed by vacuum drying to obtain an objective PHA. The freeze-dried pellets' weight was 215 mg and the weight of the obtained polymer was 76 mg.

The molecular weight of this PHA was also measured by gel permeation chromatography (GPC: Toso HLC-8220; column: Toso TSK-GEL Super HM-H; solvent: chloroform; in terms of polystyrene). As the result, it had Mn (number-average molecular weight) of 150,000 and Mw (weight-average molecular weight) of 390,000.

Figure 2:
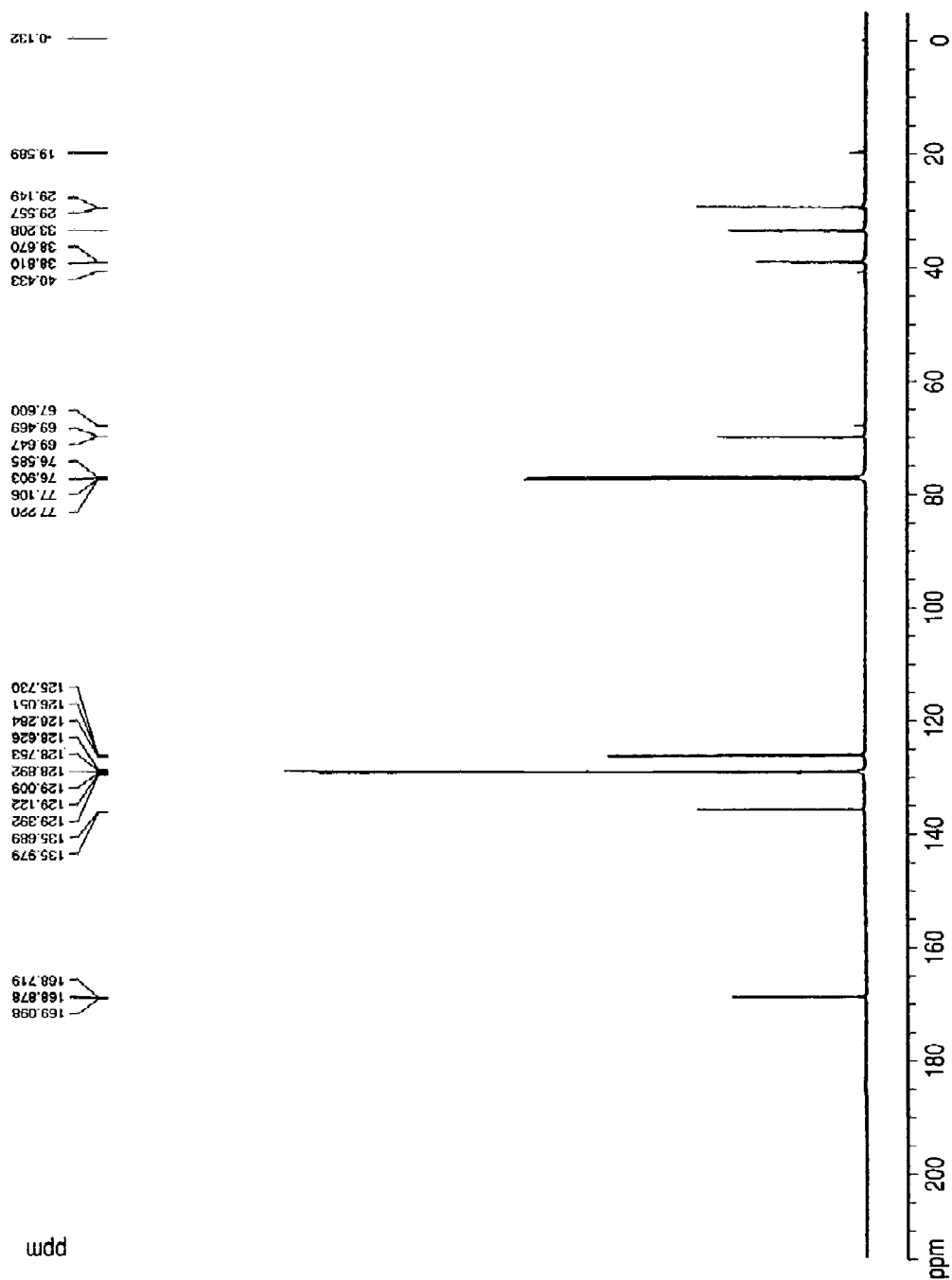
FIG. 2 is a $^{13}$C-NMR spectrum chart of a polymer obtained according to Example 1.

The structure of the obtained polymer was determined by $^1$H-NMR and $^{13}$C-NMR (FT-NMR: Bruker DPX400; $^1$H resonance frequency: 400 MHz; measurement nuclide: $^1$H and $^{13}$C; used solvent: CDCl$_3$; reference: capillary enclosed TMS/CDCl$_3$; measurement temperature: room temperature). The spectrum charts by $^1$H-NMR and $^{13}$C-NMR are shown in FIG. 1 and FIG. 2. The assignment of hydrogen atoms shown in chemical formula (30) giving resonance signals in $^1$H-NMR spectrums are shown in Table 1, and the assignment of carbon atoms giving resonance signals in $^{13}$C-NMR spectrums are shown in Table 2.

TABLE 1

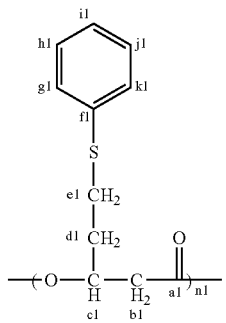

(30)

$^1$H-NMR assignment result

| ppm | Integrated value | Split | Assignment |
|---|---|---|---|
| 1.89 | 2H | m | d1 |
| 2.41-2.56 | 2H | m | b1 |
| 2.80-2.91 | 2H | m | e1 |
| 5.25 | 1H | m | c1 |
| 7.12 | 1H | m | i1 |
| 7.20-7.46 | 4H | m | g1, h1, j1, k1 |

TABLE 2

$^{13}$C-NMR assignment result

| ppm | Split | Assignment |
|---|---|---|
| 29.1 | s | e1 |
| 33.2 | s | d1 |
| 38.7 | s | b1 |
| 69.6 | s | c1 |
| 126.1 | s | i1 |
| 128.8 | s | h1, j1 |
| 129.1 | s | g1, k1 |
| 135.8 | s | f1 |
| 168.9 | s | a1 |

As a result of the assignment of $^1$H-NMR, the obtained PHA contained 3-hydroxy-5-thiophenoxy valeric acid unit at a content of at least 93% or more.

Example 2

In 200 mL of M9 medium containing 0.5% of glucose and 0.05% of 5-thiophenoxy valeric acid, the YN2 strain was inoculated to effect shaking culture in 500 mL flask at 30° C. After 45 hours, the bacterial body was collected by centrifugation and then transferred to M9 medium containing 0.5% of glucose and 0.05% of 5-thiophenoxy valeric acid and not containing NH$_4$Cl, and then cultured at 30° C. After 48 hours, the bacterial body was collected by centrifugation and then washed with methanol, followed by freeze-drying. The resultant freeze-dried pellets were weighed. Chloroform was added to the dried pellets to extract a PHA at 60° C. for 24 hours. The chloroform extract obtained was filtered and thereafter concentrated by means of rotary evaporator. The concentrated liquid was re-precipitated with cold methanol, and further only the precipitate formed was collected followed by vacuum drying to obtain an objective PHA. The freeze-dried pellets' weight was 400 mg and the weight of the polymer was 220 mg.

The molecular weight of this PHA was also measured by gel permeation chromatography (GPC: Toso HLC-8220; column: Toso TSK-GEL Super HM-H; solvent: chloroform; in terms of polystyrene). As the result, it had Mn of 170,000 and Mw of 560,000.

The structure of the obtained polymer was determined by $^1$H-NMR (FT-NMR: Bruker DPX400; $^1$H resonance frequency: 400 MHz; measurement nuclide: $^1$H; used solvent: CDCl$_3$; reference: capillary enclosed TMS/CDCl$_3$; measurement temperature: room temperature).

As a result, the obtained PHA contained 3-hydroxy-5-thiophenoxy valeric acid unit at a content of at least 84% or more.

Example 3

Figure 3:
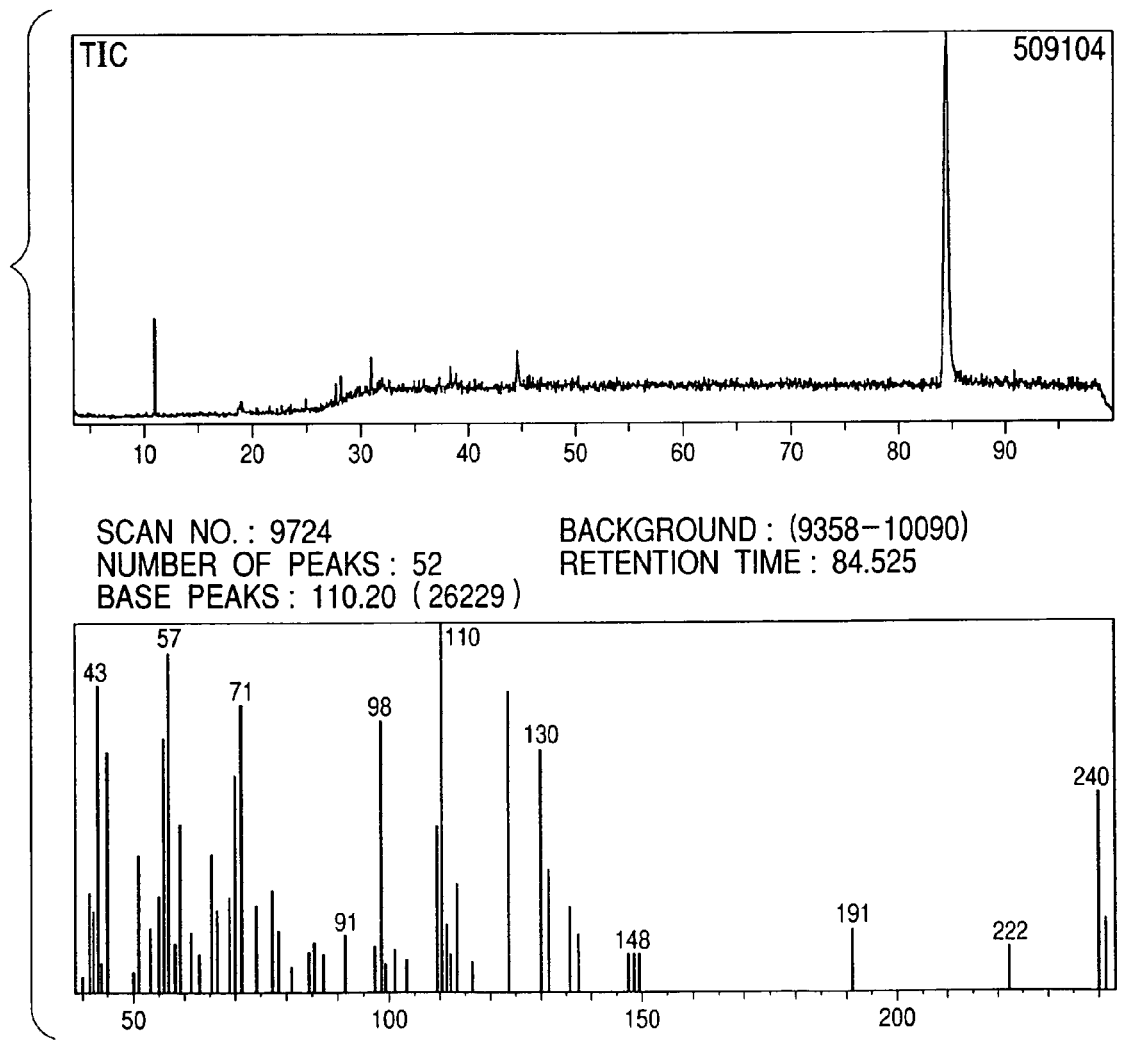
FIG. 3 is a MS spectrum of methyl-esterified product of the PHA monomer unit according to Example 3.

A polymer was obtained in the same manner as in Example 1 except that strain H45 was used as a bacteria. The freeze-dried pellets' weight was 180 mg and the weight of the polymer was 78 mg. 10 mg of obtained polymer was dissolved in 2 mL of chloroform, and then 2 mL of methanol containing 3% of sulfuric acid was added, and the liquid was subjected to methanolysis at 100° C. for 3.5 hours with reflux. After the reaction, distilled water was added to the liquid and stirred, and organic layer was dehydrated by anhydrous-magnesium sulfate. The resultant was analyzed by gas chromatography mass spectrometer (GC-MS; Shimadzu QP-5050A; column: DB-WAXETR (J&W); column temperature: rise 80° C. to 200° C. by 5° C./min; injection and interface temperature: 230° C.). The Total Ion Chromatograph (TIC) and mass spectrum are shown in FIG. 3. The mass spectrum of the peak around 85 minute confirmed that the peak shows 3-hydroxy-5-thiophenoxy valeric acid methyl ester. Other peaks due to polyhydroxyalkanoate was only 3-hydroxy valeric acid methyl ester around 11 minute, and the content of 3-hydroxy-5-thiophenoxy valeric acid methyl ester was 97%.

Example 4

Figure 4:
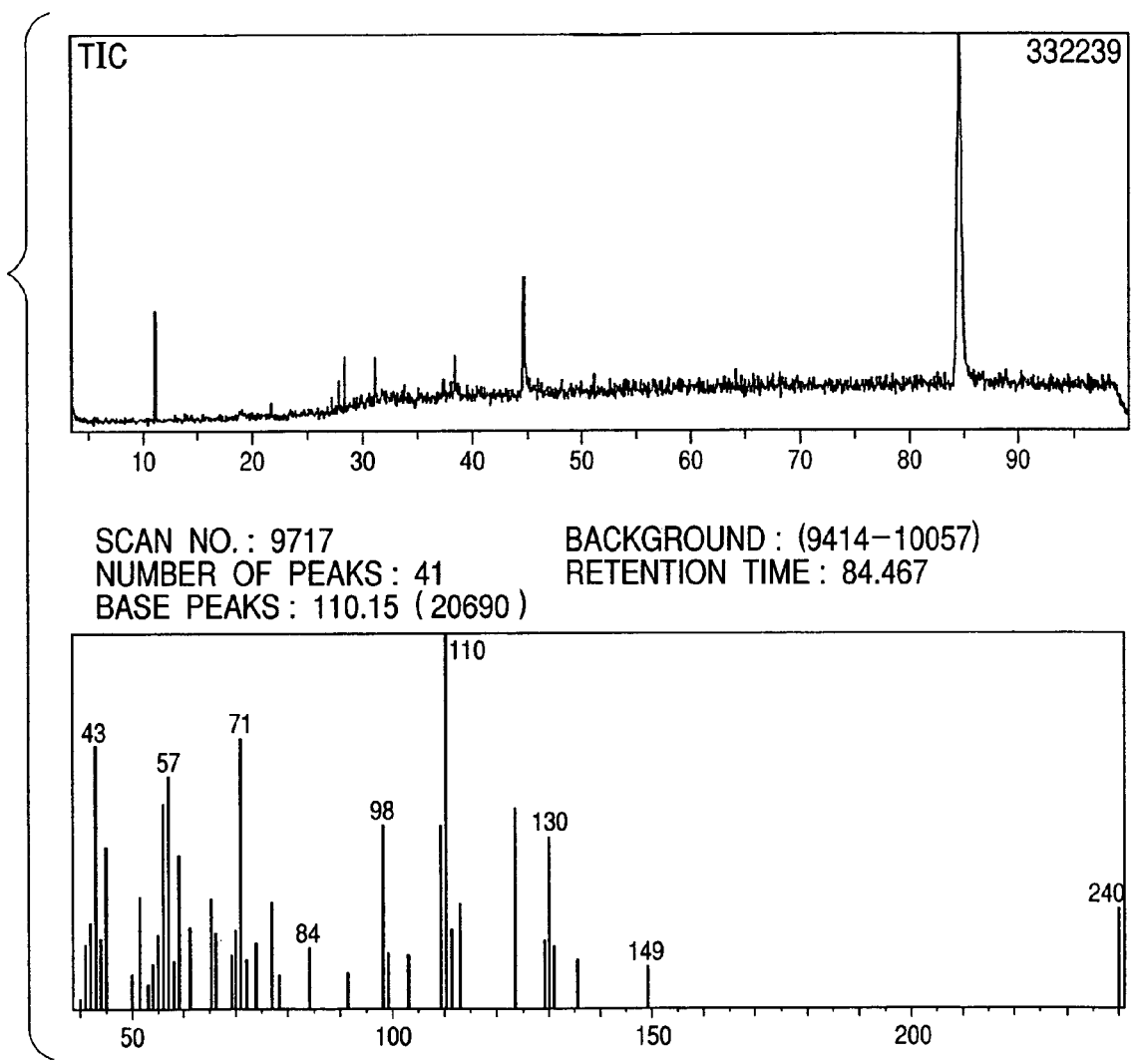
FIG. 4 is a MS spectrum of methyl-esterified product of the PHA monomer unit according to Example 4.

A polymer was obtained in the same manner as in Example 1 except that strain P161 was used as a bacteria. The freeze-dried pellets' weight was 160 mg and the weight of the polymer was 69 mg. 10 mg of obtained polymer was dissolved in 2 mL of chloroform, and then 2 mL of methanol containing 3% of sulfuric acid was added, and the liquid was subjected to methanolysis at 100° C for 3.5 hours with reflux. After the reaction, distilled water was added to the liquid and stirred, and organic layer was dehydrated by anhydrous magnesium sulfate. The resultant was analyzed by gas chromatography mass spectrometer (GC-MS; Shimadzu QP-5050A; column: DB-WAXETR (J&W); column temperature: rise 80° C. to 200° C. by 5° C./min; injection and interface temperature: 230° C.). The Total Ion Chromatograph (TIC) and mass spectrum are shown in FIG. 4. The mass spectrum of the peak around 85 minute confirmed that the peak shows 3-hydroxy-5-thiophenoxy valeric acid methyl ester. Other peaks due to polyhydroxyalkanoate was only 3-hydroxy valeric acid methyl ester around 11 minute, and the content of 3-hydroxy-5-thiophenoxy valeric acid methyl ester was 95%.

Example 5

In 200 mL of M9 medium containing 0.5% of glucose and 0.1% of 5-thiophenoxy valeric acid, 1 mL of culture solution containing YN2 strain, which was cultured in M9 medium containing 0.5% polypeptone for 20 hours, inoculated to effect shaking culture in a 500 mL shaking flask under condition of 30° C. After 24 hours, the bacterial body was collected by centrifugation and then transferred to M9 medium containing 0.5% of glycerol and 0.1% of 5-thiophenoxy valeric acid and not containing NH$_4$Cl, and then cultured at 30° C. After 23 hours, the bacterial body was collected by centrifugation and then washed with methanol, followed by freeze-drying. The resultant freeze-dried pellets were weighed. Chloroform was added to the dried pellets to extract a polymer at 60° C. for 24 hours. The chloroform extract obtained was filtered and thereafter concentrated by means of rotary evaporator. The concentrated liquid was re-precipitated with cold methanol, and further only the precipitate formed was collected followed by vacuum drying to obtain an objective polymer. The freeze-dried pellets' weight was 267 mg and the weight of the polymer was 191 mg.

The molecular weight of this polymer was measured by gel permeation chromatography (GPC: Toso HLC-8220; column: Toso TSK-GEL Super HM-H; solvent: chloroform; in terms of polystyrene). As the result, it had Mn of 80,000 and Mw of 220,000.

Figure 5:
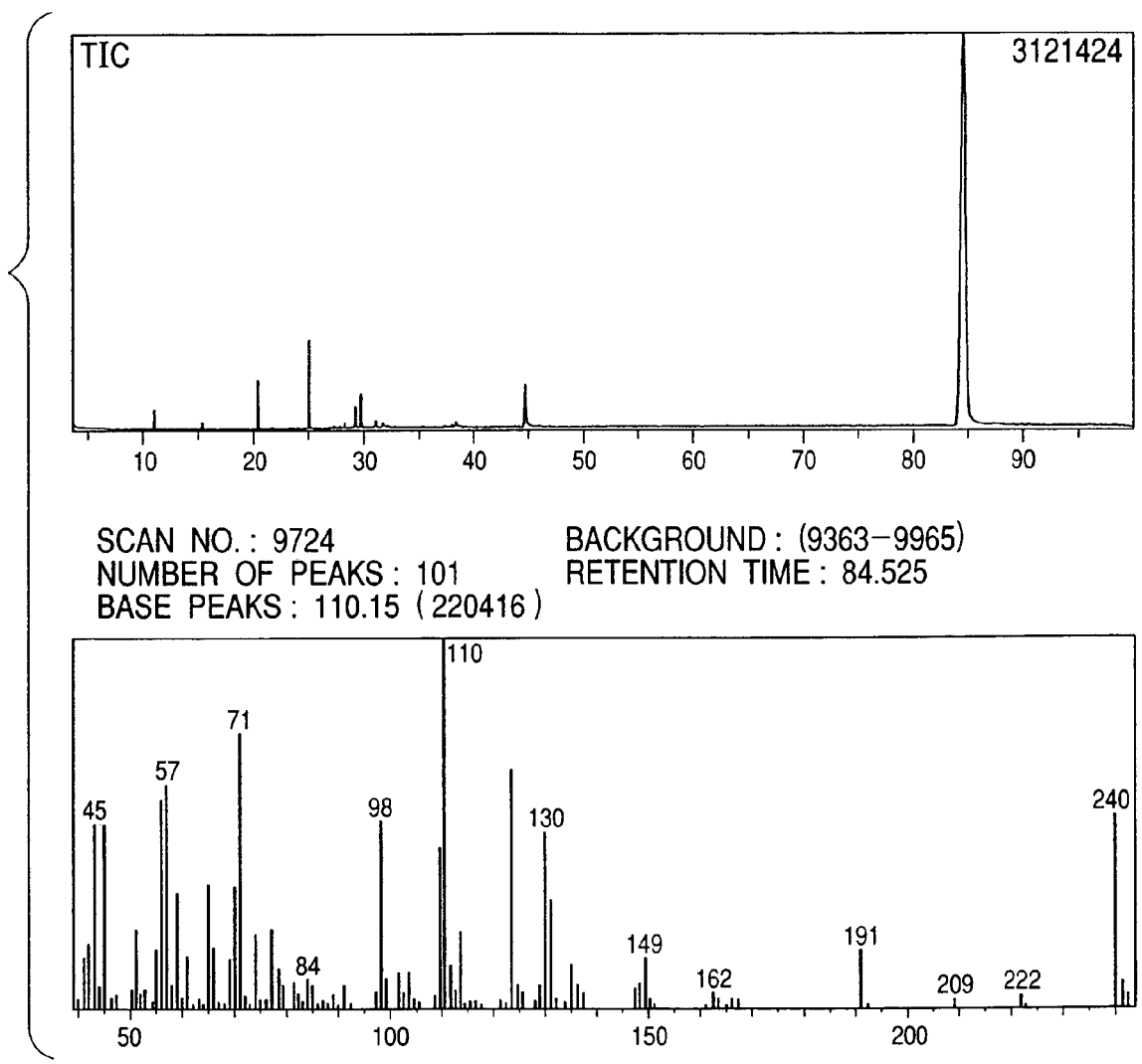
FIG. 5 is a MS spectrum of methyl-esterified product of the PHA monomer unit according to Example 5.

10 mg of obtained polymer was dissolved in 2 mL of chloroform, and then 2 mL of methanol-containing 3% of sulfuric acid was added, and the liquid was subjected to methanolysis at 100° C. for 3.5 hours with reflux. After the reaction, distilled water was added to the liquid and stirred, and organic layer was dehydrated by anhydrous magnesium sulfate. The resultant was analyzed by gas chromatography mass spectrometer (GC-MS; Shimadzu QP-5050A; column: DB-WAXETR (J&W); column temperature: rise 80° C. to 200° C. by 5° C./min; injection and interface temperature: 230° C.). The Total Ion Chromatograph (TIC) and mass spectrum are shown in FIG. 5. The mass spectrum of the peak around 85 minute confirmed that the peak shows 3-hydroxy-5-thiophenoxy valeric acid methyl ester. The content of other units including 3-hydroxy alkane acid methyl ester were derived from the area of TIC peaks. The results are shown in Table 3.

TABLE 3

| | |
|---|---|
| 3-Hydroxybutyric acid | 0.5% |
| 3-Hydroxyhexanoic acid | 0.1% |
| 3-Hydroxyoctanoic acid | 1.1% |
| 3-Hydroxydecanoic acid | 2.1% |
| 3-Hydroxyundecanoic acid | 0.4% |
| 3-Hydroxyundecenoic acid | 0.9% |
| 3-Hydroxy-5-Thiophenoxy valeric acid | 94.9% |

Example 6

An objective polymer was obtained in the same manner as in Example 5 except that sodium malate was used instead of glycerol. The freeze-dried pellets' weight was 298 mg and the weight of the polymer was 215 mg.

Figure 6:
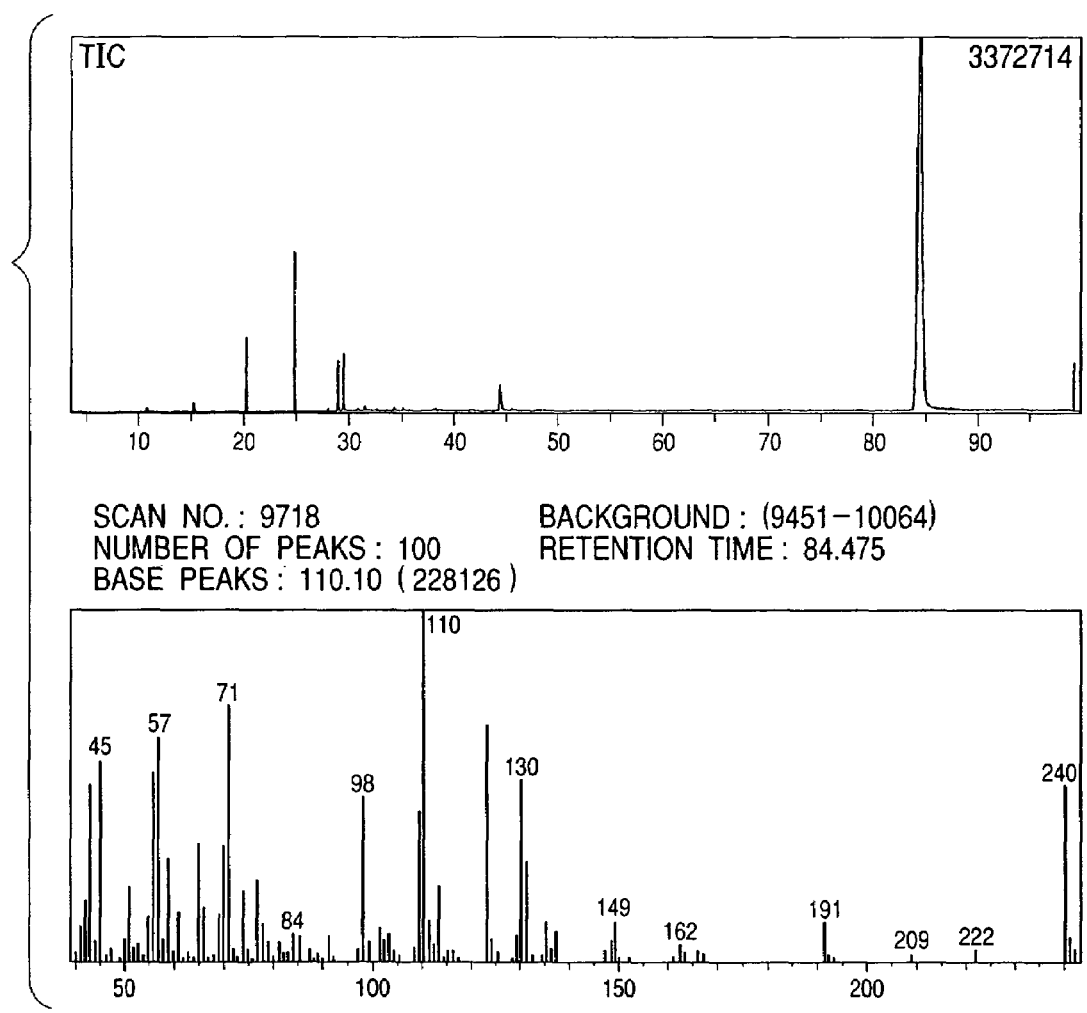
FIG. 6 is a MS spectrum of methyl-esterified product of the PHA monomer unit according to Example 6.

The molecular weight of this polymer was measured by GPC in the sane manner. As the result, it had Mn of 180,000 and Mw of 550,000. The obtained polymer was further analyzed by GC-MS in the same manner as in Example 5. The Total Ion Chromatograph (TIC) and mass spectrum are shown in FIG. 6. The mass spectrum of the peak around 85 minute confirmed that the peak shows 3-hydroxy-5-thiophenoxy valeric acid methyl ester. The content of other units including 3-hydroxy alkane acid methyl ester were derived from the area of TIC peaks. The results are shown in Table 4.

TABLE 4

| | |
|---|---|
| 3-Hydroxybutyric acid | 0.1% |
| 3-Hydroxyhexanoic acid | 0.2% |
| 3-Hydroxyoctanoic acid | 1.8% |
| 3-Hydroxydecanoic acid | 3.9% |
| 3-Hydroxyundecanoic acid | 1.3% |
| 3-Hydroxyundecenoic acid | 1.7% |
| 3-Hydroxy-5-Thiophenoxy valeric acid | 91.0% |

Example 7

An objective polymer was obtained in the same manner as in Example 5 except that sodium lactate was used instead of glycerol. The dried pellets' weight was 430 mg and the weight of the polymer was 298 mg.

The molecular weight of this polymer was measured by GPC in the same manner. As the result, it had Mn of 130,000 and Mw of 430,000.

Figure 7:
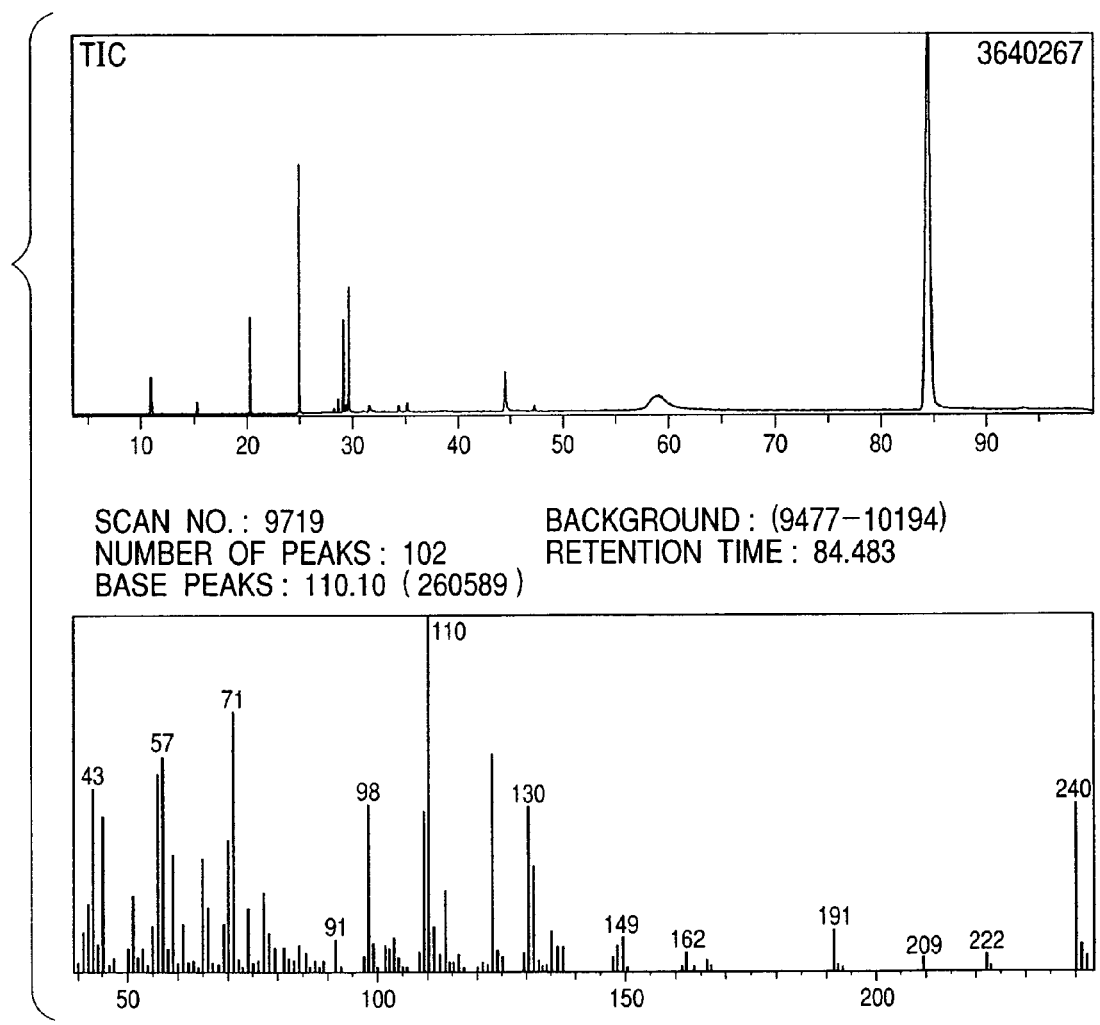
FIG. 7 is a MS spectrum of methyl-esterified product of the PHA monomer unit according to Example 7.

The obtained polymer was further analyzed by GC-MS in the same manner as in Example 5. The Total Ion Chromatograph (TIC) and mass spectrum are shown in FIG. 7. The mass spectrum of the peak around 85 minute confirmed that the peak shows 3-hydroxy-5-thiophenoxy valeric acid methyl ester. The content of other units including 3-hydroxy alkane acid methyl ester were derived from the area of TIC peaks. The results are shown in Table 5.

TABLE 5

| | |
|---|---|
| 3-Hydroxybutyric acid | 0.8% |
| 3-Hydroxyhexanoic acid | 0.2% |
| 3-Hydroxyoctanoic acid | 2.1% |
| 3-Hydroxydecanoic acid | 5.7% |
| 3-Hydroxyundecanoic acid | 2.3% |
| 3-Hydroxyundecenoic acid | 3.1% |
| 3-Hydroxy-5-Thiophenoxy valeric acid | 85.8% |

Example 8

In 200 mL of M9 medium containing 0.5% of yeast extract (DIFCO) and 0.1% of 5-thiophenoxy valeric acid, the YN2 strain was inoculated to effect shaking culture in a 500 mL shaking flask under condition of 30° C. After 21 hours, the bacterial body was collected by centrifugation, and then washed with methanol, followed by freeze-drying. The resultant freeze-dried pellets were weighed. Acetone was added to the dried pellets to extract a polymer and the liquid was stirred at room temperature (23° C.) for 72 hours. The acetone extract obtained was filtered and thereafter concentrated by means of rotary evaporator. The concentrated liquid was re-precipitated with cold methanol, and further only the precipitate formed was collected followed by vacuum drying to obtain an objective polymer. The freeze-dried pellets' weight was 255 mg and the weight of the polymer was 40 mg. The molecular weight of this polymer was measured by GPC in the same manner. As the result, Mn was 61,000 and Mw, 110,000.

Figure 8:
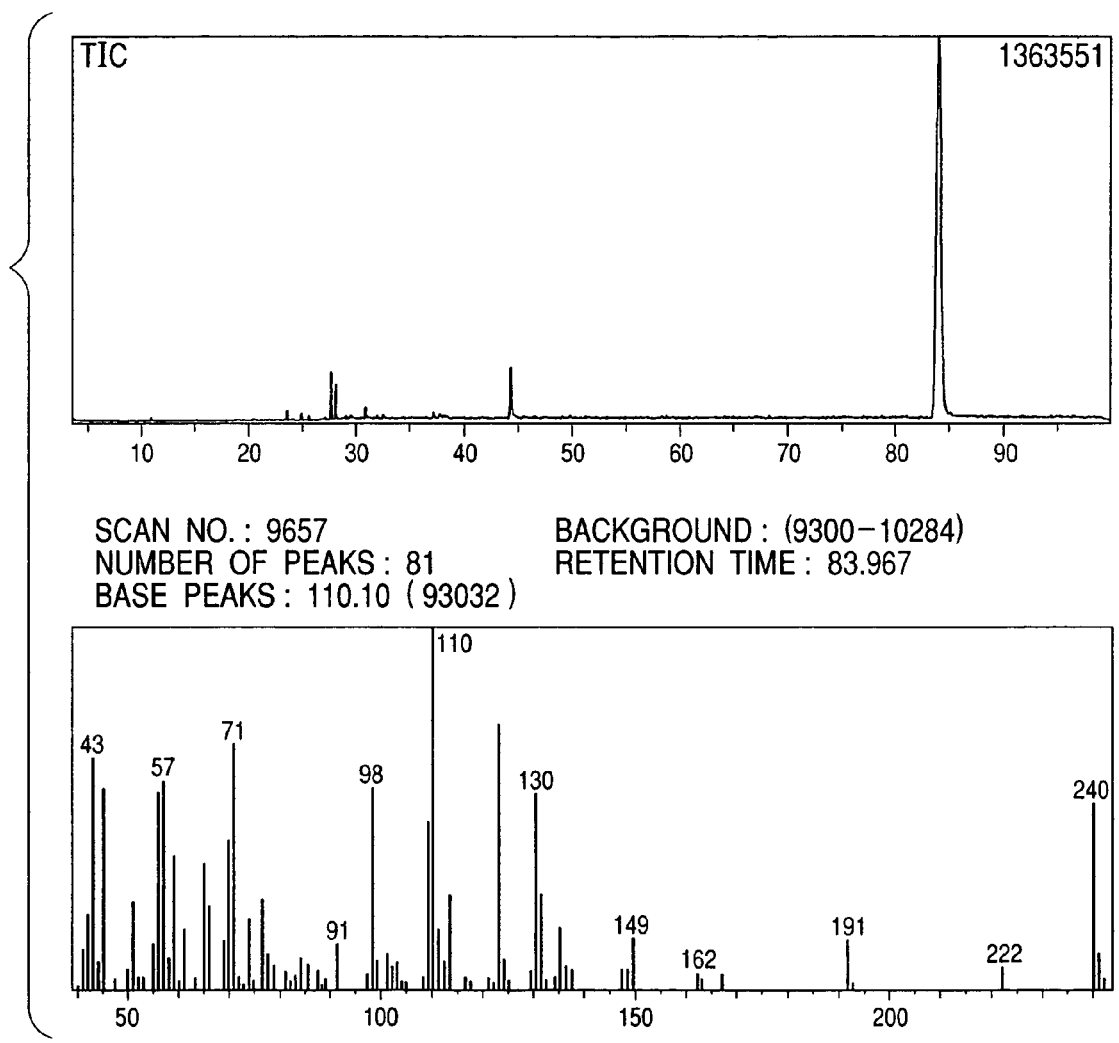
FIG. 8 is a MS spectrum of methyl-esterified product of the PHA monomer unit according to Example 8.

The obtained polymer was further analyzed by GC-MS in the same manner as in Example 5. The Total Ion Chromatograph (TIC) and mass spectrum are shown in FIG. 8. The mass spectrum of the peak around 85 minute confirmed that the peak shows 3-hydroxy-5-thiophenoxy valeric acid methyl ester. Other unit was only 3-hydroxydecanoic acid methyl ester around 25 minute, and the content was 0.1% or less. As a result, it was found therefrom that the resultant polymer was a polyhydroxyalkanoate containing the monomer unit 3-hydroxy-5-thiophenoxy valeric acid in an amount of 99.9% or more.

Example 9

An objective polymer was obtained in the same manner as in Example 8 except that H45 strain was used instead of YN2 strain. The freeze-dried pellets' weight was 177 mg and the weight of the polymer was 39 mg.

The molecular weight of this polymer was measured by GPC in the same manner. As the result, the resultant polymer had Mn: 67,000 and Mw: 120,000.

Figure 9:
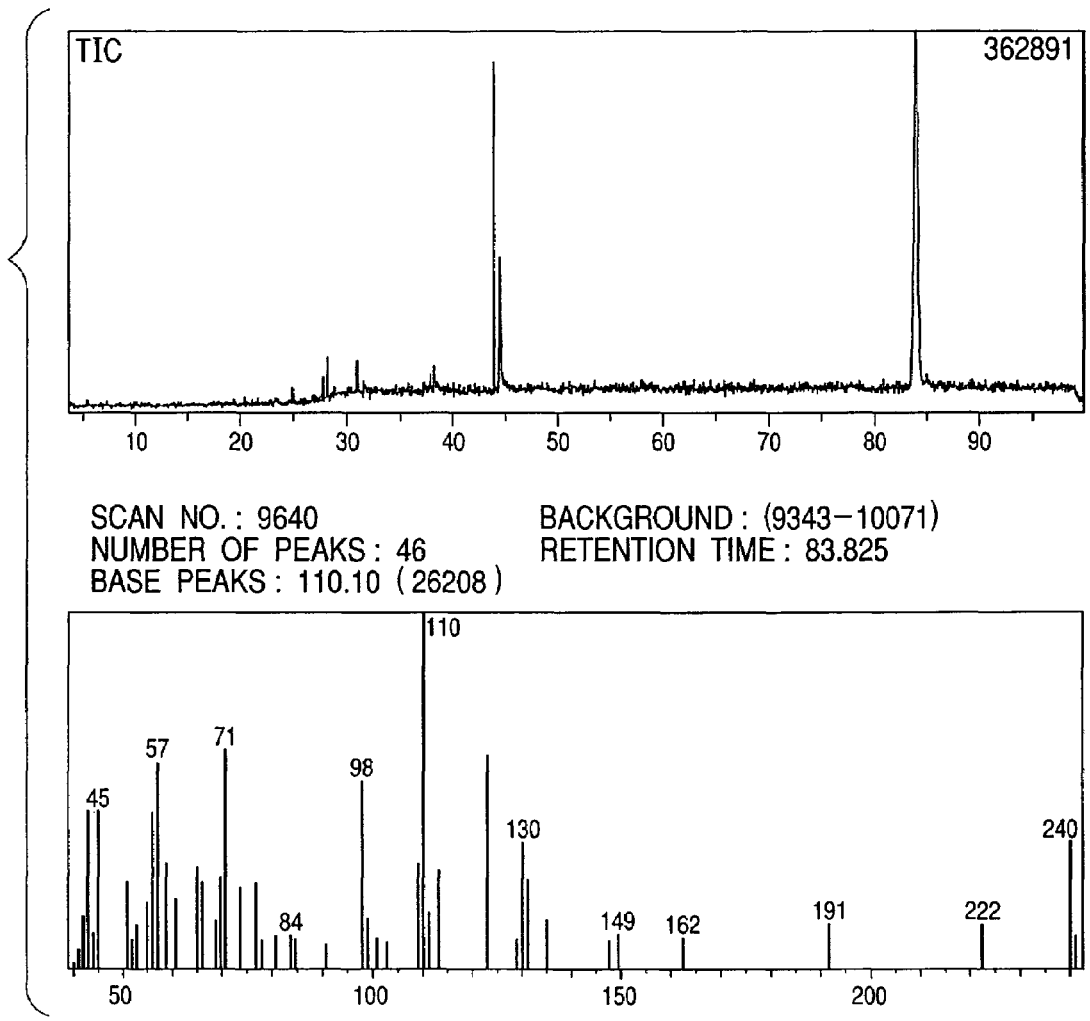
FIG. 9 is a MS spectrum of methyl-esterified product of the PHA monomer unit according to Example 9.

The resultant polymer was further analyzed by GC-MS in the same manner as in Example 5. The Total Ion Chromatograph (TIC) and mass spectrum are shown in FIG. 9. The mass spectrum of the peak around 85 minute confirmed that the peak shows 3-hydroxy-5-thiophenoxy valeric acid methyl ester. Other unit was only 3-hydroxydecanoic acid methyl ester around 25 minute, and the content was 0.1% or less. As a result, it was found therefrom that the resultant polymer was a polyhydroxyalkanoate containing the monomer unit 3-hydroxy-5-thiophenoxy valeric acid in an amount of 99.9% or more.

Next, PHA producing microorganism was cultured in the medium containing 4-thiophenoxy butyric acid (hereinafter often "TPxBA") to produce PHA mainly containing 3-hydroxy-4-thiophenoxy butyric acid (hereinafter often "3HTPxB") unit (Examples 10 to 19).

Example 10

In 200 mL of M9 medium containing 0.5% of D-glucose and 0.1% of TPxBA, Pseudomonas cichorii strain YN2 was inoculated to effect shaking culture at 30° C. and 125 strokes/minute. After 50 hours, the bacterial body was collected by centrifugation, and then again suspended in 200 mL of M9 medium containing 0.5% of D-glucose and 0.1% of TPxBA and not containing any nitrogen source (NH$_4$Cl), further followed by shaking culture at 30° C. and 125 strokes/minute. After 47 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 52 mg of a PHA.

The structure of the obtained polymer was determined by $^1$H-NMR and $^{13}$C-NMR (FT-NMR: Bruker DPX400; $^1$H resonance frequency: 400 MHz; $^{13}$C resonance frequency: 100 MHz; measurement nuclide: $^1$H and $^{13}$C; used solvent: CDCl$_3$; measurement temperature: room temperature).

Figure 10:
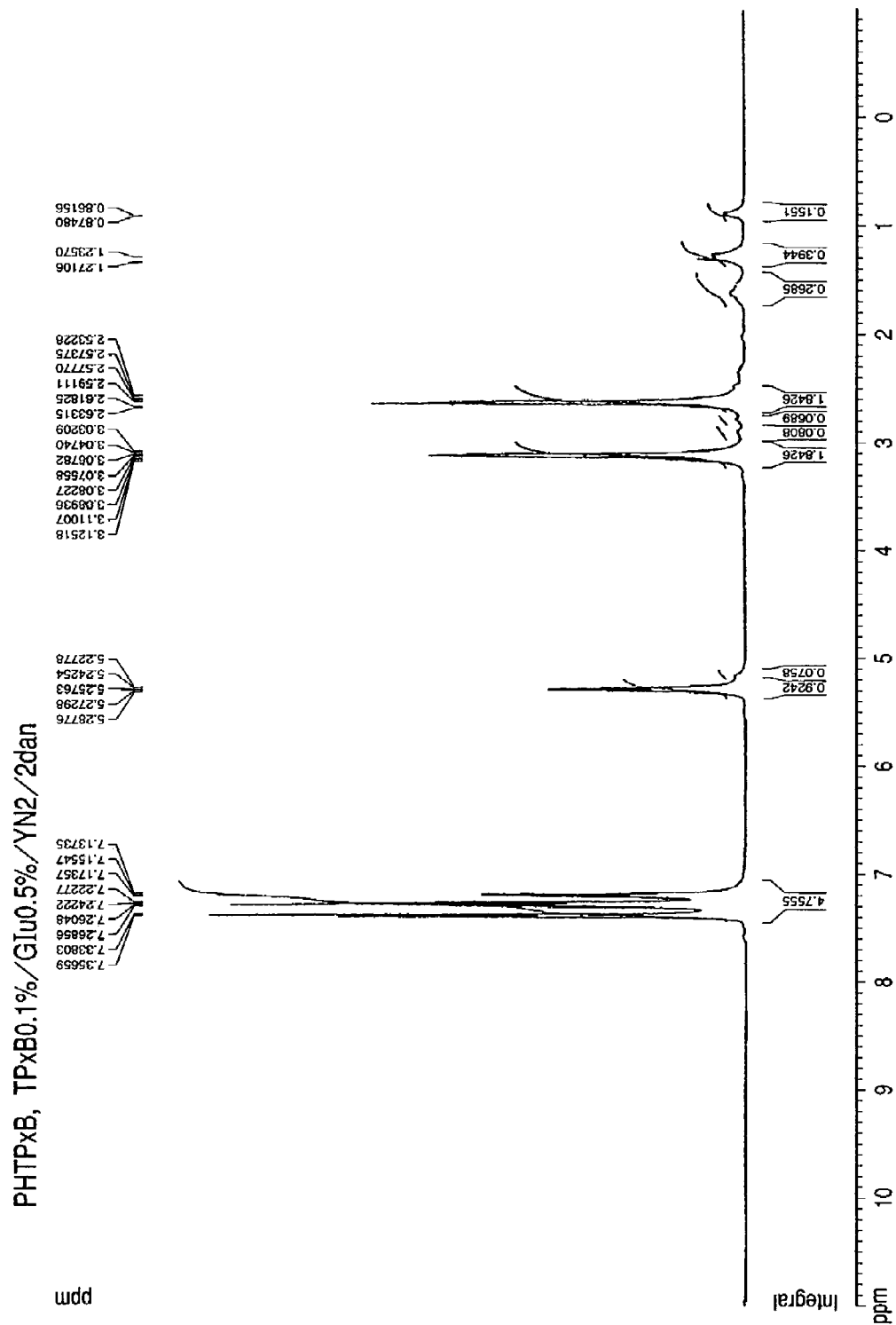
FIG. 10 is a $^1$H-NMR spectrum chart of a polymer obtained according to Example 10.
Figure 11:
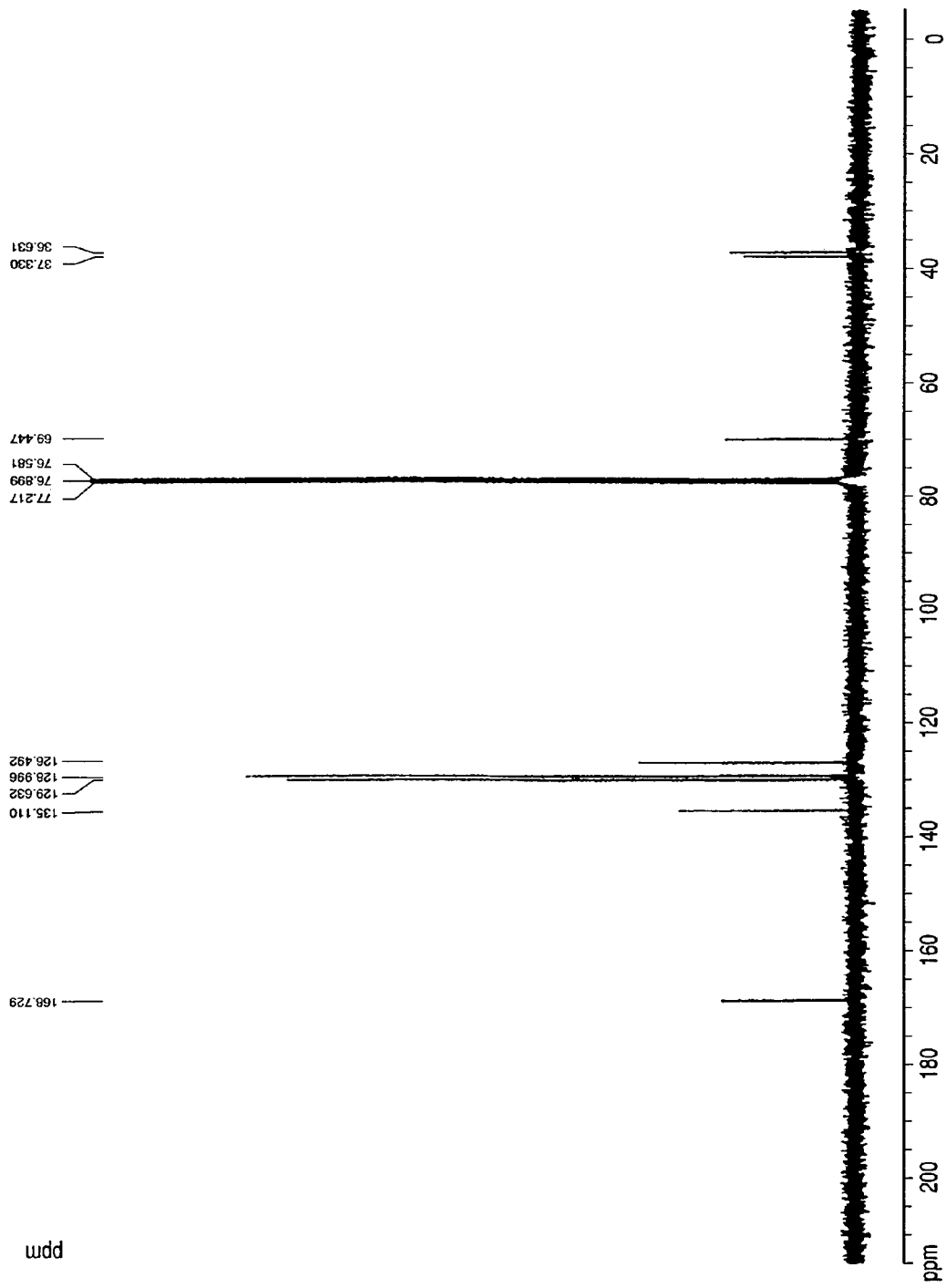
FIG. 11 is a $^{13}$C-NMR spectrum chart of a polymer obtained according to Example 10.

The $^1$H-NMR spectrum chart are shown in FIG. 10 and the results of its identification in Table 6. The $^{13}$C-NMR spectrum chart is shown in FIG. 11, and the results of its identification in Table 7.

TABLE 6

| Chemical shift (ppm) | Integrated value | Split | Assignment |
|---|---|---|---|
| 2.59 | 2 | m | c1 |
| 3.08 | 2 | m | b1 |
| 5.22 | 2 | quint | d1 |
| 7.15 | 1 | t | h1 |
| 7.24 | 2 | t | g1 & i1 |
| 7.34 | 2 | d | f1 & j1 |

TABLE 7

| Chemical shift (ppm) | Split | Assignment |
|---|---|---|
| 36.6 | s | b1 or c1 |
| 37.3 | s | b1 or c1 |
| 69.4 | s | d1 |
| 126.5 | s | h1 |
| 129.0 | s | f1 & j1 |
| 129.6 | s | g1 & i1 |
| 135.1 | s | e1 |
| 168.7 | s | a1 |

As shown in Table 6 and Table 7', it was ascertained that the PHA was a PHA represented by Chemical Formula (31).

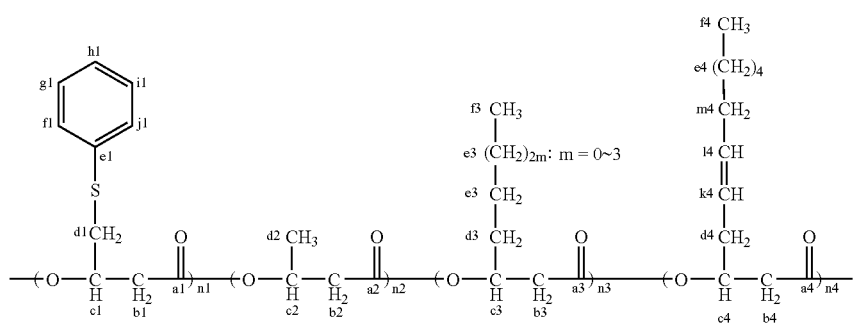

(31)

The molecular weight of this PHA was also measured by gel permeation chromatography (GPC: Toso HLC-8220; column: Toso TSK-GEL Super HM-H; solvent: chloroform; in terms of polystyrene). As the result, it had Mn of 25,100 and MW of 53,100.

Example 11

In 200 mL of M9 medium containing 0.5% of D-glucose and 0.1% of TPXBA, *Pseudomonas cichonii* strain H45 was inoculated to effect shaking culture at 30° C. and 125 strokes/minute. After 50 hours, the bacterial body was collected by centrifugation, and then again suspended in 200 mL of M9 medium containing 0.5% of D-glucose and 0.1% of TPxBA and not containing any nitrogen source (NH$_4$Cl), further followed by shaking culture at 30° C. and 125 strokes/minute. After 47 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 25 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 87.3 mol %.

Example 12

In 200 mL of M9 medium containing 0.5% of D-glucose and 0.1% of TPxBA, *Pseudomonas jessenii* strain P161 was inoculated to effect shaking culture at 30° C. and 125 strokes/minute. After 50 hours, the bacterial body was collected by centrifugation, and then again suspended in 200 mL of M9 medium containing 0.5% of D-glucose and 0.1% of TPxBA and not containing any nitrogen source (NH$_4$Cl), further followed by shaking culture at 30° C. and 125 strokes/minute. After 47 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 25 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 85.6 mol %.

Example 13

In 200 mL of M9 medium containing 0.5% of polypeptone and 0.1% of TPxBA, *Pseudomonas cichorii* strain YN2 was inoculated to effect shaking culture at 30° C. and 125 strokes/minute. After 48 hours, the bacterial body was collected by centrifugation, and then again suspended in 200 mL of M9 medium containing 0.5% of sodium pyruvate and 0.1% of TPxBA and not containing any nitrogen source (NH$_4$Cl), further followed by shaking culture at 30° C. and 125 strokes/ minute. After 48 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 118 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 92.6 mol %.

Example 14

In 200 mL of M9 medium containing 0.5% of polypeptone and 0.1% of TPxBA, *Pseudomonas cichorii* strain H45 was inoculated to effect shaking culture at 30° C. and 125 strokes/minute. After 47 hours, the bacterial body was collected by centrifugation, and then again suspended in 200 mL of M9 medium containing 0.5% of sodium pyruvate and 0.1% of FTPxBA and not containing any nitrogen source ($NH_4Cl$), further followed by shaking culture at 30° C. and 125 strokes/minute. After 47 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 24 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 91.2 mol %.

Example 15

In 200 mL of M9 medium containing 0.5% of polypeptone and 0.1% of TPxBA, *Pseudomonas jessenii* strain P161 was inoculated to effect shaking culture at 30° C. and 125 strokes/minute. After 48 hours, the bacterial body was collected by centrifugation, and then again suspended in 200 mL of M9 medium containing 0.5% of sodium pyruvate and 0.1% of FTPxBA and not containing any nitrogen source ($NH_4Cl$), further followed by shaking culture at 30° C. and 125 strokes/minute. After 47 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 40 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 89.3 mol %.

Example 16

In 200 mL of M9 medium containing 0.5% of sodium glutamate and 0.1% of TPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 41 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 94.5 mol %.

Example 17

In 200 mL of M9 medium containing 0.5% of yeast extract and 0.1% of TPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 9 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 82.6 mol %.

Example 18

In 200 mL of M9 medium containing 0.5% of n-nonanoic acid and 0.1% of TPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 40 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 7.0 mol %.

Example 19

In 200 mL of M9 medium containing 0.1% of n-octanoic acid and 0.1% of TPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 35 mg of a PHA.

The PHA thus obtained was analyzed by NMR spectroscopy under the same condition as those in Example 10. As the result, it was found therefrom that the resultant PHA contained the monomer unit 3-hydroxy-4-thiophenoxy butyric acid in amount of 8.0 mol %.

Table 8 shows the bacterial-body dry weight, polymer dry weight and polymer dry weight/bacterial-body dry weight and the mol % of the 3HTPxB unit of the polymer obtained in each of Examples 10 to 19.

TABLE 8

| | Bacterial-body dry weight (mg/L) | Polymer dry weight (mg/L) | Polymer dry weight/bacterial-body dry weight (%) | 3HTPxB unit mol % |
|---|---|---|---|---|
| Example 10 | 695 | 260 | 37.4 | 92.1 |
| Example 11 | 495 | 125 | 25.3 | 87.3 |
| Example 12 | 725 | 250 | 34.5 | 85.6 |
| Example 13 | 1160 | 590 | 50.9 | 92.6 |
| Example 14 | 550 | 120 | 21.8 | 91.2 |
| Example 15 | 540 | 110 | 20.4 | 89.3 |
| Example 16 | 650 | 205 | 31.5 | 94.5 |
| Example 17 | 860 | 45 | 5.2 | 82.6 |
| Example 18 | 425 | 200 | 47.1 | 7.0 |
| Example 19 | 405 | 175 | 43.2 | 8.0 |

Example 20

In 200 mL of M9 medium containing 0.5% of D-glucose and 0.1% of 5-[(4-methylphenyl)sulfanyl] valeric acid (hereinafter "MeTPxVA"), *Pseudomonas cichorii* strain YN2 was inoculated to effect shaking culture at 30° C. and 125 strokes/minute. After 72 hours, the bacterial body was collected by centrifugation, and then again suspended in 200 mL of M9 medium containing 0.5% of D-glucose and 0.1% of MeTPxVA and not containing any nitrogen source ($NH_4Cl$), further followed by shaking culture at 30° C. and 125 strokes/minute. After 48 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 75 mg of a PHA.

The molecular weight of this PHA was also measured by gel permeation chromatography (GPC: Toso HLC-8220; column: Toso TSK-GEL Super HM-H; solvent: chloroform; in terms of polystyrene). As the result, it had Mn of 60,300 and Mw of 131,600.

The structure of the obtained polymer was determined by $^1$H-NMR (FT-NMR: Bruker DPX400; $^1$H resonance frequency: 400 MHz; measurement nuclide: $^1$H; used solvent: $CDCl_3$; reference: capillary enclosed $TMS/CDCl_3$; measurement temperature: room temperature).

Figure 12:
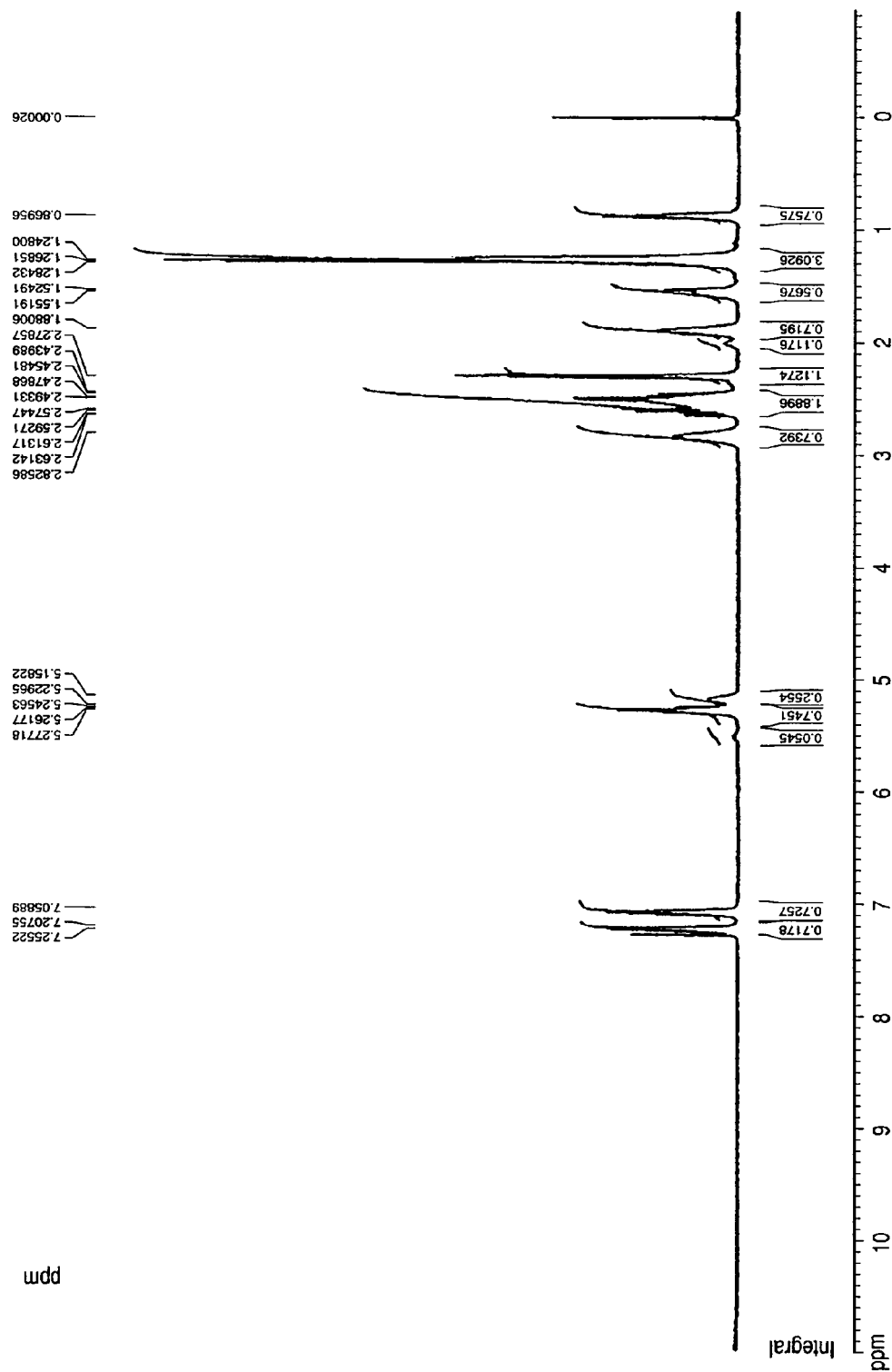
FIG. 12 is a $^1$H-NMR spectrum chart of a PHA obtained according to Example 20.

The $^1$H-NMR spectrum chart are shown in FIG. 12 and the results of its identification in Table 9.

TABLE 9

| Chemical shift (ppm) | Integrated value | Split | Assignment |
|---|---|---|---|
| 1.88 | 2H | m | d |
| 2.28 | 3H | s | l |
| 2.43-2.63 | 2H | m | b |
| 2.82 | 2H | m | e |
| 5.24 | 1H | m | c |
| 7.05 | 2H | m | g, k |
| 7.20 | 2H | m | h, j |

As shown in Table 9, the PHA contains 3-hydroxy-5-[(4-methylphenyl)sulfanyl] valeric acid (hereinafter, simply "3HMeTPxV") as the monomer unit. As the other monomer unit, straight-chain 3-hydroxyalkanoic acid unit having 4 to 12 carbons such as 3-hydroxybutyric acid and 3-hydroxyvaleric acid, or straight-chain 3-hydroxyalkenic acid unit. Specifically, it was confirmed that the constitution was mix polymer PHA represented by the following formula (32).

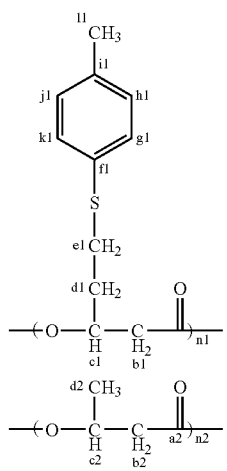

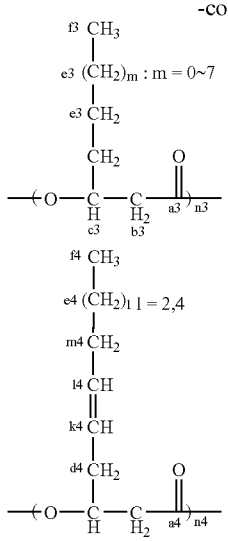

-continued

Figure 13:
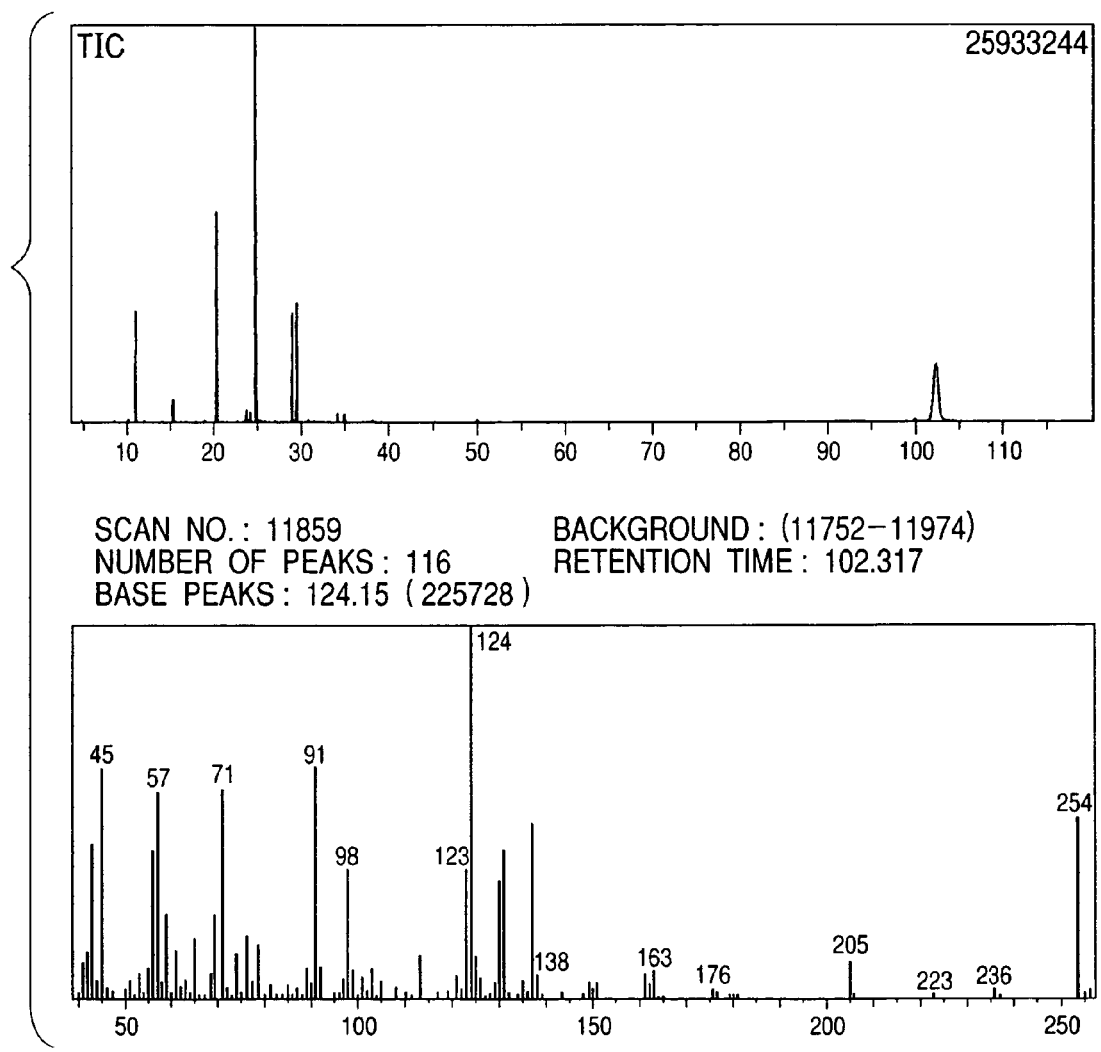
FIG. 13 is a GC-MS measured result of monomer methylester mixture obtained from methanolysis of PHA according to Example 20, and the upper portion shows TIC (gas chromatography), the lower portion, a MS spectrum of methyl-esterified product of the 3HMeTPxV.

The PHA thus obtained was further subjected to methanolysis by a conventional method, and thereafter analyzed with a gas chromatography mass spectrometer (GC-MS, Shimadzu QP-5050, EI method) to make identification of the methyl-esterified product of the PHA monomer unit. FIG. 13 shows the measured GC-MS spectrum data and Table 10 shows content ratio (composition ratio) of each unit contained, calculated from the peak area of the gas chromatography. As can be seen from the result shown in FIG. 13, it was confirmed that the PHA was a PHA containing a unit of 3HMeTPxV represented by the following formula (6).

TABLE 10

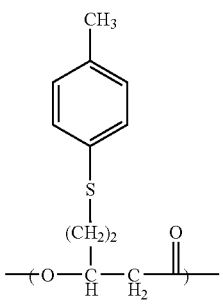

(6)

| | |
|---|---|
| Bacterial-body dry weight | 1065 mg/L |
| polymer dry weight | 375 mg/L |
| polymer dry weight/bacterial-body dry weight | 35.2% |
| Monomer unit composition (peak area ratio): | |
| 3-Hydroxybutyric acid | 6.7% |
| 3-Hydroxyhexanoic acid | 1.4% |
| 3-Hydroxyoctanoic acid | 12.7% |
| 3-Hydroxydecanoic acid | 24.7% |
| 3-Hydroxydodecanoic acid | 7.0% |
| 3-Hydroxydodecenoic acid | 8.0% |
| 3-Hydroxy-5-[(4-methylphenyl)sulfanyl] valeric acid | 39.5% |

Example 21

In 200 mL of M9 medium containing 0.5% of D-glucose and 0.1% of MeTPxVA acid, *Pseudomonas cichorii* strain H45 was inoculated to effect shaking culture at 30° C. and 125 strokes/minute. After 72 hours, the bacterial body was collected by centrifugation, and then again suspended in 200 mL of M9 medium containing 0.5% of D-glucose and 0.1% of MeTPxVA and not containing any nitrogen source (NH$_4$Cl), further followed by shaking culture at 30° C. and 125 strokes/minute. After 48 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 71 mg of a PHA.

The PHA thus obtained was further subjected to methanolysis under the same condition as those in Example 20, and thereafter analyzed with a gas chromatography mass spectrometer (GC-MS, Shimadzu QP-5050, EI method) to make identification of the methyl-esterified product of the PHA monomer unit. The results are shown in Table 11. As a result, it was ascertained that the PHA was the PHA represented by Chemical Formula (6) containing 3HMeTPxV as a monomer unit.

TABLE 11

| | |
|---|---|
| Bacterial-body dry weight | 835 mg/L |
| polymer dry weight | 335 mg/L |
| polymer dry weight/bacterial-body dry weight | 42.5% |
| Monomer unit composition (peak area ratio): | |
| 3-Hydroxybutyric acid | 0.0% |
| 3-Hydroxyhexanoic acid | 1.4% |
| 3-Hydroxyoctanoic acid | 9.2% |
| 3-Hydroxydecanoic acid | 20.8% |
| 3-Hydroxydodecanoic acid | 4.2% |
| 3-Hydroxydodecenoic acid | 7.1% |
| 3-Hydroxy-5-[(4-methylphenyl)sulfanyl] valeric acid | 57.3% |

Example 22

In 200 mL of M9 medium containing 0.5% of D-glucose and 0.1% of MeTPxVA acid, *Pseudomonas jessenii* strain P161 was inoculated to effect shaking culture at 30° C. and 125 strokes/minute. After 72 hours, the bacterial body was collected by centrifugation, and then again suspended in 200 mL of M9 medium containing 0.5% of D-glucose and 0.1% of MeTPxVA and not containing any nitrogen source (NH$_4$Cl), further followed by shaking culture at 30° C. and 125 strokes/minute. After 48 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 52 mg of a PHA.

The PHA thus obtained was further subjected to methanolysis under the same condition as those in Example 20, and thereafter analyzed with a gas chromatography mass spectrometer (GC-MS, Shimadzu QP-5050, EI method) to make identification of the methyl-esterified product of the PHA monomer unit. The results are shown in Table 12. As a result, it was ascertained that the PHA was the PHA represented by Chemical Formula (6) containing 3HMeTPxV as a monomer unit.

TABLE 12

| | |
|---|---|
| Bacterial-body dry weight | 965 mg/L |
| polymer dry weight | 260 mg/L |
| polymer dry weight/bacterial-body dry weight | 26.9% |
| Monomer unit composition (peak area ratio): | |
| 3-Hydroxybutyric acid | 6.3% |
| 3-Hydroxyhexanoic acid | 1.8% |
| 3-Hydroxyoctanoic acid | 14.0% |
| 3-Hydroxydecanoic acid | 22.8% |
| 3-Hydroxydodecanoic acid | 6.7% |
| 3-Hydroxydodecenoic acid | 11.6% |
| 3-Hydroxy-5-[(4-methylphenyl)sulfanyl]valeric acid | 36.8% |

Example 23

In 200 mL of M9 medium containing 0.5% of polypeptone (available from Wakojunyaku K. K.) and 0.1% of MeTPxVA acid, *Pseudomonas cichorii* strain YN2 was inoculated to effect shaking culture at 30° C. and 125 strokes/minute. After 72 hours, the bacterial body was collected by centrifugation, and then again suspended in 200 mL of M9 medium containing 0.5% of sodium pyruvate and 0.1% of MeTPxVA and not containing any nitrogen source ($NH_4Cl$), further followed by shaking culture at 30° C. and 125 strokes/minute. After 48 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 120 mg of a PHA.

The PHA thus obtained was further subjected to methanolysis under the same condition as those in Example 20, and thereafter analyzed with a gas chromatography mass spectrometer (GC-MS, Shimadzu QP-5050, EI method) to make identification of the methyl-esterified product of the PHA monomer unit. The results are shown in Table 13. As a result, it was ascertained that the PHA was the PHA represented by Chemical Formula (6) containing 3HMeTPxV as a monomer unit.

TABLE 13

| | |
|---|---|
| Bacterial-body dry weight | 950 mg/L |
| polymer dry weight | 600 mg/L |
| polymer dry weight/bacterial-body dry weight | 63.2% |
| Monomer unit composition (peak area ratio): | |
| 3-Hydroxybutyric acid | 8.7% |
| 3-Hydroxyhexanoic acid | 2.1% |
| 3-Hydroxyoctanoic acid | 10.9% |
| 3-Hydroxydecanoic acid | 23.2% |
| 3-Hydroxydodecanoic acid | 6.4% |

TABLE 13-continued

| | |
|---|---|
| 3-Hydroxydodecenoic acid | 12.7% |
| 3-Hydroxy-5-[(4-methylphenyl)sulfanyl]valeric acid | 36.0% |

Example 24

In 200 mL of M9 medium containing 0.5% of polypeptone (available from Wakojunyaku K. K.) and 0.1% of MeTPxVA acid, *Pseudomonas cichorii* strain H45 was inoculated to effect shaking culture at 30° C. and 125 strokes/minute. After 72 hours, the bacterial body was collected by centrifugation, and then again suspended in 200 mL of M9 medium containing 0.5% of sodium pyruvate and 0.1% of MeTPxVA and not containing any nitrogen source ($NH_4Cl$), further followed by shaking culture at 30° C. and 125 strokes/minute. After 48 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 57 mg of a PHA.

The PHA thus obtained was further subjected to methanolysis under the same condition as those in Example 20, and thereafter analyzed with a gas chromatography mass spectrometer to make identification of the methyl-esterified product of the PHA monomer unit. The results are shown in Table 14. As a result, it was ascertained that the PHA was the PHA represented by Chemical Formula (6) containing 3HMeTPxV as a monomer unit.

TABLE 14

| | |
|---|---|
| Bacterial-body dry weight | 880 mg/L |
| polymer dry weight | 285 mg/L |
| polymer dry weight/bacterial-body dry weight | 32.4% |
| Monomer unit composition (peak area ratio): | |
| 3-Hydroxybutyric acid | 0.5% |
| 3-Hydroxyhexanoic acid | 1.4% |
| 3-Hydroxyoctanoic acid | 8.8% |
| 3-Hydroxydecanoic acid | 17.6% |
| 3-Hydroxydodecanoic acid | 4.1% |
| 3-Hydroxydodecenoic acid | 6.5% |
| 3-Hydroxy-5-[(4-methylphenyl)sulfanyl]valeric acid | 61.1% |

Example 25

In 200 mL of M9 medium containing 0.5% of polypeptone (available from Wakojunyaku K. K.) and 0.1% of MeTPxVA acid, *Pseudomonas jessenii* strain P161 was inoculated to effect shaking culture at 30° C. and 125 strokes/minute. After 72 hours, the bacterial body was collected by centrifugation, and then again suspended in 200 mL of M9 medium containing 0.5% of sodium pyruvate and 0.1% of MeTPxVA and not containing any nitrogen source ($NH_4Cl$), further followed by shaking culture at 30° C. and 125 strokes/minute. After 48 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 56-mg of a PHA.

The PHA thus obtained was further subjected to methanolysis under the same condition as those in Example 20, and thereafter analyzed with a gas chromatography mass spectrometer to make identification of the methyl-esterified product of the PHA monomer unit. The results are shown in Table 15. As a result, it was ascertained that the PHA was the PHA represented by Chemical Formula (6) containing 3HMeT-PxV as a monomer unit.

TABLE 15

| | |
|---|---|
| Bacterial-body dry weight | 785 mg/L |
| polymer dry weight | 280 mg/L |
| polymer dry weight/bacterial-body dry weight | 35.7% |
| Monomer unit composition (peak area ratio): | |
| 3-Hydroxybutyric acid | 8.8% |
| 3-Hydroxyhexanoic acid | 2.1% |
| 3-Hydroxyoctanoic acid | 13.4% |
| 3-Hydroxydecanoic acid | 25.7% |
| 3-Hydroxydodecanoic acid | 6.0% |
| 3-Hydroxydodecenoic acid | 7.7% |
| 3-Hydroxy-5-[(4-methylphenyl)sulfanyl] valeric acid | 36.3% |

Example 26

In 200 mL of M9 medium containing 0.5% of polypeptone (available from Wakojunyaku K. K.) and 0.1% of MeTPxVA acid, *Pseudomonas cichorii* strain YN2 was inoculated to effect shaking culture at 30° C. and 125 strokes/minute. After 61 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 5 mg of a PHA.

The PHA thus obtained was further subjected to methanolysis under the same condition as those in Example 20, and thereafter analyzed with a gas chromatography mass spectrometer to make identification of the methyl-esterified product of the PHA monomer unit. The results are shown in Table 16. As a result, it was ascertained that the PHA was the PHA represented by Chemical Formula (6) containing 3HMeT-PxV as a monomer unit.

TABLE 16

| | |
|---|---|
| Bacterial-body dry weight | 590 mg/L |
| polymer dry weight | 25 mg/L |
| polymer dry weight/bacterial-body dry weight | 4.2% |
| Monomer unit composition (peak area ratio): | |
| 3-Hydroxybutyric acid | 25.1% |
| 3-Hydroxyhexanoic acid | 1.0% |
| 3-Hydroxyoctanoic acid | 8.6% |

TABLE 16-continued

| | |
|---|---|
| 3-Hydroxydecanoic acid | 9.5% |
| 3-Hydroxydodecanoic acid | 2.9% |
| 3-Hydroxydodecenoic acid | 1.1% |
| 3-Hydroxy-5-[(4-methylphenyl)sulfanyl] valeric acid | 51.8% |

Example 27

In 200 mL of M9 medium containing 0.5% of yeast extract (DIFCO) and 0.1% of MeTPxVA acid, *Pseudomonas cichorii* strain YN2 was inoculated to effect shaking culture at 30° C. and 125 strokes/minute. After 61 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.4.5 μm in pore diameter, and thereafter concentrated by means of a rotary evaporator. The concentrated liquid was re-precipitated with cold methanol, and further only the precipitate formed was collected, followed by vacuum drying to obtain 2 mg of a PHA.

The PHA thus obtained was further subjected to methanolysis under the same condition as those in Example 20, and thereafter analyzed with a gas chromatography mass spectrometer to make identification of the methyl-esterified product of the PHA monomer unit. The results are shown in Table 17. As a result, it was ascertained that the PHA was the PHA represented by Chemical Formula (6) containing 3HMeT-PxV as a monomer unit.

TABLE 17

| | |
|---|---|
| Bacterial-body dry weight | 840 mg/L |
| polymer dry weight | 10 mg/L |
| polymer dry weight/bacterial-body dry weight | 1.2% |
| Monomer unit composition (peak area ratio): | |
| 3-Hydroxybutyric acid | 20.5% |
| 3-Hydroxyhexanoic acid | 1.1% |
| 3-Hydroxyoctanoic acid | 12.4% |
| 3-Hydroxydecanoic acid | 17.1% |
| 3-Hydroxydodecanoic acid | 4.0% |
| 3-Hydroxydodecenoic acid | 2.1% |
| 3-Hydroxy-5-[(4-methylphenyl)sulfanyl] valeric acid | 42.9% |

Example 28

In 200 mL of M9 medium containing 0.5% of glutamic acid and 0.1% of MeTPxVA acid, *Pseudomonas cichorii* strain YN2 was inoculated to effect shaking culture at 30° C. and 125 strokes/minute. After 61 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 3 mg of a PHA.

The PHA thus obtained was further subjected to methanolysis under the same condition as those in Example 20, and thereafter analyzed with a gas chromatography mass spectrometer to make identification of the methyl-esterified product of the PHA monomer unit. The results are shown in Table 18. As a result, it was ascertained that the PHA was the PHA represented by Chemical Formula (6) containing 3HMeT-PxV as a monomer unit.

TABLE 18

| | |
|---|---|
| Bacterial-body dry weight | 585 mg/L |
| polymer dry weight | 15 mg/L |
| polymer dry weight/bacterial-body dry weight | 2.6% |
| Monomer unit composition (peak area ratio): | |
| 3-Hydroxybutyric acid | 32.3% |
| 3-Hydroxyhexanoic acid | 1.6% |
| 3-Hydroxyoctanoic acid | 17.6% |
| 3-Hydroxydecanoic acid | 18.6% |
| 3-Hydroxydodecanoic acid | 5.2% |
| 3-Hydroxydodecenoic acid | 5.9% |
| 3-Hydroxy-5-[(4-methylphenyl)sulfanyl]valeric acid | 18.8% |

Example 29

In 200 mL of M9 medium containing 0.1% of nonanoic acid and 0.1% of MeTPxVA acid, *Pseudomonas cichorii* strain YN2 was inoculated to effect shaking culture at 30° C. and 125 strokes/minute. After 61 hours, the bacterial body was collected by centrifugation, and then washed once with cold methanol, followed by freeze-drying. The freeze-dried bacterial body was weighed.

The resultant freeze-dried pellets were then suspended in 20 mL of chloroform, which were then stirred at 60° C. for 20 hours to extract PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 31 mg of a PHA.

The PHA thus-obtained was further subjected to methanolysis under the same condition as those in Example 20, and thereafter analyzed with a gas chromatography mass spectrometer to make identification of the methyl-esterified product of the PHA monomer unit. The results are shown in Table 19. As a result, it was ascertained that the PHA was the PHA represented by Chemical Formula (6) containing 3HMeT-PxV as a monomer unit.

TABLE 19

| | |
|---|---|
| Bacterial-body dry weight | 460 mg/L |
| polymer dry weight | 155 mg/L |
| polymer dry weight/bacterial-body dry weight | 33.7% |
| Monomer unit composition (peak area ratio): | |
| 3-Hydroxyvaleric acid | 1.4% |
| 3-Hydroxyheptanoic acid | 32.6% |
| 3-Hydroxyoctanoic acid | 3.5% |
| 3-Hydroxynonanoic acid | 60.8% |
| 3-Hydroxydecanoic acid | 0.7% |
| 3-Hydroxy-5-[(4-methylphenyl)sulfanyl]valeric acid | 1.0% |

Example 30

Synthesis of 5-[(4-fluorophenyl)sulfanyl]valeric acid

In a four-necked round-bottom flask, 240 mL of dehydrated acetone was put, and 15.20 g (0.11 mol) of potassium carbonate was added-thereto, which were then stirred in an atmosphere of nitrogen. To the resultant solution, 9.00 g (0.06 mol) of sodium iodide and 8.97 g (0.07 mol) of 4-fluorobenzenethiol were added, followed by thorough stirring at room temperature and in an atmosphere of nitrogen. Then, 12.55 g (0.06 mol) of ethyl 5-bromovalerate was further added, followed by heating and reflux at 65° C. for 18 hours.

After the reaction was completed, the acetone was evaporated off by means of a rotary evaporator, and the reaction mixture was again dissolved in chloroform, followed by addition of water to separate the reaction mixture, where the organic phase was dehydrated with anhydrous magnesium sulfate. Thereafter, the chloroform was evaporated off by means of a rotary evaporator, followed by drying by means of a vacuum pump to obtain 14.78 g of crude, ethyl 5-[(4-fluorophenyl)sulfanyl]valerate (having a GC-MS peak ratio of 93.55% as determined using a gas chromatography mass spectrometer GC-MS, Shimadzu QP-5050, EI method).

The ethyl 5-[(4-fluorophenyl)sulfanyl]valerate crude product obtained here was subjected to the following hydrolysis reaction, without being purified.

14.78 g of the ester crude product obtained was dissolved in 300 mL of an ethanol-water 1:9 (v/v) mixed solvent, and potassium hydroxide was added in an amount of 10-fold mol, where the reaction was carried out for 4 hours under ice bath.

The resultant reaction mixture was poured into about 2 L of an aqueous 0.1 mol/L hydrochloric-acid solution to effect precipitation, and the precipitate formed was taken out by filtration. The reaction product obtained here was dried using a vacuum pump to obtain crude, 5-[(4-fluorophenyl)sulfanyl]valeric acid.

The 5-[(4-fluorophenyl)sulfanyl]valeric acid crude product obtained here was dissolved in a small quantity of a hot ethanol-hexane mixed solvent, and cooled little by little to effect recrystallization, followed by drying using a vacuum pump to obtain the desired compound 5-[(4-fluorophenyl)sulfanyl]valeric acid.

The 5-[(4-fluorophenyl)sulfanyl]valeric acid obtained here was in a yield of 9.02 g.

Its total yield was 65.9% on the basis of ethyl 5-bromovalerate.

The compound thus obtained was analyzed by NMR spectroscopy under the following conditions.
—Measuring Instrument—
FT-NMR: Bruker DPX400.
Resonance frequency: $^1$H 400 MHz.
—Measuring Instrument—
Measurement nuclide: $^1$H.
Solvent used: $CDCl_3$.
Reference: Capillary-encapsulated TMS/$CDCl_3$.
Measurement temperature: room temperature.

Figure 14:
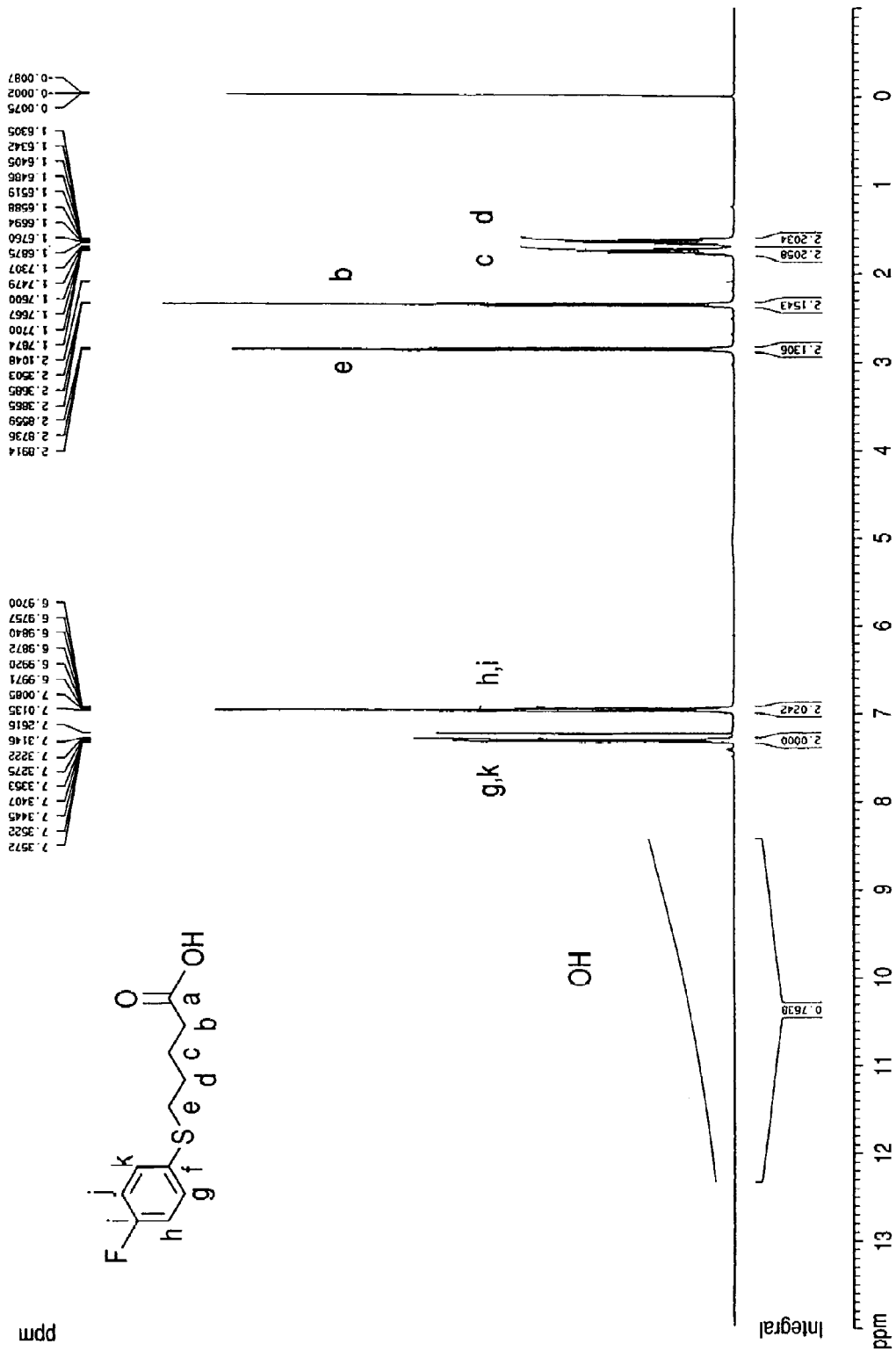
FIG. 14 is a $^1$H-NMR spectrum chart of 5-[(4-fluorophenyl)sulfanyl]valeric acid.

The $^1$H-NMR spectrum chart and the results of its identification are shown in FIG. 14 and Table 20, respectively.

These results proved that the desired novel compound 5-[(4-fluorophenyl)sulfanyl]valeric acid represented by Chemical Formula (36) was synthesized.

TABLE 20

(36)

[Structure: 4-fluorophenyl-S-CH2-CH2-CH2-CH2-C(=O)-OH with labels h,g,f on one phenyl ring side, i,j,k on the other, e,d,c,b,a on chain]

$^1$H-NMR Spectrum Identification Results (see FIG. 14)

| Chemical shift (ppm) | Integral ratio | Splitting | Identification results |
|---|---|---|---|
| 1.65 | 2 | m | d |
| 1.76 | 2 | m | c |
| 2.36 | 2 | t | b |
| 2.87 | 2 | t | e |
| 6.99 | 2 | m | h, j |
| 7.34 | 2 | m | g, k |
| 8.40 to 12.00 | 1 | br | OH |

Examples are given below (Examples 31 to 37) in which PHAs composed chiefly of a 3-hydroxy-5-[(4-fluorophenyl) sulfanyl]valeric acid unit are produced by culturing a PHA-productive microorganism in a culture medium containing 5-[(4-fluorophenyl)sulfanyl]valeric acid (hereinafter often "FTPxVA").

Example 31

In 200 mL of M9 medium containing 0.5% of polypeptone and 0.1% of FTPxVA, *Pseudomonas cichorii* strain YN2 was inoculated to effect shaking culture at 30° C. and 125 strokes/minute. After 72 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 86 mg of a PHA.

The PHA thus obtained was analyzed by NMR spectroscopy under the same conditions as those in Example 30.

Figure 15:
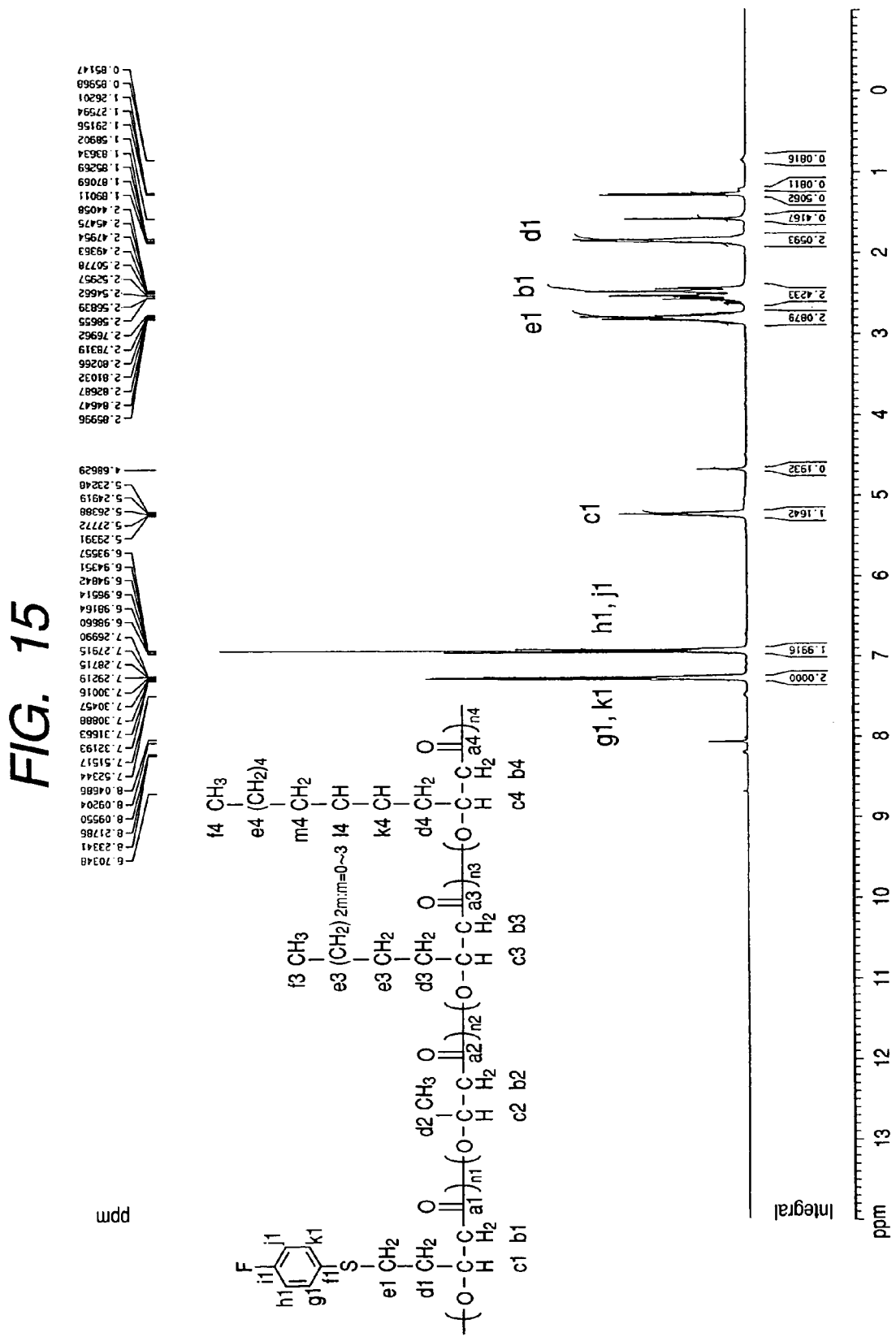
FIG. 15 is a $^1$H-NMR spectrum chart of a PHA obtained according to Example 31.

The $^1$H-NMR spectrum chart are shown in FIG. 15 and the results of its identification in Table 21. As shown in Table 21, it was ascertained that the PHA was a PHA represented by Chemical Formula (33), containing 3-hydroxy-5-[(4-fluorophenyl)sulfanyl]valeric acid as a monomer unit.

TABLE 21

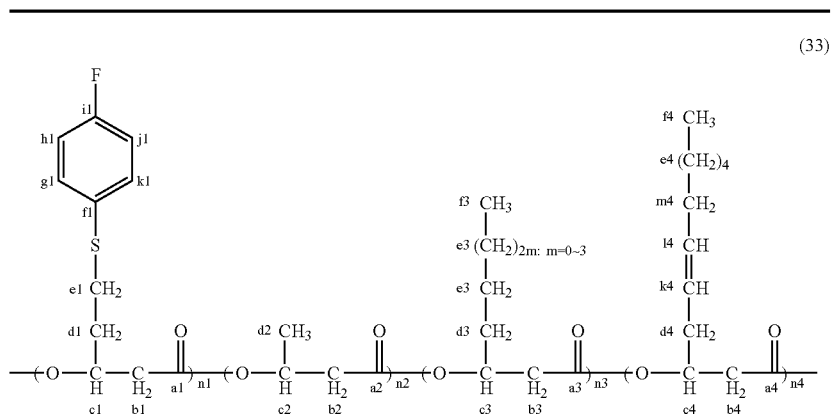

(33)

$^1$H-NMR Spectrum Identification Results (see FIG. 15)

| Chemical shift (ppm) | Integral ratio | Splitting | Identification results |
|---|---|---|---|
| 1.86 | 2 | m | d1 |
| 2.52 | 2 | m | b1 |
| 2.82 | 2 | m | e1 |
| 5.26 | 1 | m | c1 |
| 6.95 | 2 | m | h1, j1 |
| 7.30 | 2 | m | g1, k1 |

The PHA thus obtained was further subjected to methanolysis by a conventional method, and thereafter analyzed with a gas chromatography mass spectrometer (GC-MS, Shimadzu QP-5050, EI method) to make identification of the methyl-esterified product of the PHA monomer unit. The results are shown in Table 22.

The molecular weight of this PHA was also measured by gel permeation chromatography (GPC: Toso HLC-8220; column: Toso TSK-GEL Super HM-H; solvent: chloroform; in terms of polystyrene). As the result, it had Mn (number-average molecular weight) of 95,600 and Mw (weight-average molecular weight) of 291,300.

TABLE 22

| Production of PHA by *Pseudomonas cichorii* Strain YN2 | |
| --- | --- |
| Bacterial-body dry weight | 960 mg/L |
| Polymer dry weight | 430 mg/L |
| Polymer dry weight/bacterial-body dry weight | 44.8% |
| Monomer unit composition (peak area ratio): | |
| 3-Hydroxybutyric acid | 14.2% |
| 3-Hydroxyhexanoic acid | 0.0% |
| 3-Hydroxyoctanoic acid | 0.0% |
| 3-Hydroxydecanoic acid | 0.0% |
| 3-Hydroxydodecanoic acid | 0.0% |
| 3-Hydroxydodecenoic acid | 0.0% |
| 3-Hydroxy-5-(4-fluorothiophenoxy)valeric acid | 85.8% |

Example 32

In 200 mL of M9 medium containing 0.5% of polypeptone and 0.1% of FTPxVA, *Pseudomonas cichorii* strain H45 was inoculated to effect shaking culture at 30° C. and 125 strokes/minute. After 72 hours, the bacterial body was collected by centrifugation, and then washed once with cold methanol, followed by freeze-drying.

The resultant freeze-dried pellets were suspended in 20 mL of chloroform, which were then Stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 44 mg of a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. The results are shown in Table 23.

As shown in Table 23, it was ascertained that the PHA was the PHA represented by Chemical Formula (36), containing 3-hydroxy-5-(4-fluorothiophenoxy)valeric acid as a monomer unit.

TABLE 23

| Production of PHA by *Pseudomonas cichorii* Strain H45 | |
| --- | --- |
| Bacterial-body dry weight | 710 mg/L |
| Polymer dry weight | 220 mg/L |
| Polymer dry weight/bacterial-body dry weight | 31.0% |
| Monomer unit composition (peak area ratio): | |
| 3-Hydroxybutyric acid | 7.5% |
| 3-Hydroxyhexanoic acid | 0.0% |
| 3-Hydroxyoctanoic acid | 0.0% |
| 3-Hydroxydecanoic acid | 0.0% |

TABLE 23-continued

| Production of PHA by *Pseudomonas cichorii* Strain H45 | |
| --- | --- |
| 3-Hydroxydodecanoic acid | 0.0% |
| 3-Hydroxydodecenoic acid | 0.0% |
| 3-Hydroxy-5-(4-fluorothiophenoxy)valeric acid | 92.5% |

Example 33

In 200 mL of M9 medium containing 0.5% of polypeptone and 0.1% of FTPxVA, *Pseudomonas jessenii* strain P161 was inoculated to effect shaking culture at 30° C. and 125 strokes/minute. After 72 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 45 mg of a PHA.

Figure 16:
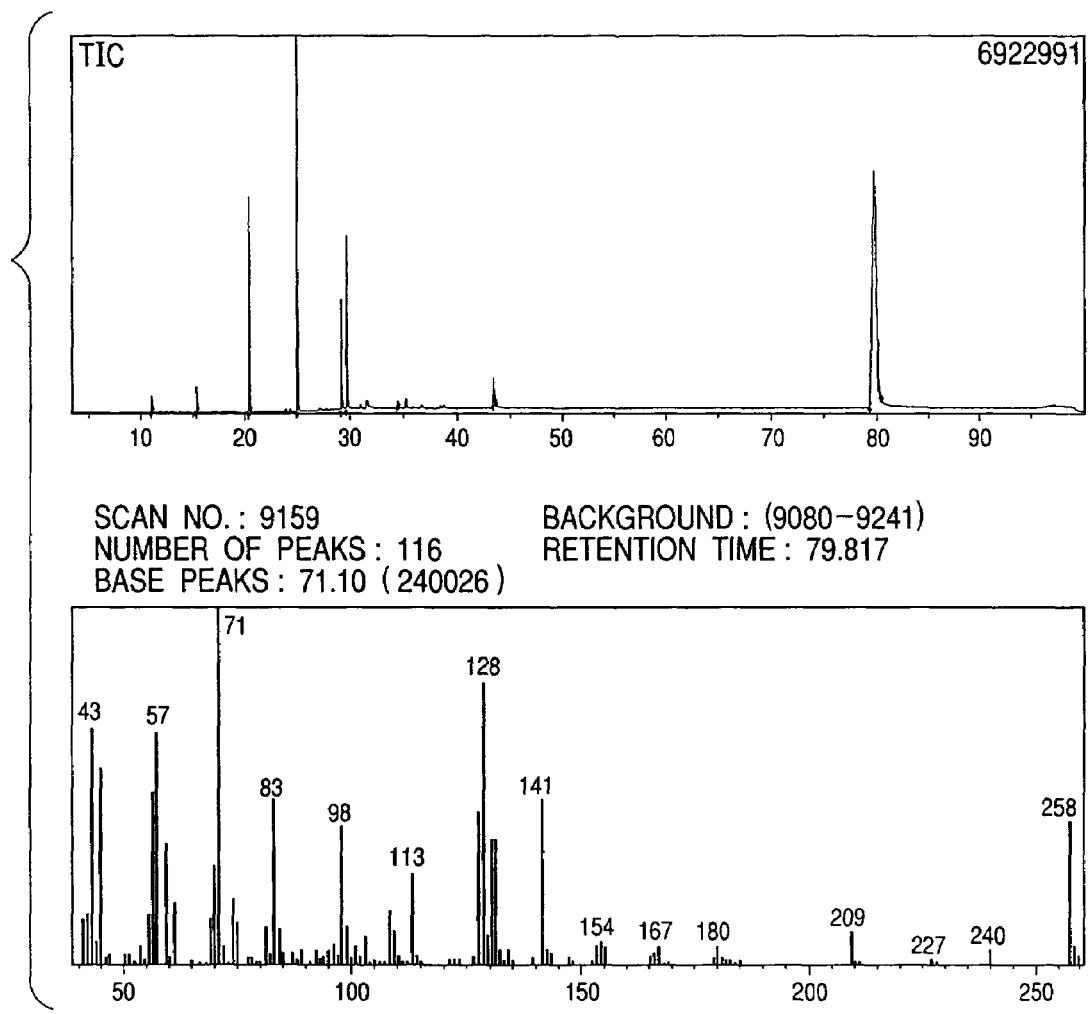
FIG. 16 is TIC of GC-MS on a PHA obtained according to Example 33 and subjected to methanolysis treatment, and an MS spectrum of methyl 3-hydroxy-5-[(4-fluorophenyl)sulfanyl]valerate.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. The results are shown in FIG. 16 and Table 24.

As shown in Table 24, it was ascertained that the PHA was the PHA represented by Chemical Formula (36), containing 3-hydroxy-5-(4-fluorothiophenoxy)valeric acid (hereinafter often "3HFTPxV") as a monomer unit.

TABLE 24

| Production of PHA by *Pseudomonas jessenii* Strain P161 | |
| --- | --- |
| Bacterial-body dry weight | 975 mg/L |
| Polymer dry weight | 225 mg/L |
| Polymer dry weight/bacterial-body dry weight | 26.2% |
| Monomer unit composition (peak area ratio): | |
| 3-Hydroxybutyric acid | 0.5% |
| 3-Hydroxyhexanoic acid | 0.0% |
| 3-Hydroxyoctanoic acid | 0.4% |
| 3-Hydroxydecanoic acid | 0.4% |
| 3-Hydroxydodecanoic acid | 0.0% |
| 3-Hydroxydodecenoic acid | 0.0% |
| 3-Hydroxy-5-(4-fluorothiophenoxy)valeric acid | 98.7% |

Example 34

In 200 mL of M9 medium containing 0.5% of D-glucose and 0.1% of FTPxVA, *Pseudomonas cichorii* strain YN2 was inoculated to effect shaking culture at 30° C. and 125 strokes/minute. After 12 hours, the bacterial body was collected by centrifugation, and then again suspended in 200 mL of M9 medium containing 0.5% of D-glucose and 0.1% of FTPxVA and not containing any nitrogen source (NH₄Cl), further followed by shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 180 mg of a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. The results are shown in Table 25.

As shown in Table 25, it was ascertained that the PHA was the PHA represented by Chemical Formula (36), containing 3HFTPxV as a monomer unit.

TABLE 25

Production of PHA by *Pseudomonas cichorii* Strain YN2

| | |
|---|---|
| Bacterial-body dry weight | 1,630 mg/L |
| Polymer dry weight | 900 mg/L |
| Polymer dry weight/bacterial-body dry weight | 55.2% |
| Monomer unit composition (peak area ratio): | |
| 3-Hydroxybutyric acid | 0.5% |
| 3-Hydroxyhexanoic acid | 0.8% |
| 3-Hydroxyoctanoic acid | 6.6% |
| 3-Hydroxydecanoic acid | 11.8% |
| 3-Hydroxydodecanoic acid | 3.7% |
| 3-Hydroxydodecenoic acid | 6.5% |
| 3-Hydroxy-5-(4-fluorothiophenoxy)valeric acid | 70.1% |

Example 35

In 200 mL of M9 medium containing 0.5% of D-glucose and 0.1% of FTPxVA, *Pseudomonas cichorii* strain H45 was inoculated to effect shaking culture at 30° C. and 125 strokes/minute. After 72 hours, the bacterial body was collected by centrifugation, and then again suspended in 200 mL of M9 medium containing 0.5% of D-glucose and 0.1% of FTPxVA and not containing any nitrogen source ($NH_4Cl$), further followed by shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 169 mg of a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. The results are shown in Table 26.

As shown in Table 26, it was ascertained that the PHA was the PHA represented by Chemical Formula (36), containing 3HFTPxV as a monomer unit.

TABLE 26

Production of PHA by *Pseudomonas cichorii* Strain H45

| | |
|---|---|
| Bacterial-body dry weight | 1,445 mg/L |
| Polymer dry weight | 840 mg/L |
| Polymer dry weight/bacterial-body dry weight | 58.1% |
| Monomer unit composition (peak area ratio): | |
| 3-Hydroxybutyric acid | 10.6% |
| 3-Hydroxyhexanoic acid | 0.7% |
| 3-Hydroxyoctanoic acid | 7.7% |
| 3-Hydroxydecanoic acid | 14.9% |
| 3-Hydroxydodecanoic acid | 3.8% |
| 3-Hydroxydodecenoic acid | 5.0% |
| 3-Hydroxy-5-(4-fluorothiophenoxy)valeric acid | 57.3% |

Example 36

In 200 mL of M9 medium containing 0.5% of D-glucose and 0.1% of FTPxVA, *Pseudomonas jessenii* strain P161 was inoculated to effect shaking culture at 30° C. and 125 strokes/minute. After 72 hours, the bacterial body was collected by centrifugation, and then again suspended in 200 mL of M9 medium containing 0.5% of D-glucose and 0.1% of FTPxVA and not containing any nitrogen source ($NH_4Cl$), further followed by shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 143 mg of a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. The results are shown in Table 27.

As shown in Table 27, it was ascertained that the PHA was the PHA represented by Chemical Formula (36), containing 3HFTPxV as a monomer unit.

TABLE 27

Production of PHA by *Pseudomonas jessenii* Strain P161

| | |
|---|---|
| Bacterial-body dry weight | 1,105 mg/L |
| Polymer dry weight | 715 mg/L |
| Polymer dry weight/bacterial-body dry weight | 64.7% |
| Monomer unit composition (peak area ratio): | |
| 3-Hydroxybutyric acid | 0.0% |
| 3-Hydroxyhexanoic acid | 0.7% |
| 3-Hydroxyoctanoic acid | 5.3% |
| 3-Hydroxydecanoic acid | 12.2% |
| 3-Hydroxydodecanoic acid | 2.9% |
| 3-Hydroxydodecenoic acid | 3.8% |
| 3-Hydroxy-5-(4-fluorothiophenoxy)valeric acid | 75.1% |

Examples are given below (Examples 37 to 47) in which PHAs composed chiefly of a 3-hydroxy-5-[(4-fluorophenyl)sulfanyl]butyric acid unit are produced by culturing a PHA-productive microorganism in a culture medium containing 4-[(4-fluorophenyl)sulfanyl]butyric acid (hereinafter often "FTPxBA").

Example 37

In 200 mL of M9 medium containing 0.5% of D-glucose and 0.1% of FTPxBA, *Pseudomonas cichorii* strain YN2 was inoculated to effect shaking culture at 30° C. and 125 strokes/minute. After 96 hours, the bacterial body was collected by centrifugation, and then again suspended in 200 mL of M9 medium containing 0.5% of D-glucose and 0.1% of FTPxBA and not containing any nitrogen source ($NH_4Cl$), further followed by shaking culture at 30° C. and 125 strokes/minute. After 72 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 64 mg of a PHA.

The PHA thus obtained was analyzed by NMR spectroscopy under the following conditions.

—Measuring Instrument—

FT-NMR: Bruker DPX400.

Resonance frequency: $^1H$=400 MHz, $^{13}C$=100 MHz.

—Measuring Instrument—

Measurement nuclides: $^1H$, $^{13}C$

Solvent used: $CDCl_3$.

Reference: Capillary-encapsulated TMS/$CDCl_3$.

Measurement temperature: room temperature.

Figure 17:
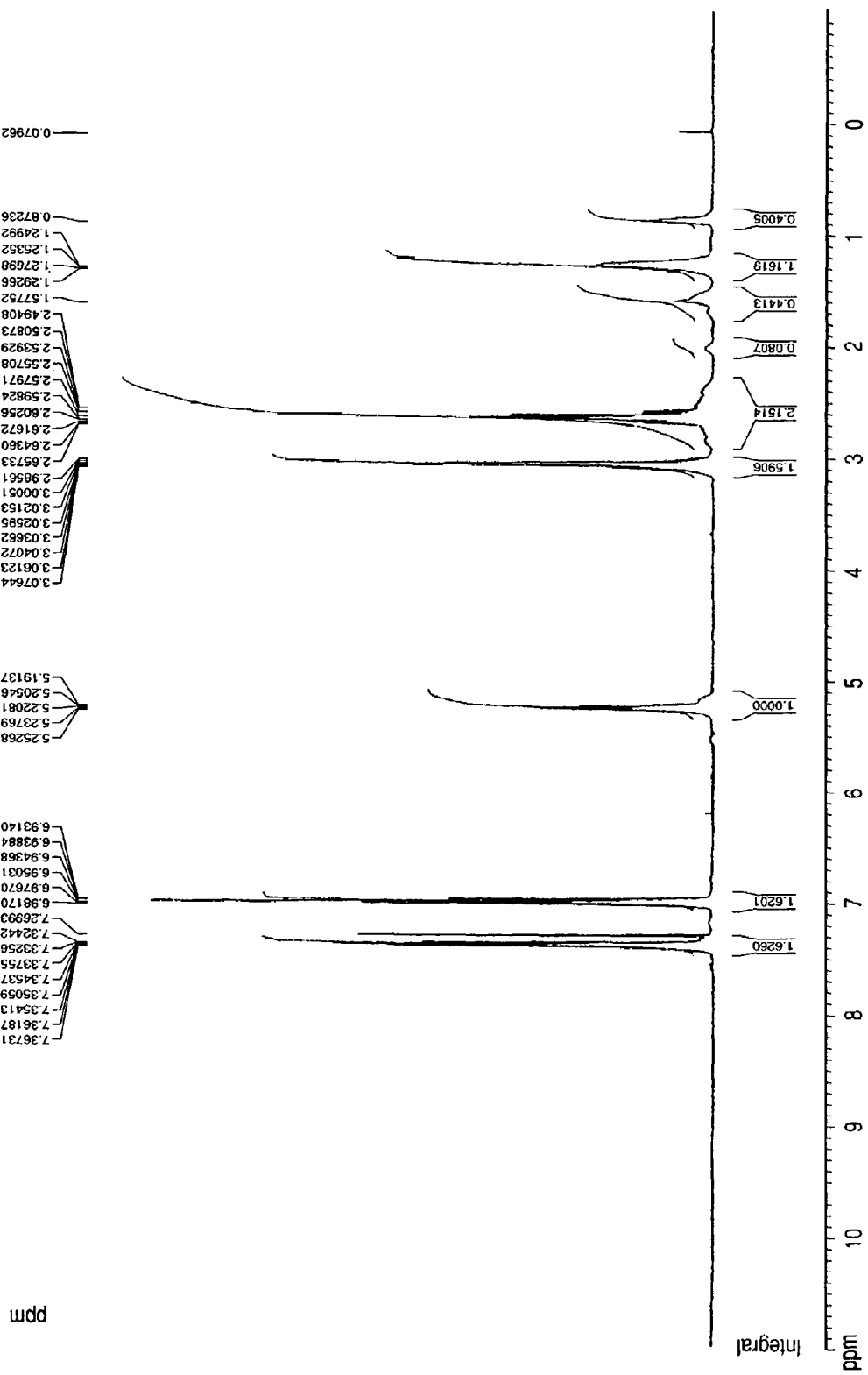
FIG. 17 is a $^1$H-NMR spectrum chart of a PHA obtained according to Example 37.
Figure 18:
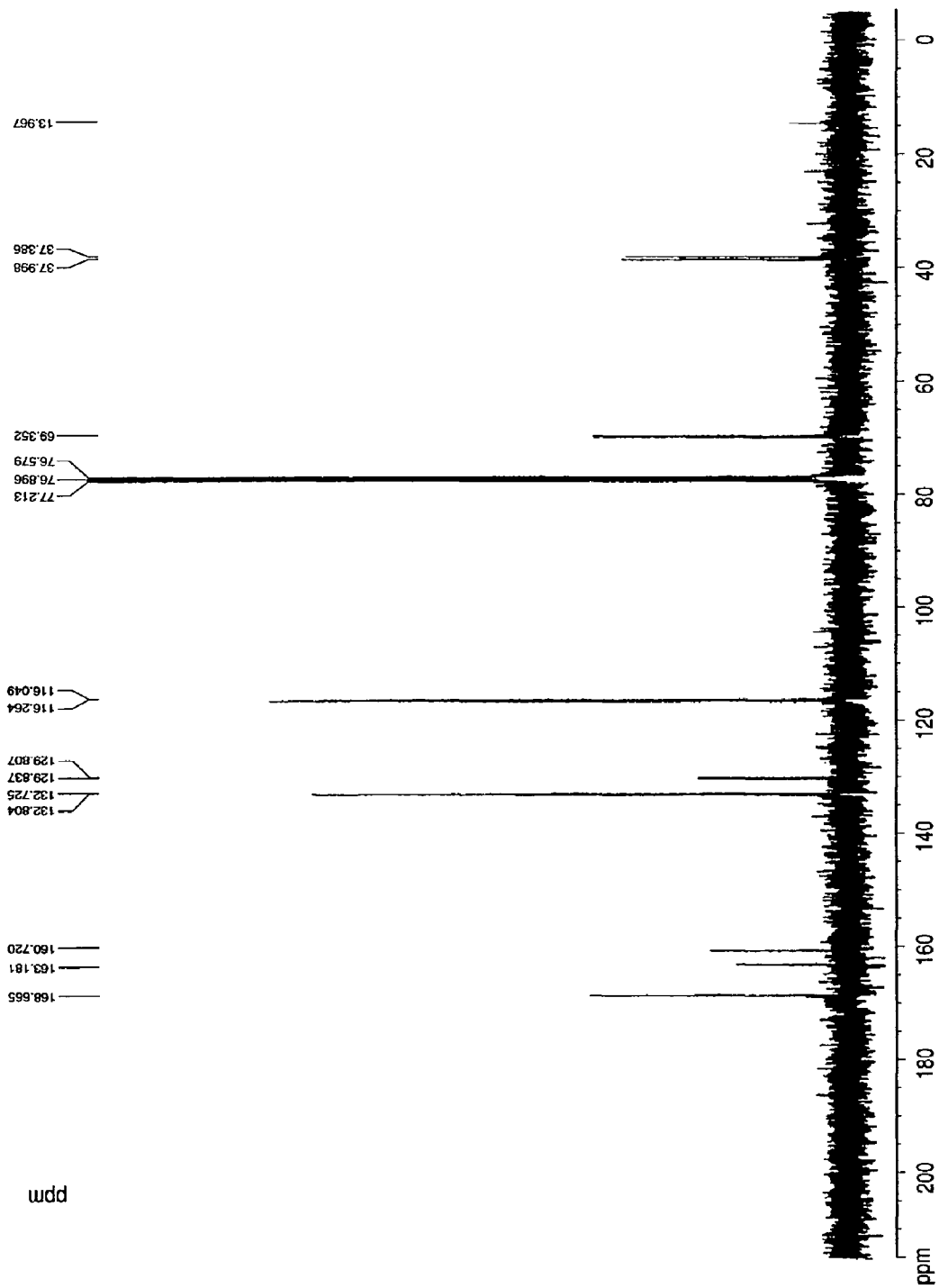
FIG. 18 is a $^{13}$C-NMR spectrum chart of a PHA obtained according to Example 37.

The $^1H$-NMR and $^{13}C$-NMR spectrum charts are shown in FIGS. 17 and 18, respectively, and the results of their identification in Tables 28 and 29, respectively.

TABLE 28

$^1H$-NMR Spectrum Identification Results

| Chemical shift (ppm) | Integral ratio | Splitting | Identification results |
|---|---|---|---|
| 2.59 | 2 | m | c1 |
| 3.03 | 2 | m | b1 |
| 5.22 | 2 | quint | d1 |
| 6.96 | 2 | m | g1, i1 |
| 7.35 | 2 | m | f1, j1 |

TABLE 29

$^{13}C$-NMR Spectrum Identification Results

| Chemical shift (ppm) | Splitting | Identification results |
|---|---|---|
| 37.4 | s | b1 or c1 |
| 38.0 | s | b1 or c1 |
| 69.4 | s | d1 |
| 116.0 & 116.3 | d | g1, i1 |
| 129.8 & 129.8 | d | e1 |
| 132.7 & 132.8 | d | f1, j1 |
| 160.7 & 163.1 | d | h1 |
| 168.7 | s | a1 |

As shown in Tables 28 and 29, it was ascertained that the PHA was a PHA represented by Chemical Formula (34), containing 3-hydroxy-4-[(4-fluorophenyl)sulfanyl]butyric acid as a monomer unit. It was also found from the NMR spectroscopy that the resultant PHA contained the monomer unit 3-hydroxy-4-[(4-fluorophenyl)sulfanyl]butyric acid (3HTPxB) in an amount of 79.5 mol %.

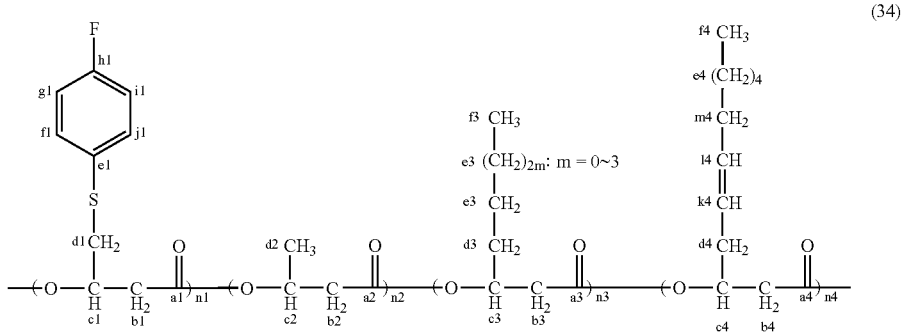

(34)

The molecular weight of the PHA obtained was also measured by gel permeation chromatography (GPC: Toso HLC-8220; column: Toso TSK-GEL Super HM-H; solvent: chloroform; in terms of polystyrene). As the result, it had Mn of 19,800 and Mw of 41,500.

Example 38

In 2.00 mL of M9 medium containing 0.5% of D-glucose and 0.1% of FTPxBA, *Pseudomonas cichorii* strain H45 was inoculated to effect shaking culture at 30° C. and 125 strokes/minute. After 96 hours, the bacterial body was collected by centrifugation, and then again suspended in 200 mL of M9 medium containing 0.5% of D-glucose and 0.1% of FTPxBA and not containing any nitrogen source ($NH_4Cl$), further followed by shaking culture at 30° C. and 125 strokes/minute. After 72 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 4 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl) sulfanyl]butyric acid in an amount of 78.9 mol %.

Example 39

In 200 mL of M9 medium containing 0.5% of D-glucose and 0.1% of FTPxBA, *Pseudomonas jessenii* strain P161 was inoculated to effect shaking culture at 30° C. and 125 strokes/minute. After 96 hours, the bacterial body was collected by centrifugation, and then again suspended in 200 mL of M9 medium containing 0.5% of D-glucose and 0.1% of FTPxBA and not containing any nitrogen source ($NH_4Cl$), further followed by shaking culture at 30° C. and 125 strokes/minute. After 72 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 6 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl) sulfanyl]butyric acid in an amount of 73.4 mol %.

Example 40

In 200 mL of M9 medium containing 0.5% of polypeptone and 0.1% of FTPxBA, *Pseudomonas cichorii* strain YN2 was inoculated to effect shaking culture at 30° C. and 125 strokes/minute. After 48 hours, the bacterial body was collected by centrifugation, and then again suspended in 200 mL of M9 medium containing 0.5% of sodium pyruvate and 0.1% of FTPxBA and not containing any nitrogen source ($NH_4Cl$), further followed by shaking culture at 30° C. and 125 strokes/minute. After 47 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 76 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl) sulfanyl]butyric acid in an amount of 65.7 mol %.

Example 41

In 200 mL of M9 medium containing 0.5% of polypeptone and 0.1% of FTPxBA, *Pseudomonas cichorii* strain H45 was inoculated to effect shaking culture at 30° C. and 125 strokes/minute. After 48 hours, the bacterial body was collected by centrifugation, and then again suspended in 200 mL of M9 medium containing 0.5% of sodium pyruvate and 0.1% of FTPxBA and not containing any nitrogen source ($NH_4Cl$), further followed by shaking culture at 30° C. and 125 strokes/minute. After 47 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 6 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl) sulfanyl]butyric acid in an amount of 53.7 mol %.

Example 42

In 200 mL of M9 medium containing 0.5% of polypeptone and 0.1% of FTPxBA, *Pseudomonas jessenii* strain P161 was inoculated to effect shaking culture at 30° C. and 125 strokes/minute. After 48 hours, the bacterial body was collected by centrifugation, and then again suspended in 200 mL of M9 medium containing 0.5% of sodium pyruvate and 0.1% of FTPxBA and not containing any nitrogen source ($NH_4Cl$), further followed by shaking culture at 30° C. and 125 strokes/minute. After 47 hours, the bacterial body was collected by centrifugation, and then washed once with cold methanol, followed by freeze-drying.

The resultant freeze-dried pellets were suspended in 20 mL of chloroform, which were then stirred at −60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 7 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl) sulfanyl]butyric acid in an amount of 35.8 mol %.

Example 43

In 200 mL of M9 medium containing 0.5% of sodium glutamate and 0-0.1% of FTPxBA, *Pseudomonas cichorii* strain H45 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 14 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl)sulfanyl]butyric acid in an amount of 18.7 mol %.

Example 44

In 200 mL of M9 medium containing 0.5% of polypeptone and 0.1% of FTPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 6 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl)sulfanyl]butyric acid in an amount of 44.6 mol %.

Example 45

In 200 mL of M9 medium containing 0.5% of yeast extract and 0.1% of FTPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 10 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl)sulfanyl]butyric acid in an amount of 56.8 mol %.

Example 46

In 200 mL of M9 medium containing 0.1% of n-nonanoic acid and 0.1% of FTPxBA, *Pseudomonas cichorii* strain YN2 was inoculated to effect shaking culture at 30° C. and 1.25 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 38 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl)sulfanyl]butyric acid in an amount of 5.2 mol %.

Example 47

In 200 mL of M9 medium containing 0.1% of n-octanoic acid and 0.1% of FTPxBA, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain 34 mg of a PHA.

The PHA thus obtained was analyzed by NMR spectroscopy under the same conditions as those in Example 37. As the result, it was found therefrom that the resultant PHA contained the monomer unit 3-hydroxy-4-[(4-fluorophenyl)sulfanyl]butyric acid in an amount of 6.0 mol %.

Table 30 shows the bacterial-body dry weight, polymer dry weight and polymer dry weight/bacterial body dry weight and the mol % of the 3HTPxB unit of the polymer obtained in each of Examples 37 to 47.

TABLE 30

| | Bacterial-body dry weight (mg/L) | Polymer dry weight (mg/L) | Polymer dry weight/ Bacterial-body dry weight (%) | 3HTPxB unit mol % |
|---|---|---|---|---|
| Example 37 | 720 | 320 | 44.4 | 79.5 |
| Example 38 | 435 | 20 | 4.6 | 78.9 |
| Example 39 | 390 | 30 | 7.7 | 73.4 |
| Example 40 | 920 | 350 | 38.0 | 65.7 |
| Example 41 | 470 | 30 | 6.4 | 53.7 |
| Example 42 | 405 | 35 | 7.4 | 35.8 |
| Example 43 | 785 | 90 | 11.5 | 18.7 |
| Example 44 | 575 | 30 | 5.2 | 44.6 |
| Example 45 | 710 | 50 | 7.0 | 56.8 |
| Example 46 | 410 | 190 | 46.3 | 5.2 |
| Example 47 | 400 | 170 | 42.5 | 6.0 |

Example 48

Production of polyhydroxyalkanoate containing 3-hydroxy-5-[(4-sulfophenyl)sulfanyl]valeric acid unit In 200 mL of M9 medium containing 0.5% of polypeptone, *Pseudomonas cichorii* strain YN2 was inoculated to effect shaking culture in a 500 mL shaking flask under conditions of 30° C. and 125 strokes/minute. After 6 hours, 2 mL of the resultant culture solution was added to 200 mL of M9 medium containing 0.5% of polypeptone and 0.1% of 5-(phenylsulfanyl)valeric acid to effect second-stage shaking culture in a 2,000 mL shaking flask under conditions of 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 1,070 mg of a polyhydroxyalkanoate.

The polyhydroxyalkanoate thus obtained was analyzed by NMR spectroscopy under the following conditions.
—Measuring Instrument—
FT-NMR: Bruker DPX400.
Resonance frequency: $^1$H=400 MHz.
—Measuring Instrument—
Measurement nuclide: $^1$H.
Solvent used: $CDCl_3$.
Measurement temperature: room temperature.

As the result, it was ascertained that the polyhydroxyalkanoate thus obtained was a polyhydroxyalkanoate containing a 3-hydroxy-5-(phenylsulfanyl)valeric acid unit as a monomer unit and also containing, as monomers other than that, 3-hydroxyalkanoic acids or 3-hydroxyalkenoic acids which were saturated or unsaturated fatty acids having 4 to 12 carbon atoms, such as 3-hydroxybutyric acid and 3-hydroxyvaleric acid. It was also found from the NMR spectroscopy that the resultant polyhydroxyalkanoate contained the monomer unit 3-hydroxy-5-(phenylsulfanyl)valeric acid in an amount of 94.7 mol %.

Into a 100 mL eggplant type flask, 500 mg of the polyhydroxyalkanoate containing a 3-hydroxy-5-(phenylsulfanyl)valeric acid unit, obtained as described above, and 35 mL of chloroform were previously charged, and the temperature was set at 0° C. Then, 1.80 mL (27.0 mmol) was dropwise little by little added thereto keeping the reaction temperature at 0° C. At the same temperature the reaction mixture was stirred for 2 hours, and thereafter the reaction product coming insoluble was taken out by filtration. The reaction product was stirred in 300 mL of ice water, and thereafter collected by filtration, followed by washing with methanol. After the filtration, the filtrate was dried to obtain 230 mg of a polyhydroxyalkanoate containing a 3-hydroxy-5-[(4-sulfophenyl)sulfannyl]valeric acid unit, with the sulfonic acid having been introduced.

The compound thus obtained was analyzed by NMR spectroscopy under the following conditions.
—Measuring Instrument—
FT-NMR: Bruker DPX400.
Resonance frequency: $^1$H =400 MHz.
—Measuring Instrument—
Measurement nuclide: $^1$H.
Solvent used: $DMSO-d_6$+5% $D_2O$.
Measurement temperature: 40° C.+.

The results of identification of the $^1$H-NMR spectrum chart are shown in Table 31.

This PHA was further analyzed by Fourier transform-infrared absorption (FT-IR) spectroscopy (Necolet AVATAR360 FT-IR). As the result, absorption due to sulfonic acid was additionally seen at 1,169 $cm^{-1}$.

From these results, it was ascertained that this PHA was a PHA represented by Chemical Formula (35), containing 3-hydroxy-5-[(4-sulfophenyl)sulfanyl]valeric acid unit.

TABLE 31

$^1$H-NMR Spectrum Identification Results

| Chemical shift (ppm) | Integral ratio | Splitting | Identification results |
|---|---|---|---|
| 1.63 to 1.82 | 2 | br | d1 |
| 2.54 to 2.63 | 2 | br | b1 |
| 2.87 to 3.04 | 2 | br | e1 |
| 5.16 | 1 | br | c1 |
| 7.24 | 2 | d | h1, j1 |
| 7.51 | 2 | d | g1, k1 |

Example 49

Production of polyhydroxyalkanoate containing 3-hydroxy-6-[(4-carboxyphenyl)sulfanyl]hexanoic acid unit 4 L of M9 medium containing 0.1% of n-nonanoic acid and 0.1% of 8-bromooctanoic acid (available from Tokyo. Kasei Co., Ltd.) was dividedly put into four 2-L-vol shaking flasks in an amount of 1 L each, and *Pseudomonas cichorii* strain YN2 was inoculated to each of them to effect shaking culture at 30° C. and 125 strokes/minute. After 96 hours, the bacterial body was collected by centrifugation, and then washed once with cold methanol, followed by freeze-drying.

The resultant freeze-dried pellets were suspended in 100 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain 370 mg of a PHA.

The PHA thus obtained was analyzed by NMR spectroscopy under the following conditions.
—Measuring Instrument—
FT-NMR: Bruker DPX400.
Resonance frequency: $^1H$=400 MHz, $^{13}C$=100 MHz.
—Measuring Instrument—
Measurement nuclides: $^1H$, $^{13}C$.
Solvent used: $CDCl_3$.
Measurement temperature: room temperature.

In the $^1H$-NMR spectrum, a peak due to the protons of the side-chain terminal —$CH_2Br$ was seen at 3.4 ppm vicinity, and, from its integral ratio, the unit having the terminal bromo group was found to be in a proportion of 32 mol %.

In the $^{13}C$-NMR spectrum, peaks of the side-chain terminal methine were seen at 60.8 ppm and 70.6 ppm in addition to a peak (70.8 ppm) due to a straight-chain 3-hydroxyalkanoic acid unit synthesized from the n-nonanoic acid. These peaks were considered to be due to a 3-hydroxy-6-bromohexanoic acid unit and a 3-hydroxy-8-bromooctanoic acid unit, respectively.

The above results proved that the resultant PHA was a PHA containing the 3-hydroxy-6-bromohexanoic acid unit and the 3-hydroxy-8-bromooctanoic acid unit in an amount of 32 mol % in total.

This PHA was dissolved in 3 mL of DMF, and a solution prepared by dissolving 200 mg of 4-mercaptobenzoic acid (available from Tokyo Kasei Co., Ltd.) in 1 mL of DMF was added thereto, where 150 μL of diethylamine was dropwise added with stirring. The mixture formed was stirred for 24 hours at room temperature, and thereafter the reaction mixture was added to ice lumps. At the time the ice lamps became water substantially, dilute hydrochloric acid was dropwise added thereto with stirring. The precipitate obtained was collected by centrifugation and then dried under reduced pressure at room temperature. Thereafter, the resultant dried matter was again dissolved in 3 mL of DMF, and the solution was added to ice lumps. At the time the ice lamps became water substantially, dilute hydrochloric acid was dropwise added thereto with stirring. The precipitate obtained was collected by centrifugation (here, the unreacted 4-mercaptobenzoic acid coming deposited in a powdery form was carefully removed) and then dried under reduced pressure at room temperature to obtain a PHA, which was in an amount of 260 mg.

The PHA thus obtained was analyzed by $^1H$-NMR Spectroscopy under the following conditions.
—Measuring Instrument—
FT-NMR: Bruker DPX400.
Resonance frequency: 1H=400 MHz.
—Measuring Instrument—
Measurement nuclide: $^1H$.
Solvent used: $DMSO-d_6$+5% $D_2O$.
Measurement temperature: 40° C.+.

Equivalent peaks of the protons at the ortho-position and meta-position of the aromatic ring were seen at 7.2 ppm and 7.8 ppm vicinities. Also, the peak due to the protons of the side-chain terminal —$CH_2Br$ had disappeared, and a peak due to the protons of the methylene moiety of the —S—$CH_2$— structure appeared at 2.9 ppm vicinity. Also, it was calculated from the integral ratio of peaks that the unit having the aromatic ring was in a proportion of 35 mol %.

This PHA was further analyzed by FT-IR spectroscopy in the same manner as in Example 48. As the result, the absorption due to carboxylic acid was seen at 1,685 $cm^{-1}$.

From the above results, it was ascertained that the resultant PHA contained in the molecule a 3-hydroxy-8-[(4-carboxyphenyl)sulfanyl)octanoic acid unit represented by Chemical Formula (10) and a 3-hydroxy-6-[(4-carboxyphenyl)sulfanyl]hexanoic acid unit represented by Chemical Formula (11).

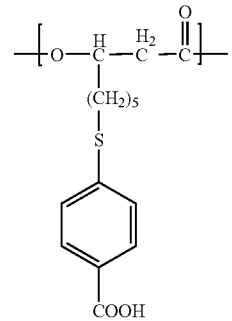

(10)

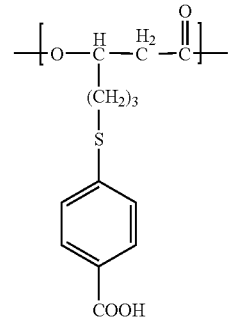

(11)

Example 50

1.0694 g of 3-hydroxy-5-phenylvaleric acid, 0.6693 g of 8-bromooctanoic acid (available from Tokyo Kasei Co., Ltd.) and 5.0 g of polypeptone were taken into a shaking flask, and 1,000 mL of M9 medium was put thereinto. The flask was stoppered with a cap, followed by sterilization with heating at 120° C. for 10 minutes by means of an autoclave.

After cooling to room temperature, 5 mL of a bacterial liquid having been prepared (one prepared by inoculating *Pseudomonas cichorii* P161 into M9 medium solution containing 0.5% of polypeptone and having been pre-cultured for 8 hours) was added to effect shaking culture at 30° C. and 125 strokes/minute. After 72 hours, the bacterial body was collected by centrifugation, and then washed with methanol, followed by drying by means of a vacuum pump.

This dried bacterial body was further suspended in an appropriate quantity of chloroform, which were then stirred at room temperature for 72 hours to extract a PHA. The liquid extract obtained was filtered with a membrane filter of 0.45 μm in pore diameter, and thereafter concentrated by means of a rotary evaporator. The concentrated liquid was re-precipitated in methanol. The polymer thus obtained was vacuum-dried and the yield of the polymer was measured to find that it was 254 mg/L.

The PHA thus obtained was analyzed by NMR spectroscopy under the following conditions.
—Measuring Instrument—
FT-NMR: Bruker DPX400.
Resonance frequency: $^1H$ =400 MHz, $^{13}C$=100 MHz.
—Measuring Instrument—
Measurement nuclides: $^1H$.
Solvent used: $CDCl_3$.
Measurement temperature: room temperature.

Figure 19:
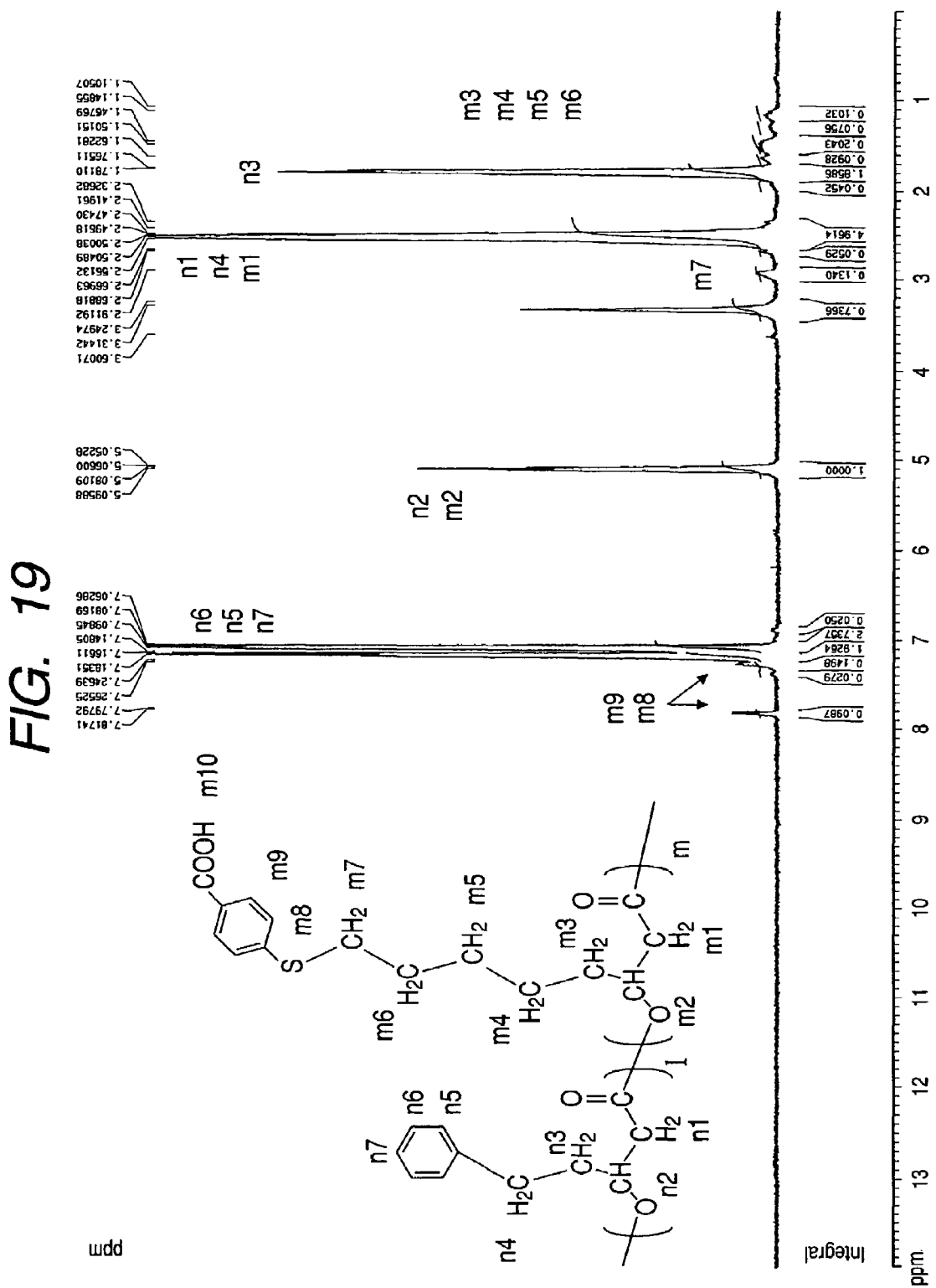
FIG. 19 is a $^1$H-NMR spectrum chart of a PHA obtained according to Example 50.

In the $^1H$-NMR spectrum, as shown in FIG. 19, a peak due to the protons of the side-chain terminal —$CH_2Br$ was seen at 3.4 ppm vicinity, and, from its integral ratio, the unit having the terminal bromo group was found to be in a proportion of 7 mold %.

The above results proved that the resultant PHA was a PHA containing a 3-hydroxy-6-bromohexanoic acid unit and a 3-hydroxy-8-bromooctanoic acid unit in an amount of 7 mol % in total.

800 mg of this PHA was dissolved in 3 mL of DMF, and a solution prepared by dissolving 73 mg of 4-mercaptobenzoic acid (available from Tokyo Kasei Co., Ltd.) in 3 mL of DMF was added thereto, where 49 μL of diethylamine was dropwise added with stirring. The mixture formed was stirred for 63 hours at room temperature, and thereafter the reaction mixture was added to ice lumps. At the time the ice lamps became water substantially, dilute hydrochloric acid was dropwise added thereto with stirring. The precipitate obtained was collected by centrifugation and then dried under reduced pressure at room temperature. Thereafter, the resultant dried matter was dissolved in 20 mL of DMF, and the solution was added to methanol. The precipitate obtained was collected by centrifugation and then dried under reduced pressure at room temperature to obtain a PHA, which was in an amount of 250 mg.

The PHA thus obtained was analyzed by $^1H$-NMR spectroscopy under the following conditions.
—Measuring Instrument—
FT-NMR: Bruker DPX400.
Resonance frequency: $^1H$ 400 MHz.
—Measuring Instrument—
Measurement nuclide: $^1H$.
Solvent used: DMSO-$d_6$.
Measurement temperature: 40° C.+.

Equivalent peaks of the protons at the ortho-positions and meta-positions of the aromatic rings of a 3-hydroxy-8-[(4-carboxyphenyl sulfanyl)octanoic acid unit represented by Chemical Formula (10) and a 3-hydroxy-6-[(4-carboxyphenyl)sulfanyl)hexanoic acid unit represented by Chemical Formula (11) were seen at 7.2 ppm and 7.8 ppm vicinities. Also, the peak due to the protons of the side-chain terminal —$CH_2Br$ had disappeared, and a peak due to the protons of the methylene moiety of the —S—$CH_2$— structure appeared at 2.9 ppm vicinity. Peaks due to the aromatic ring of a 3-hydroxy-5-phenylvaleric acid unit were also seen at 7.1 ppm and 7.2 ppm vicinities.

This PHA was further analyzed by FT-IR spectroscopy in the same manner as in Example 48. As the result, the absorption due to carboxylic acid was seen at 1,695 $cm^{-1}$.

From the above results, it was ascertained that the resultant PHA contained a 3-hydroxy-5-phenylvaleric acid unit represented by Chemical Formula (12) and contained a 3-hydroxy-8-[(4-carboxyphenyl)sulfanyl)octanoic acid unit represented by Chemical Formula (10) or a 3-hydroxy-6-[(4-carboxyphenyl)sulfanyl)hexanoic acid unit represented by Chemical Formula (11).

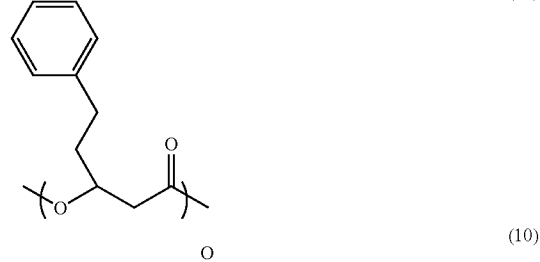

(12)

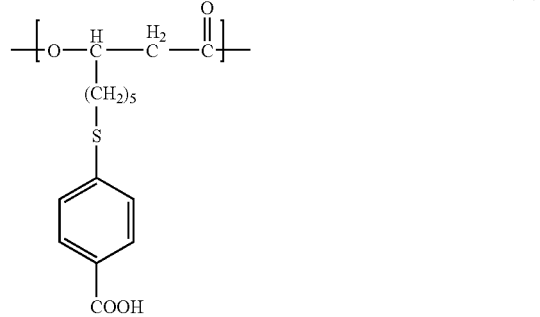

(10)

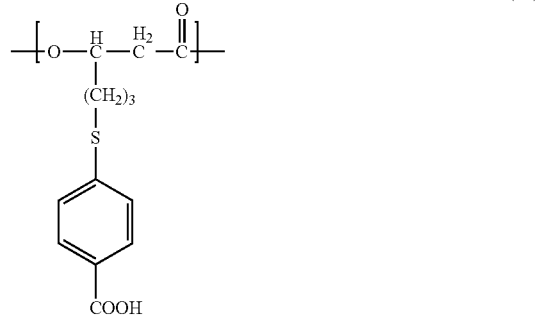

(11)

The compounds obtained in the same manner as in the Examples 48 and 49 were used as exemplified compounds (1) and (2) in Example 51 and the subsequent examples.

Then each kind of toner was produced using charge controlling agent prepared in the same manner as in the Examples 48 and 49 by the method selected from the methods of this invention and evaluation was made (Examples 51 to 82).

Example 51

First $Na_3PO_4$ aqueous solution was introduced into a 2 l flask with four necks equipped with a high speed agitator, TK-Homomixer, the rotary speed of the agitator was adjusted to 10,000 rpm, and the solution was heated to 60° C. Then $CaCl_2$ aqueous solution was added little by little to prepare a water-base dispersing medium containing a very small amount of difficultly water-soluble dispersant $Ca_3(PO_4)_2$.

On the other hand, the composition shown below was dispersed with a ball mill for 3 hours, and 10 parts by mass of surface tack eliminator (ester wax) and 10 parts by mass of polymerization initiator, 2,2'-azobis(2,4-dimethylvaleronitrile), were added to prepare a polymerizable monomer composition.

| | |
|---|---|
| Styrene monomer | 82 parts by mass |
| Ethylhexyl acrylate monomer | 18 parts by mass |
| Divinylbenzene monomer | 0.1 parts by mass |
| Cyan colorant (C.I. pigment Blue 15) | 6 parts by mass |
| Polyethylene oxide resin (molecular weight 3200, acid value 8) | 5 parts by mass |
| Exemplified compound (1) | 2 parts by mass |

Then the polymerizable monomer composition obtained as above was introduced into the previously prepared water-base dispersing medium, and granulation was carried out while maintaining a rotary speed of 10,000 rpm. After that, the polymerizable-monomer composition was reacted at 65° C. for 3 hours and polymerized at 80° C. for 6 hours while agitating the dispersion with paddle agitating elements, and the polymerization reaction was terminated. After terminating the reaction, the suspension was cooled, acid was added to dissolve the difficultly water-soluble dispersant $Ca_3(PO_4)_2$, and filtration, rinsing and drying were carried out to obtain blue polymer particles (1). When measuring the particle size of the obtained blue polymer particles (1) with Kolter Counter Multi-Sizer (by Kolter), the weight-average particle size was 7.0 µm and the amount of the fine powder (the existing rate of the particles of 3.17 µm or smaller in the number distribution) was 5.6% by number.

Then 1.3 parts by mass of finely powdered hydrophobic silica (BET: 270 $m^2/g$) having been treated with hexamethyldisilazane, as a flow improver, was externally attached to 100 parts by mass of the blue polymer particles (1) having been prepared as above by dry mixing with a Henschel mixer, to obtain blue toner (1) of this example. And 7 parts by mass of the blue toner (1) and 93 parts by mass of resin-coated magnetic ferrite carrier (average particle size: 45 µm) were mixed with each other to prepare a two-component blue developer (1) for magnetic brush development.

Example 52

Blue toner (2) of the Example 52 was obtained in the same manner as in the Example 51 except that 2.0 parts by mass of the exemplified compound (2) was used instead of the exemplified compound (1). The properties of the toner were determined in the same manner as in the Example 51 and the results are shown in Table 32. And a two-component blue developer (2) was obtained with this toner in the same manner as in the Example 51.

Comparative Example 1

Blue toner (3) of the Comparative Example 1 was obtained in the same manner as in the Example 51 except that none of the exemplified compounds (1) and (2) were used. The properties of the toner were determined in the same manner as in the Example 51 and the results are shown in Table 32. And a two-component blue developer (3) of the Comparative Example 1 was obtained with this toner in the same manner as in the Example 51.

<Evaluation>

The amount of electrical charge of the toners was measured of two-component blue developers (1), (2) and (3) obtained in the Examples 51 and 52 and in the Comparative Example 1, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 32 together.

(Charging Property)
AA: very good (−20 µC/g or less)
A: good (−19.9 to −10.0 µC/g)
B: practically permissible (−9.9 to −5.0 µC/g)
C: practically impermissible (−4.9 µC/g or more)

TABLE 32

Particle Size Distribution and Charging Property of Blue Toners (1) to (3)

| | | | Particle Size Distribution | | Charging Property | | | |
|---|---|---|---|---|---|---|---|---|
| | | | | | Normal Temperature and Humidity (Q/M) | | High Temperature and Humidity (Q/M) | |
| Example | Exemplified Compound No. | Toner No.: Blue | Weight-Average Particle Size (µm) | Amount of Fine Powder (% by number) | 10-Second Agitation | 300-Second Agitation | 10-Second Agitation | 300-Second Agitation |
| 51 | 1 | 1 | 7.0 | 5.6 | AA | AA | AA | AA |
| 52 | 2 | 2 | 7.1 | 5.5 | AA | AA | AA | AA |
| Comparative Example 1 | — | 3 | 7.0 | 5.2 | C | C | C | C |

Examples 53 and 54

Yellow toners (1) and (2) of the Examples 53 and 54 were obtained using 2.0 parts by mass of the exemplified compounds (1) and (2), respectively, in the same manner as the Example 51 except that a yellow colorant (Hansa yellow G) was used instead of a cyan colorant. The properties of the toners were determined in the same manner as in the Example 51 and the results are shown in Table 33. And two-component yellow developers (1) and (2) were obtained in the same manner as in the Example 51.

Comparative Example 2

Yellow toner (3) of the Comparative Example 2 was obtained in the same manner as in the Example 51 except that no exemplified compounds were used and a yellow colorant (Hansa yellow G) was used instead of a cyan colorant. The properties of the toner were determined in the same manner as in the Example 51 and the results are shown in Table 33. And a two-component yellow developer (3) of the Comparative Example 2 was obtained with this toner in the same manner as in the Example 51.

<Evaluation>

The amount of electrical charge of the toners was measured of two-component yellow developers (1), (2) and (3) obtained in the Examples 53 and 54 and in the Comparative Example 2, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 33 together.

(Charging Property)
  AA: very good (−20 µC/g or less)
  A: good (−19.9 to −10.0 µC/g)
  B: practically permissible (−9.9 to −5.0 µC/g)
  C: practically impermissible (−4.9 µC/g or more)

Examples 55 and 56

Black toners (1) and (2) of the Examples 55 and 56 were obtained using 2.0 parts by mass of the exemplified compounds (1) and (2), respectively, in the same manner as the Example 51 except that carbon black (DBP oil absorption 110 mL/100 g) was used instead of a cyan colorant. The properties of the toners were determined in the same manner as in the Example 51 and the results are shown in Table 34. And two-component black developers (1) and (2) were obtained in the same manner as in the Example 51.

Comparative Example 3

Black toner (3) of the Comparative Example 3 was obtained in the same manner as in the Example 51 except that no exemplified compounds were used and carbon black (DBP-oil absorption 110 mL/1.00 g) was used instead of a cyan colorant. The properties of the toner were determined in the same manner as in the Example 51 and the results are shown in Table 34. And a two-component black developer (3) of the Comparative Example 3 was obtained with this toner in the same manner as in the Example 51.

<Evaluation>

The amount of electrical charge of the toners was measured of two-component black developers (1), (2) and (3) obtained in the Examples 55 and 56 and in the Comparative Example 3, respectively after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 34 together.

(Charging Property)
  AA: very good (−20 µC/g or less)
  A: good (−19.9 to −10.0 µC/g)
  B: practically permissible (−9.9 to −5.0 µC/g)
  C: practically impermissible (−4.9 µC/g or more)

TABLE 33

Particle Size Distribution and Charging Property of Yellow Toners (1) to (3)

| Example | Exemplified Compound No. | Toner No.: Yellow | Particle Size Distribution Weight-Average Particle Size (µm) | Amount of Fine Powder (% by number) | Charging Property Normal Temperature and Humidity (Q/M) 10-Second Agitation | 300-Second Agitation | Charging Property High Temperature and Humidity (Q/M) 10-Second Agitation | 300-Second Agitation |
|---|---|---|---|---|---|---|---|---|
| 53 | 1 | 1 | 6.9 | 5.5 | AA | AA | AA | AA |
| 54 | 2 | 2 | 7.0 | 5.5 | AA | AA | AA | AA |
| Comparative Example 2 | — | 3 | 7.2 | 4.9 | C | C | C | C |

TABLE 34

Particle Size Distribution and Charging Property of Black Toners (1) to (3)

| Example | Exemplified Compound No. | Toner No.: Black | Particle Size Distribution Weight-Average Particle Size (μm) | Amount of Fine Powder (% by number) | Charging Property Normal Temperature and Humidity (Q/M) 10-Second Agitation | 300-Second Agitation | High Temperature and Humidity (Q/M) 10-Second Agitation | 300-Second Agitation |
|---|---|---|---|---|---|---|---|---|
| 55 | 1 | 1 | 7.2 | 5.4 | AA | AA | AA | AA |
| 56 | 2 | 2 | 6.9 | 5.4 | AA | AA | AA | AA |
| Comparative Example 3 | — | 3 | 6.9 | 5.3 | C | B | C | B |

Example 57

| | |
|---|---|
| Styrene-butyl acrylate copolymer resin (glass transition temperature 70° C.) | 100 parts by mass |
| Magenta pigment (C.I. pigment Red 114) | 5 parts by mass |
| Exemplified compound (1) | 2 parts by mass |

The above composition was mixed and melt-kneaded with a biaxial extruder (L/D=30). The kneaded mixture was cooled, hammer milled, jet milled, classified, followed by grinding to obtain magenta coloring particles (1). For the particle size of the magenta coloring particles (1), the weight-average particle diameter was 7.0 μm and the amount of the fine powder was 5.1% by number.

Then 1.5 parts by mass of finely powdered hydrophobic silica (BET: 250 m²/g) having been treated with hexamethyldisilazane, as a flow improver, was dry mixed with 100 parts by mass of the magenta coloring particles (1) with a Henschel mixer, to obtain magenta toner (1) of this example. And 7 parts by mass of the obtained magenta toner (1) and 93 parts by mass of resin-coated magnetic ferrite carrier (average particle size: 45 μm) were mixed with each other to prepare a two-component magenta developer (1) for magnetic brush development.

Example 58

Magenta toner (2) of the Example 58 was obtained in the same manner as in the Example 57 except that 2.0 parts by mass of the exemplified compound (2) was used instead of the exemplified compound (1). The properties of the toner were determined in the same manner as in the Example 51 and the results are shown in Table 35. And a two-component magenta developer (2) was obtained with this toner in the same manner as in the Example 57.

Comparative Example 4

Magenta toner (3) of the Comparative Example 4 was obtained in the same manner as in the Example 57 except that none of the exemplified compounds (1) and (2) were used. The properties of the toner were determined in the same manner as in the Example 51 and the results are shown in Table 35. And a two-component magenta developer (3) of the Comparative Example 4 was obtained with this toner in the same manner as in the Example 57.

<Evaluation>

The amount of electrical charge of the toners was measured of the two-component magenta developers (1), (2) and (3) obtained in the Examples 57 and 58 and in the Comparative Example 4, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 35 together.

(Charging Property)

AA: very good (−20 μC/g or less)
A: good (−19.9 to −10.0 μC/g)
B: practically permissible (−9.9 to −5.0 μC/g)
C: practically impermissible (−4.9 μC/g or more)

TABLE 35

Particle Size Distribution and Charging Property of
Magenta Toners (1) to (3)

| Example | Exemplified Compound No. | Toner No.: Red | Particle Size Distribution Weight-Average Particle Size (µm) | Amount of Fine Powder (% by number) | Charging Property Normal Temperature and Humidity (Q/M) 10-Second Agitation | 300-Second Agitation | High Temperature and Humidity (Q/M) 10-Second Agitation | 300-Second Agitation |
|---|---|---|---|---|---|---|---|---|
| 57 | 1 | 1 | 7.0 | 5.1 | AA | AA | AA | AA |
| 58 | 2 | 2 | 6.9 | 5.0 | AA | AA | AA | AA |
| Comparative Example 4 | — | 3 | 7.1 | 5.1 | C | B | C | B |

Examples 59 and 60

Black toners (4) and (5) of the Examples 59 and 60 were obtained using 2.0 parts by mass of the exemplified compounds (1) and (2), respectively, in the same manner as the Example 57 except that carbon black (DBP oil absorption 110 mL/100 g) was used instead of a magenta pigment. The properties of the toners were determined in the same manner as in the Example 51 and the results are shown in Table 36. And two-component black developers (4) and (5) were obtained in the same manner as in the Example 57.

Comparative Example 5

Black toner (6) of the Comparative Example 5 was obtained in the same manner as in the Example 57 except that no exemplified compounds were used and carbon black (DBP oil absorption 110 mL/100 g) was used instead of a magenta pigment. The properties of the toner were determined in the same manner as in the Example 51 and the results are shown in Table 36. And a two-component black developer (6) of the Comparative Example 5 was obtained with this toner in the same manner as in the Example 57.

<Evaluation>

The amount of electrical charge of the toners was measured of two-component black developers (4), (5) and (6) obtained in the Examples 59 and 60 and in the Comparative Example 5, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 36 together.

(Charging Property)
 AA: very good (−20 µC/g or less)
 A: good (−19.9 to −10.0 µC/g)
 B: practically permissible (−9.9 to −5.0 µC/g)
 C: practically impermissible (−4.9 µC/g or more)

TABLE 36

Particle Size Distribution and Charging Property of
Black Toners (4) to (6)

| Example | Exemplified Compound No. | Toner No.: Black | Particle Size Distribution Weight-Average Particle Size (µm) | Amount of Fine Powder (% by number) | Charging Property Normal Temperature and Humidity (Q/M) 10-Second Agitation | 300-Second Agitation | High Temperature and Humidity (Q/M) 10-Second Agitation | 300-Second Agitation |
|---|---|---|---|---|---|---|---|---|
| 59 | 1 | 4 | 7.2 | 5.4 | AA | AA | AA | AA |
| 60 | 2 | 5 | 7.2 | 5.5 | AA | AA | AA | AA |
| Comparative Example 5 | — | 6 | 7.0 | 5.7 | C | B | C | C |

Example 61

| Polyester resin | 100 parts by mass |
|---|---|
| Carbon black (DBP oil absorption 110 mL/100 g) | 5 parts by mass |
| Exemplified compound (1) | 2 parts by mass |

Polyester resin was synthesized as follows. 751 parts of adduct with 2 mol of bisphenol A propylene oxide, 104 parts of terephthalic acid and 167 parts of trimellitic anhydride were polycondensed in the presence of 2 parts of dibutyltin oxide as a catalyst to obtain polyester resin with a softening point of 125° C.

The above composition was mixed and melt-kneaded with a biaxial extruder (L/D=30). After cooled, the kneaded mixture was hammer milled, jet milled, classified, followed by grinding to obtain black coloring particles (7). For the particle size of the black coloring particles (7), the weight-average particle diameter was 7.8 μm and the amount of the fine powder was 4.6% by number.

Then 1.5 parts by mass of finely powdered hydrophobic silica (BET: 250 m²/g) having been treated with hexamethyldisilazane, as a flow improver, was dry mixed with 100 parts by mass of the black coloring particles (7) with a Henschel mixer. And 7 parts by mass of (the obtained black toner (7)) and 93 parts by mass of resin-coated magnetic ferrite carrier (average particle size: 45 μm) were mixed with each other to prepare a two-component black developer (7) for magnetic brush development.

Example 62

Black toner (8) of the Example 62 was obtained in the same manner as in the Example 61 except that 2.0 parts by mass of the exemplified compound (2) was used instead of the exemplified compound (1). The properties of the toner were determined in the same manner as in the Example 51 and the results are shown in Table 37. And a two-component black developer (8) was obtained with this toner in the same manner as in the Example 61.

Comparative Example 6

Black toner (9) of the Comparative Example 6 was obtained in the same manner as in the Example 61 except that none of the exemplified compounds (1) and (2) were used. The properties of the toner were determined in the same manner as in the Example 51 and the results are shown in Table 37. And a two-component black developer (9) of the Comparative Example 6 was obtained with this toner in the same manner as in the Example 61.

<Evaluation>

The amount of electrical charge of the toners was measured of the two-component black developers (7), (8) and (9) obtained in the Examples 61 and 62 and in the Comparative Example 6, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 37 together.

(Charging Property)
  AA: very good (−20 μC/g or less.)
  A: good (−19.9 to −10.0 μC/g)
  B: practically permissible (−9.9 to −5.0 μC/g)
  C: practically impermissible (−4.9 μC/g or more)

TABLE 37

Particle Size Distribution and Charging Property of Black Toners (7) to (9)

| | | | Particle Size Distribution | | Charging Property | | | |
|---|---|---|---|---|---|---|---|---|
| | | | | | Normal Temperature and Humidity (Q/M) | | High Temperature and Humidity (Q/M) | |
| Example | Exemplified Compound No. | Toner No.: Black | Weight-Average Particle Size (μm) | Amount of Fine Powder (% by number) | 10-Second Agitation | 300-Second Agitation | 10-Second Agitation | 300-Second Agitation |
| 61 | 1 | 7 | 7.8 | 4.6 | AA | AA | AA | AA |
| 62 | 2 | 8 | 7.9 | 5.0 | AA | AA | AA | AA |
| Comparative Example 6 | — | 9 | 7.5 | 4.9 | C | B | C | B |

Examples 63 to 74 and Comparative Examples 7 to 12

Figure 20:
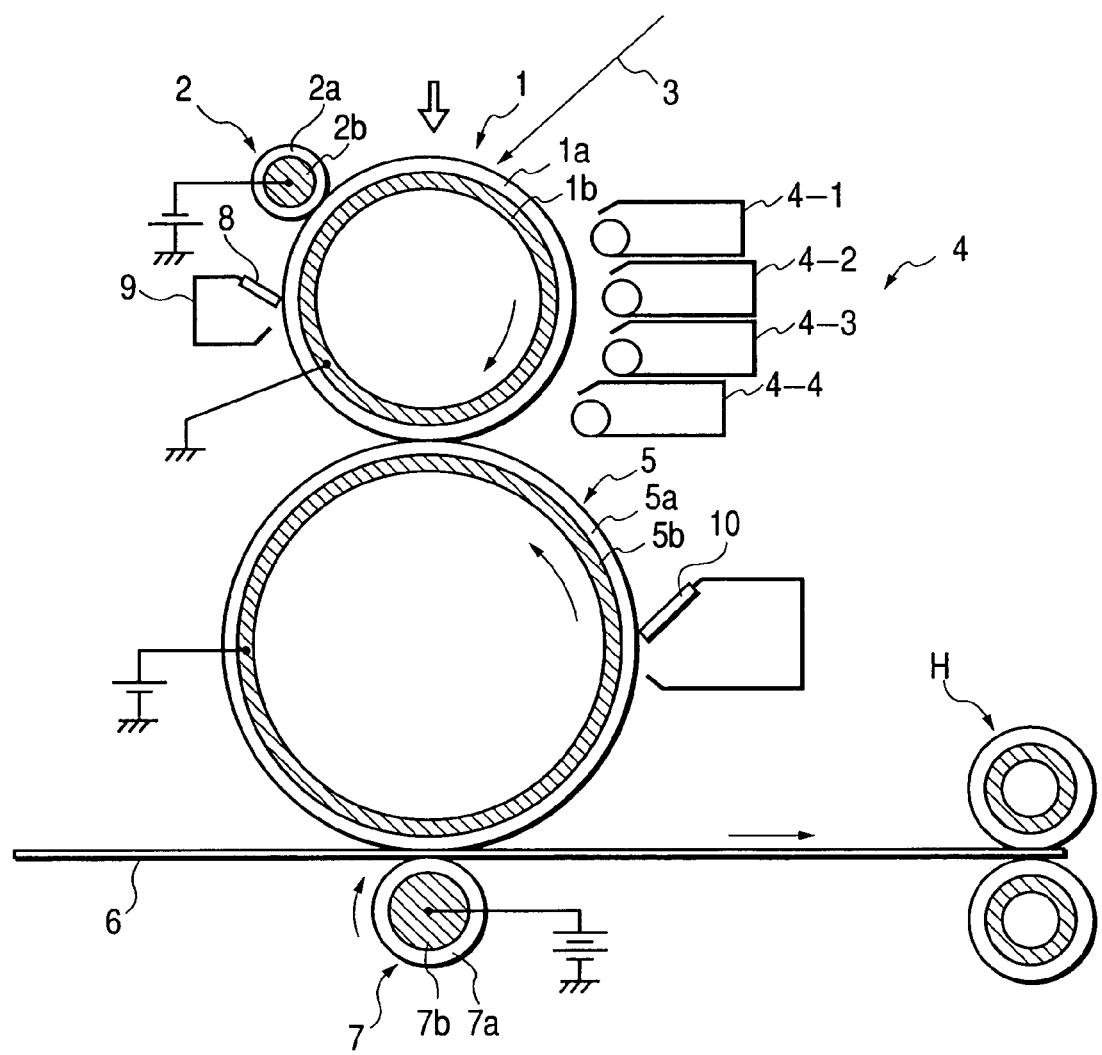
FIG. 20 is a schematic illustration of an image forming apparatus used in Examples 63 to 74 of the present invention and Comparative Examples 7 to 12.

First, an image forming apparatus having been used in the method of image formation in the Examples 63 to 74 and in the Comparative Examples 7 to 12 will be described. FIG. 20 is a schematic view illustrating a cross section of an image forming apparatus for carrying out the image forming method of the Examples and Comparative Examples of this invention. The photosensitive drum 1 shown in FIG. 20 has a photosensitive layer 1a, which includes organic optical semiconductor, on a base material 1b and is structured in such a manner as to rotate in the direction shown by the arrow. The surface of the photosensitive drum 1 is charged at about −600V surface electric potential by a charging roller 2 as a charging member which rotates in contact with the above drum 1. As shown in FIG. 20, the charging roller 2 consists of a conductive elastic layer 2a and a core bar 2b which is coated with the above conductive elastic layer.

Figure 21:
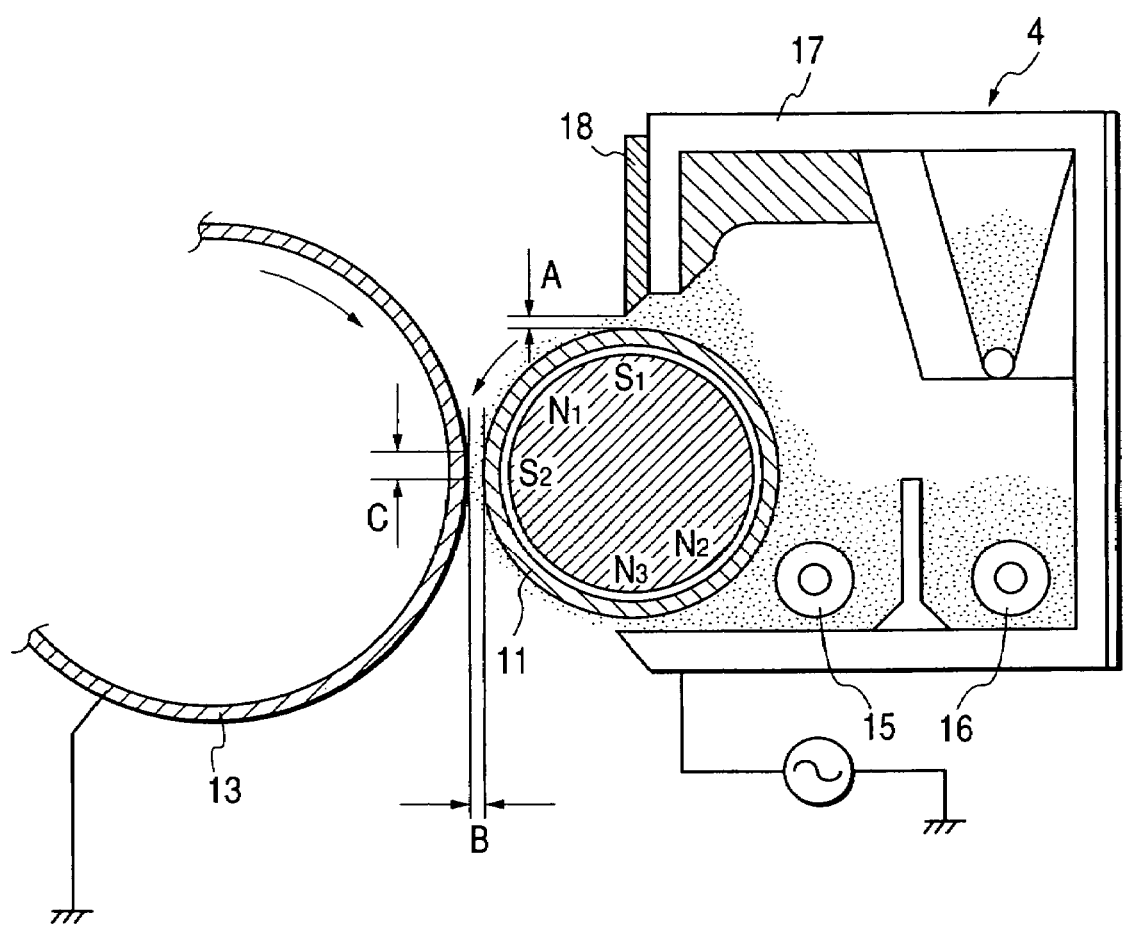
FIG. 21 is an enlarged transverse cross-sectional view of the main part of a developing assembly for a two-component developer used in Examples 63 to 74 of the present invention and Comparative Examples 7 to 12.

The photosensitive drum 1 with its surface electrically charged is exposed to light 3, and at the time of the exposure an image of electrostatic charges with −100V electrical potential at the exposed portion and −600V electrical potential at the dark portion is on the drums formed by turning on and off the light with a polygon mirror according to the digital image information. Then the image of electrostatic charges on the photosensitive drum 1 is reversely developed with a plurality of developing equipment 4-1,4-2, 4-3 and 4-4 to become tangible; thus, a toner image is formed on the photosensitive drum 1. In this developing, two-component developers obtained in the Examples 51 to 62 and in the Comparative Examples 1 to 6 were used and the toner image was formed with yellow, magenta, cyan or black toner. FIG. 21 is an enlarged sectional view illustrating the main part of each developing equipment 4 used with the two-component developers.

Then the toner image on the photosensitive drum 1 is transferred to an intermediate transfer body 5, which rotates in contact with the photosensitive drum 1. As a result, a developed image made up of four colors of toner overlaid is formed on the intermediate transfer body 5. The residual toner, which has not been transferred to the intermediate transfer body 5 and left on the photosensitive drum 1, is collected into a container 9 for residual toner with a cleaning member 8.

The intermediate transfer body 5 consists of a core bar 5b, as a base material, and an elastic layer 5a laminated on the core bar, as shown in FIG. 20. In this example, an intermediate transfer body 5 was used which consisted of an elastic layer 5a of nitrile-butadiene rubber in which carbon black, as a conductivity-imparting material, was fully dispersed and a pipe-like core bar 5b coated with the elastic layer 5a. The hardness of the elastic layer 5a measured in accordance with "JIS K-6301" was 30 degree and the volume resistivity of the same was $10^9$ Ω·cm. Transfer current needed for transferring the toner image from the photosensitive drum 1 to the intermediate transfer body 5 was about 5 μA and the current was obtained by applying +500V from a voltage source to the core bar 5b.

The developed image made up of four colors of toner overlaid having been formed on the intermediate transfer body 5 is transferred to a transfer medium such as paper by a transfer roller 7 and fixed thereon with a heat fixing equipment H. The transfer roller 7 consists of an elastic layer 7a of a cellular material of ethylene-propylene-diene terpolymer (EPDM) in which carbon black, as a conductivity-imparting material, has fully dispersed and a core bar 7b of 10 mm in outer diameter coated with the elastic layer 7a. The volume resistivity of the used elastic layer 7a was $10^6$ Ω·cm and the hardness of it measured in accordance with "JIS K-6301" was 35. A transfer current of 15 μA was allowed to flow through the transfer roller 7 by applying a voltage thereto.

Figure 24:
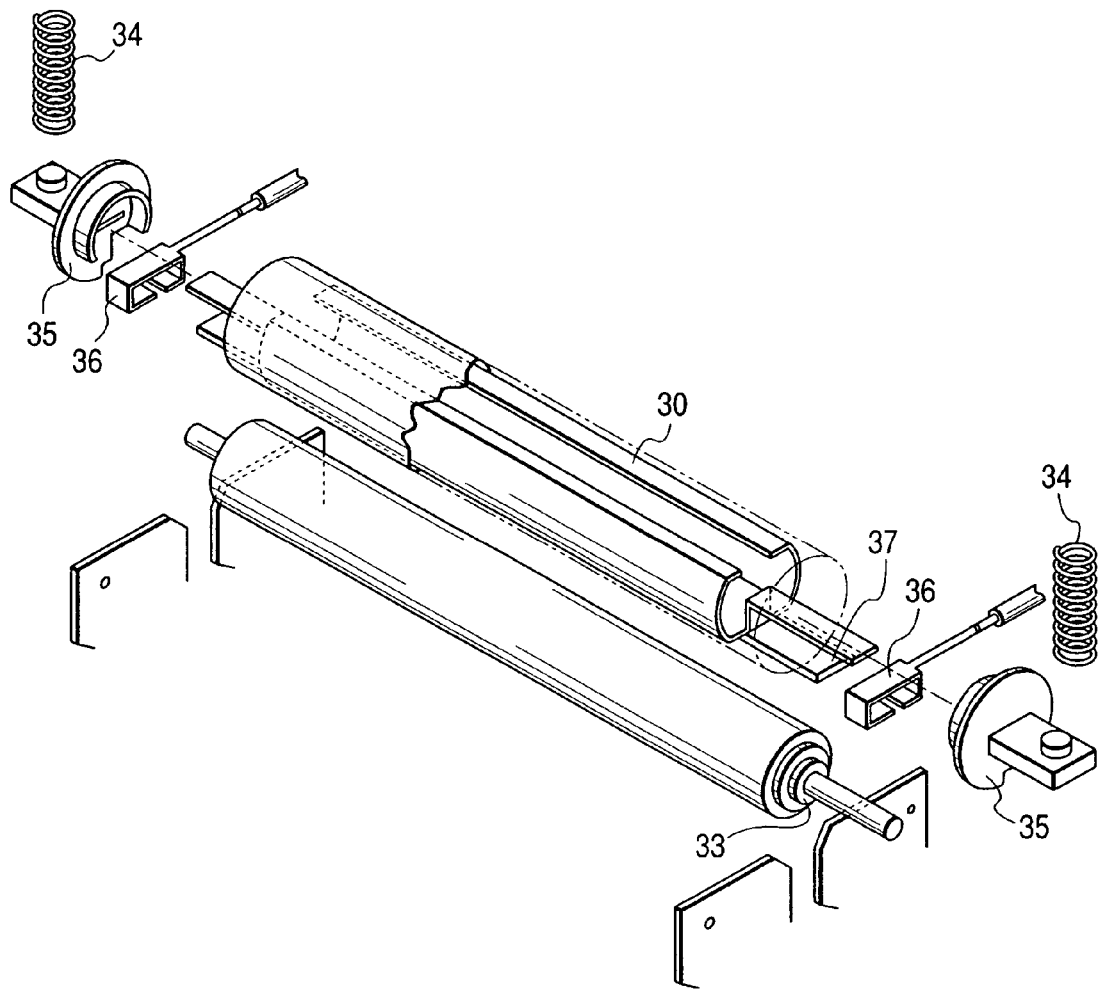
FIG. 24 is an exploded perspective view of the main part of a fixing assembly used in Examples of the present invention.
Figure 25:
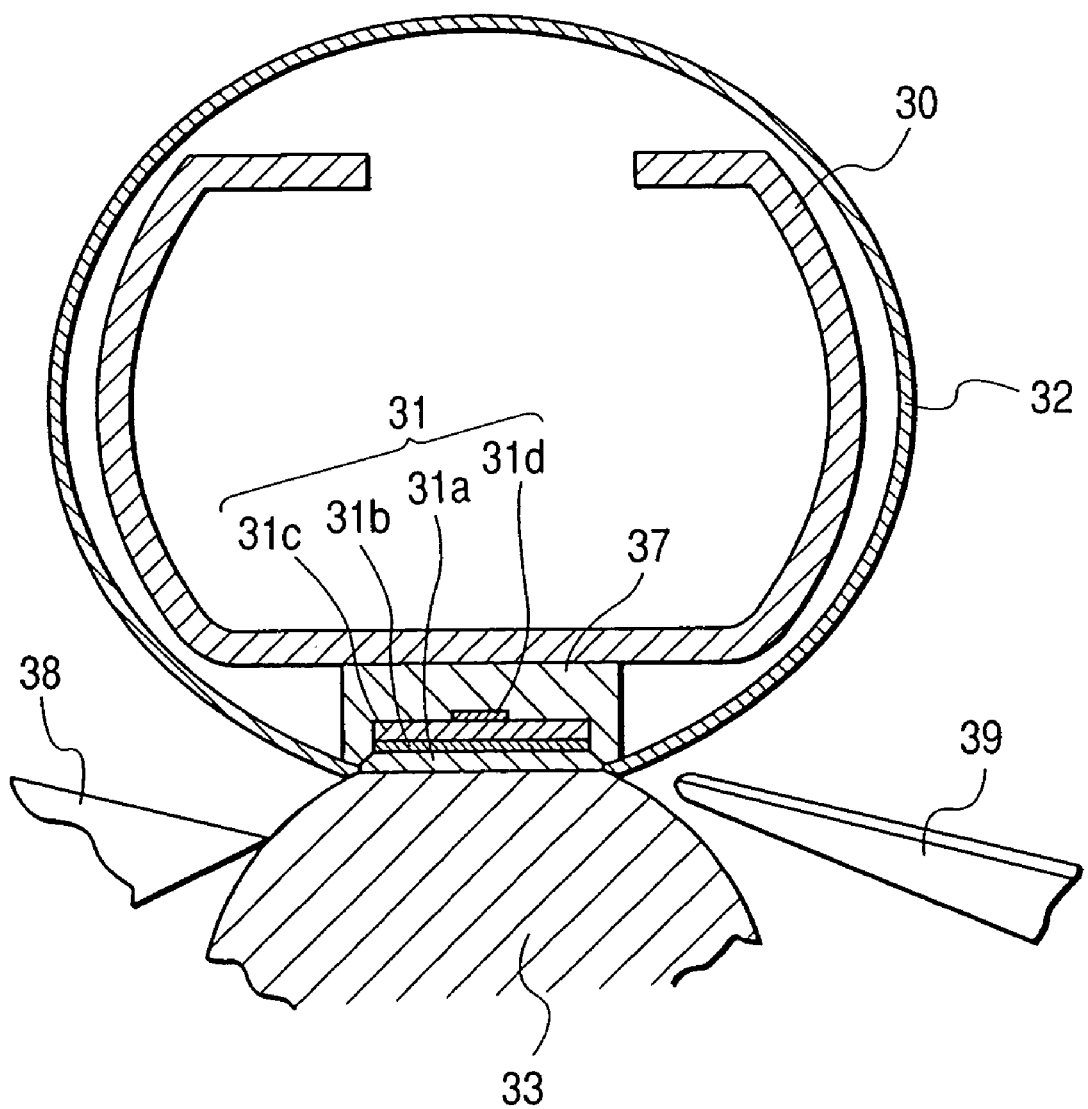
FIG. 25 is an enlarged transverse cross-sectional view of the main part showing how a film stands when a fixing assembly used in Examples of the present invention is not driven.

In the apparatus shown in FIG. 20, a heat roll type of fixing equipment without an oil coating mechanism, as shown in FIGS. 24 and 25, was used as a heat fixing equipment H. And the apparatus used was such that both its upper roller and lower roller were provided with a surface layer of fluorocarbon resin. The diameter of each roller was 60 nm. The temperature at the time of fixing was 160° C. and the nip between the rolls was set at 7 mm. The residual toner, which had not been transferred to the intermediate transfer body 5 and left on the photosensitive drum 1, collected by cleaning was conveyed to the developing equipment by a reuse mechanism to be reused.

<Evaluation>

Printout tests were conducted on the above image forming apparatus at a print speed of 8 sheets of paper (A4 size) per minute in monochrome in an intermittent mode (that is, a mode in which developing equipment is stopped over 10 seconds every time printing is done on a sheet of paper, so as to accelerate the degradation of toner by the spare operation at the time of restart) under the environmental conditions of normal temperature and humidity (25° C., 60% RH) and of high temperature and humidity (30° C., 80% RH), while supplying sequentially two-component developers prepared using the toner of the Examples 51 to 62 and of the Comparative Examples 1 to 6, and the obtained printout images were evaluated on the following items. The evaluation results are shown in Table 38 together.

(Evaluation of Printout Image)

1. Image Density

Printing was done on a prescribed number of sheets of paper, ordinary plain paper for copying (75 g/m$^2$), and evaluation was made in terms of the degree to which the density of the printout image at the very beginning of printing was maintained by the printout image at the very end of printing. The image density was measured with a Macbeth reflection densitometer (manufactured by Macbeth) and the relative density of printout image on a white background with a copy density of 0.00 was measured and used for the evaluation.

AA: Excellent (image density at the very end of printing was 1.40 or more)

A: Good (image density at the very end of printing was 1.35 or more and less than 1.40)

B: Fair (image density at the very end of printing was 1.00 or more and less than 1.35)

C: Bad (image density at the very end of printing was less than 1.00)

2. Image Fog

Printing was done on a prescribed number of sheets of paper, ordinary plain paper for copying (75 g/m$^2$), and evaluation was made in terms of the white solid image at the very end of printing. Specifically, the evaluation was made in the following manner. First the fog density was obtained from the following formula: (Ds-Dr), where Ds is the worst value of the reflection density on the white background portion after printing measured with a reflection densitometer (REFLECTOMETER ODEL TC-6DS by TOKYO DENSHOKU CO., LTD) and Dr is the mean value of the reflection density of the paper before printing. Then evaluation was made based on the following criteria.

AA: Very good (fog density was 0% or more and less than 1.5%)

A: Good (fog density was 1.5% or more and less than 3.0%)

B: Practically permissible (fog density was 3.0% or more and less than 5.0%)

C: Practically impermissible (fog density was 5.0% or more)

3. Transfer Properties

A black solid image was printed out on a prescribed number of sheets of paper, ordinary plain paper for copying (75 g/m$^2$), and the image missing at the very end of printing was visually observed. Evaluation was made based on the following criteria.

Figure 22:
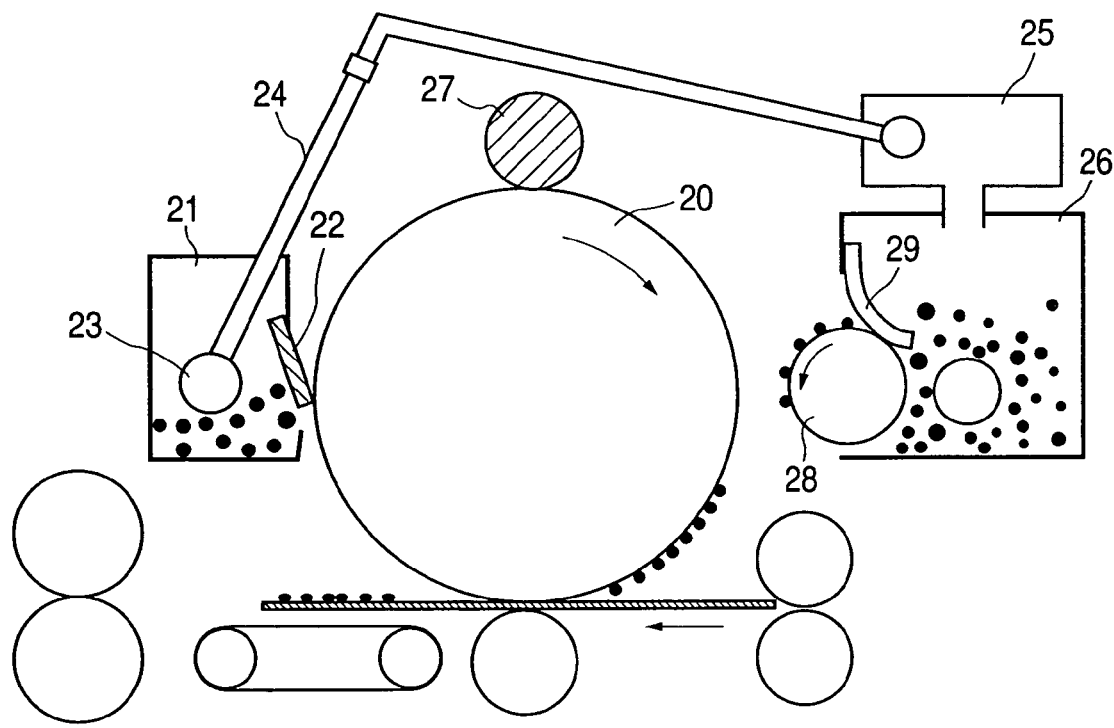
FIG. 22 is a schematic illustration of an image, forming apparatus which reuses untransferred toner used in Examples 75 to 80 of the present invention and Comparative Examples 13 to 15.

AA: Very good (almost no image missing occurred)
A: Good (slight image missing was observed)
B: Practically permissible
C: Practically impermissible In Examples 63 to 74 and in Comparative Examples 7 to 12, an image was printed out on 5000 sheets of paper, and visual evaluation was made on scratches and retention of the toner occurring on the photosensitive drum and on the surface of the intermediate transfer body as well as the effect on the printout image (match between the toners and the image forming apparatus). The results were as follows. In the system of the Examples 63 to 74 using the two-component developers, neither scratches nor retention of the residual toner was observed on the surface of the photosensitive drum and of the intermediate transfer body and the match between the toners and the image forming apparatus was very good. On the other hand, in the system of the Comparative Examples 7 to 12 using the two-component developers, retention of the toner was observed on the surface of the photosensitive drum. Furthermore, in the system of the Comparative Examples 7 to 12 using the two-component developers, retention of the toner and scratches were observed on the surface of the intermediate transfer body and defects in the form of vertical lines was also observed in the image. Thus problems arouse in the match between the toners and the image forming apparatus.

image forming apparatus obtained by remolding a commercially available laser beam printer, LBP-EX (manufactured by Canon), in such a manner as to be mounted with a reuse mechanism and by resetting the same, as shown in FIG. 22. Specifically, the image forming apparatus shown in FIG. 22 was mounted with a system for reusing toner in which the toner having not been transferred and remaining on the photosensitive drum 20 was scraped off with the elastic blade 22 of the cleaner 21 in contact with the photosensitive drum 20, conveyed to the inside of the cleaner 21 with a cleaner roller, passed through the cleaner reuse 23, and returned to the developing equipment 26 via the hopper 25 with a supplying pipe 24 provided with a conveying screw.

In the image forming apparatus shown in FIG. 22, the surface of the photosensitive drum 20 was charged with a primary charging roller 27. As the primary charging roller 27 a nylon-resin coated rubber roller (12 mm in diameter, contact pressure 50 g/cm) in which conductive carbon was dispersed was used, and the electrostatic latent image carrier (photosensitive drum 20) was exposed to laser beam (600 dpi, not shown in the Figure) to form an electrostatic latent image with a dark portion potential VD of −700V and a light portion potential VL of −200V. As a toner carrier, a developing sleeve

TABLE 38

| | | Evaluation of Printout Image | | | | | |
| | | Normal Temperature and Humidity | | | High Temperature and Humidity | | |
| Example | Two-component Developer | Image Density | Image Fog | Transfer Properties | Image Density | Image Fog | Transfer Properties |
|---|---|---|---|---|---|---|---|
| 63 | blue 1 | AA | AA | AA | AA | AA | AA |
| 64 | blue 2 | AA | AA | AA | AA | AA | AA |
| 65 | yellow 1 | AA | AA | AA | AA | AA | AA |
| 66 | yellow 2 | AA | AA | AA | AA | AA | AA |
| 67 | black 1 | AA | AA | AA | AA | AA | AA |
| 68 | black 2 | AA | AA | AA | AA | AA | AA |
| 69 | red 1 | AA | AA | AA | AA | AA | AA |
| 70 | red 2 | AA | AA | AA | AA | AA | AA |
| 71 | black 4 | AA | AA | AA | AA | AA | AA |
| 72 | black 5 | AA | AA | AA | AA | AA | AA |
| 73 | black 7 | AA | AA | AA | AA | AA | AA |
| 74 | black 8 | AA | AA | AA | AA | AA | AA |
| Comparative Example 7 | blue 3 | C | C | C | C | C | C |
| 8 | yellow 3 | C | C | C | C | C | C |
| 9 | black 3 | B | B | C | B | C | C |
| 10 | red 3 | B | B | C | B | C | C |
| 11 | black 6 | B | B | C | C | C | C |
| 12 | black 9 | B | B | C | B | C | C |

Examples 75 to 80, Comparative Examples 13 to 15

When carrying out the image forming methods of the Examples 75 to 80 and the Comparative Examples 13 to 15, the toners obtained in the Examples 51 to 56 and in the Comparative Examples 1 to 3 were used as developers, respectively. And as means of forming an image, used was an 28 coated with resin, in which carbon black was dispersed, and having a surface roughness Ra of 1.1 was used.

Figure 23:
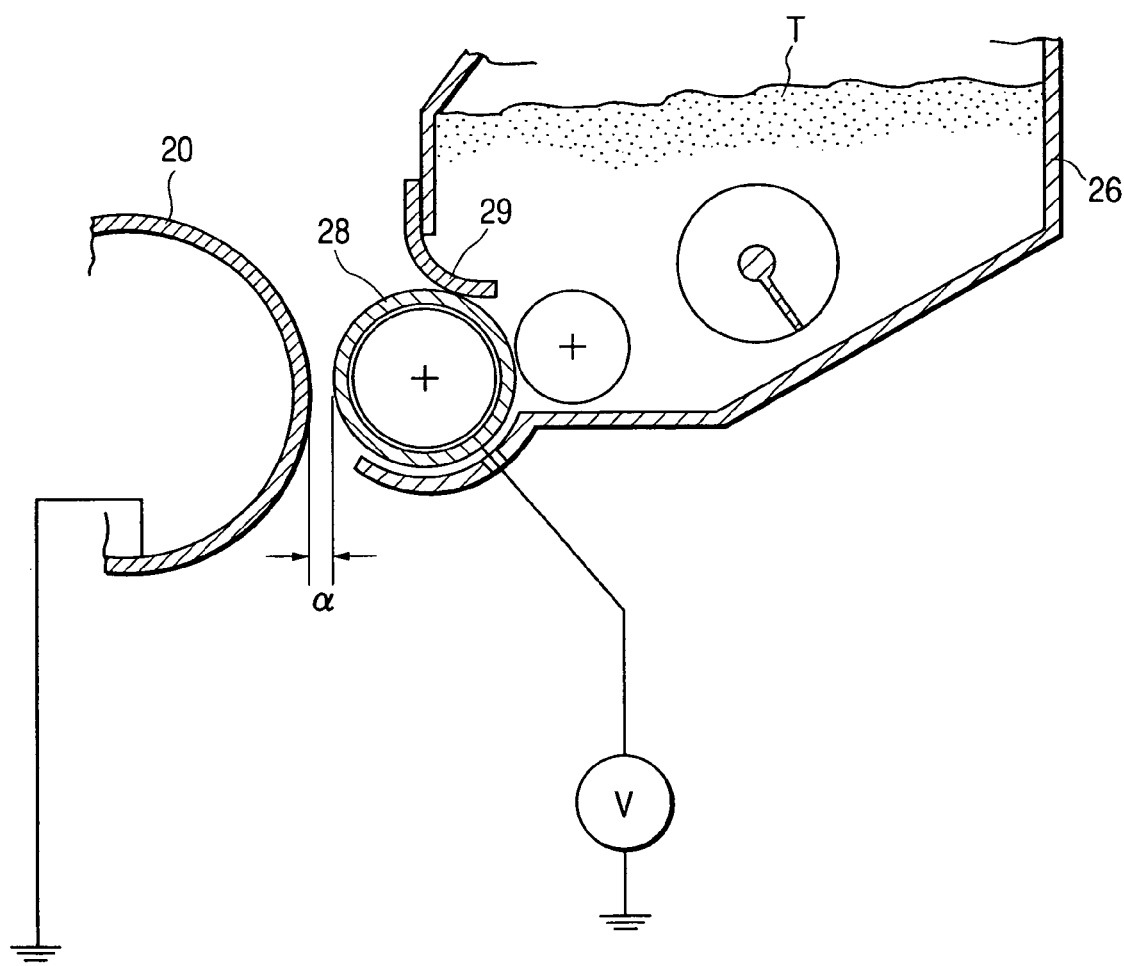
FIG. 23 is an enlarged transverse cross-sectional view of the main part of a developing assembly for a one-component developer used in Examples 75 to 80 of the present invention and Comparative Examples 13 to 15.

FIG. 23 is an enlarged sectional view of the main part of the developing equipment for single-component developer used in the Examples 75 to 80 and in the Comparative Examples 13 to 15. The conditions under which an electrostatic latent image was developed were such that the moving speed of the developing sleeve 28 was set at 1.1 times as fast as that of the surface of the photosensitive drum 20 facing the developing sleeve and the space α between the photosensitive drum 20 and the developing sleeve 28 (space S-D) was set at 270 μm. As a member for regulating the thickness of the toner layer, a urethane rubber blade 29 was used in such a manner as to be in contact with the developing sleeve 28. The temperature of a heat fixing equipment for fixing the toner image was set at 160° C. As a heat fixing equipment, the fixing equipment shown in FIGS. 24 and 25 was used.

Printing was done on 30,000 sheets of paper on the above image forming apparatus at a print speed of 8 sheets of paper (A4 size) per minute in a continuous mode (that is, a mode in which the consumption of toner was accelerated without stopping developing equipment) under the environmental conditions of normal temperature and humidity (25° C., 60% RH), while sequentially supplying toner. The density of the obtained printout image was measured and the durability was evaluated based on the criteria described below. Further, the image of the 10,000th printout was observed and the image fog was evaluated based on the criteria described below. The state of equipment constituting the image forming apparatus was also observed after the durability test and the match between the apparatus and each toner was evaluated. The results are shown in Table 39 together.

(Change in Image Density within the Durability Limit)

Printing was done on a prescribed number of sheets of paper, ordinary plain paper for copying (75 g/m$^2$), and evaluation was made in terms of the degree to which the density of the printout image at the very beginning of printing was maintained by the printout image at the very end of printing. The image density was measured with a Macbeth reflection densitometer (manufactured by Macbeth) and the relative density of printout image on a white background with a copy density of 0.00 was measured and used for the evaluation.

AA: Excellent (image density at the very end of printing was 1.40 or more)

A: Good (image density at the very end of printing was 1.35 or more and less than 1.40)

B: Fair (image density at the very end of printing was 1.00 or more and less than 1.35)

C: Bad (image density at the very end of printing was less than 1.00)

(Image Fog)

Printing was done on a prescribed number of sheets of paper, ordinary plain paper for copying (75 g/m$^2$), and evaluation was made in terms of the white solid image at the very end of printing. Specifically, the evaluation was made in the following manner. First the fog density was obtained from the following formula: (Ds-Dr), where Ds is the worst value of the reflection density on the white background portion after printing measured with a reflection densitometer (REFLECTOMETER ODEL TC-6DS by TOKYO DENSHOKU CO., LTD) and Dr is the mean value of the reflection density of the paper before printing. Then evaluation was made based on the following criteria.

AA: Very good (fog density was 0% or more and less than 1.5%)

A: Good (fog density was 1.5% or more and less than 3.0%)

B: Practically permissible (fog density was 3.0% or more and less than 5.0%)

C: Practically impermissible (fog density was 5.0% or more)

(Evaluation of Match Between Toner and Image Forming Apparatus)

1. Match Between Toner and Developing Sleeve

After completing the printout tests, the retention of the residual toner on the surface of the developing sleeve and its effects on the printout image were visually observed and evaluated.

AA: Very good (no retention occurred)

A: Good (almost no retention occurred)

B: Practically permissible (retention occurred but did not affect the image)

C: Practically impermissible (a large amount of retention-occurred and unevenness of image occurred)

2. Match Between Toner and Photosensitive Drum

Scratches and retention of the toner occurring on the surface of the photosensitive drum as well as their effects on the printout image were visually observed and evaluated.

AA: Very good (no scratches and retention occurred)

A: Good (scratches and retention slightly occurred, but did not affect the printout image)

B: Practically permissible (scratches and retention occurred, but the effects on the printout image were small)

C: Practically impermissible (much retention occurred and defects occurred in the printout image in the form of vertical lines)

3. Match Between Toner and Fixing Equipment

The state of the fixing film surface was observed, and the durability was evaluated through totaling and averaging the results of the surface quality and the retention of the residual toner.

(1) Surface Quality

After completing the printout tests, scratches and scrapes occurring on the surface of the fixing film were visually observed and evaluated.

AA: Very good (no scratches and scrapes occurred)

A: Good (almost no scratches and scrapes occurred)

B: Practically permissible

C: Practically impermissible (2) Retention of Residual Toner

After completing the printout tests, the retention of the residual toner on the surface of the film was visually observed and evaluated.

AA: Very good (no retention occurred)

A: Good (almost no retention occurred)

B: Practically permissible

C: Practically impermissible

TABLE 39

Evaluation of Printout Image and Match between Toner and Image Forming Apparatus

| | | Evaluation of Printout Image | | | | | Evaluation of Match between Toner and Equipment | | | |
|---|---|---|---|---|---|---|---|---|---|---|
| | | Change in Image Density within the Durability Limit | | | | Image | | | Photo | Fixing Equipment |
| | | Initial | 1000th | | | Fog | | | | |
| Example | Toner | Print out | Print out | 10,000th Printout | 30,000th Printout | 10,000th Printout | Developing Sleeve | sensitive Drum | Surface Quality | Retention of Toner |
| 75 | blue 1 | AA | AA | AA | AA | AA | AA | AA | AA | AA |
| 76 | blue 2 | AA | AA | AA | AA | AA | AA | AA | AA | AA |
| 77 | yellow 1 | AA | AA | AA | AA | AA | AA | AA | AA | AA |
| 78 | yellow 2 | AA | AA | AA | AA | AA | AA | AA | AA | AA |
| 79 | black 1 | AA | AA | AA | AA | AA | AA | AA | AA | AA |
| 80 | black 2 | AA | AA | AA | AA | AA | AA | AA | AA | AA |
| Comparative Example 13 | blue 3 | B | C | C | C | C | C | C | C | C |
| 14 | yellow 3 | B | C | C | C | C | C | C | C | C |
| 15 | black 3 | A | B | C | C | C | C | C | C | C |

Example 81

Printout tests were conducted in the same manner as in the Example 75, except that the toner reuse mechanism was dismounted from the image forming apparatus of FIG. 22 and the print speed was set at 16 sheets of paper (A4 size) per minute, in a continuous mode (that is, a mode in which the consumption of toner is accelerated without stopping develop equipment) while supplying sequentially the blue toner (1) of the Example 51. The obtained images and the match between the toner and the used image forming apparatus were evaluated on the same items as those of the Examples 75 to 80 and of the Comparative Examples 13 to 15. The results were good for any of the items.

Example 82

Evaluation was made in the same manner as in the Example 81, except that the type of toner used was changed from the blue toner (1) of the Example 51 to the blue toner (2) of the Example 52. The results were good for any of the items.

What is claimed is:

1. A polyhydroxyalkanoate polymer having a repeating unit represented by Chemical Formula (1)

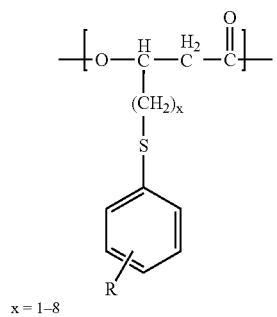

(1)

wherein R is arbitrarily selected from a hydrogen atom, a halogen atom, CN, $NO_2$, COOR', $SO_2R''$, $CH_3$, $C_2H_5$, $C_3H_7$, $C(CH_3)_2H$ and $C(CH_3)_3$; where R' is H, Na, K, $CH_3$ or $C_2H_5$, and R" is OH, ONa, OK, a halogen atom, $OCH_3$ or $OC_2H_5$; and x is an integer arbitrarily selected from 1 to 8; with the proviso that a polyhydroxyalkanoate is excluded which has a hydrogen atom as R and x in all the units is 2 or 4.

2. The polyhydroxyalkanoate polymer according to claim 1, which has a number average molecular weight in the range of from 1,000 to 500,000.

3. The polyhydroxyalkanoate polymer according to claim 1, which contains a repeating 3-hydroxy-5-phenylsulfanyl valeric acid unit represented by Chemical Formula (4)

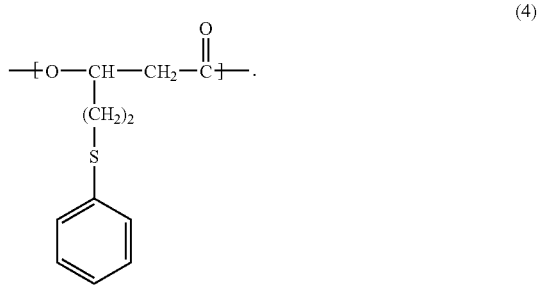

(4)

4. The polyhydroxyalkanoate polymer according to claim 1, which contains a repeating 3-hydroxy-4-phenylsulfanyl butyric acid unit represented by Chemical Formula (5)

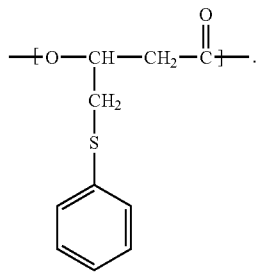

(5)

5. The polyhydroxyalkanoate polymer according to claim 1, which contains a repeating 3-hydroxy-5-[(4-methylphenyl)sulfanyl]valeric acid unit represented by Chemical Formula (6)

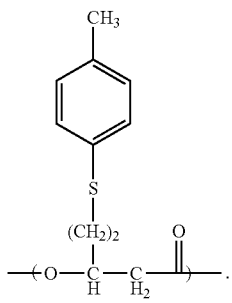

(6)

6. The polyhydroxyalkanoate polymer according to claim 1, which contains a repeating 3-hydroxy-5-[(4-fluorophenyl)sulfanyl]valeric acid unit represented by Chemical Formula (7)

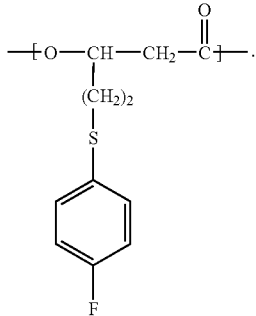

(7)

7. The polyhydroxyalkanoate polymer according to claim 1, which contains a repeating 3-hydroxy-4-[(4-fluorophenyl)sulfanyl]butyric acid unit represented by Chemical Formula (8)

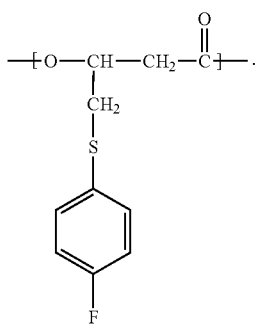

(8)

8. The polyhydroxyalkanoate polymer according to claim 1, which contains a repeating 3-hydroxy-5-[(4-sulfophenyl)sulfanyl]valeric acid unit represented by Chemical Formula (9)

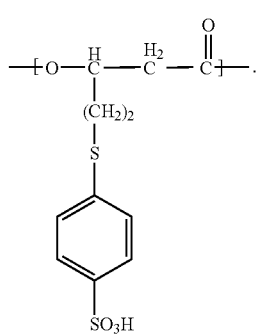

(9)

9. The polyhydroxyalkanoate polymer according to claim 1, which contains a repeating 3-hydroxy-8-[(4-carboxyphenyl)sulfanyl]octanoic acid unit represented by Chemical Formula (10)

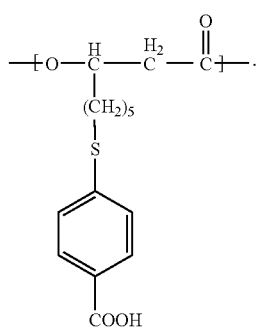

(10)

10. The polyhydroxyalkanoate polymer according to claim 1, which contains a repeating 3-hydroxy-6-[(4-carboxyphenyl)sulfanyl]hexanoic acid unit represented by Chemical Formula (11)

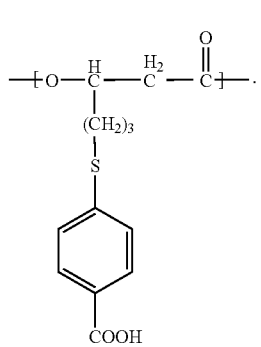

(11)

* * * * *

UNITED STATES PATENT AND TRADEMARK OFFICE
CERTIFICATE OF CORRECTION

PATENT NO. : 7,408,017 B2
APPLICATION NO. : 11/155599
DATED : August 5, 2008
INVENTOR(S) : Takeshi Imamura et al.

It is certified that error appears in the above-identified patent and that said Letters Patent is hereby corrected as shown below:

ON TITLE PAGE ITEM [56] REFERENCES CITED

Other Publications, (after Ritter, et al.) "-nananoate   ) from" should read -- -nananoate) from--.

COLUMN 1

Line 30, "therefore" should read --therefore.--; and
    Line 45, "acid." should read --acid-- and close up right margin.

COLUMN 6

Line 20, "Patent." should read --Patent--; and
    Line 48, "having-such" should read --having such--.

COLUMN 7

Line 56, "1 to 8," should read --1 to 8;--.

COLUMN 8

Line 19, "Formula (1)" should read --Formula (1);--.

COLUMN 11

Line 33, "$SO_2R'$," should read --$SO_2R''$,--.

COLUMN 13

Line 67, "Chemical." should read --Chemical--.

COLUMN 15

Line 37, "image," should read --image--.

COLUMN 17

Line 53, "types," should read --types.--.

UNITED STATES PATENT AND TRADEMARK OFFICE
CERTIFICATE OF CORRECTION

| | |
|---|---|
| PATENT NO. | : 7,408,017 B2 |
| APPLICATION NO. | : 11/155599 |
| DATED | : August 5, 2008 |
| INVENTOR(S) | : Takeshi Imamura et al. |

It is certified that error appears in the above-identified patent and that said Letters Patent is hereby corrected as shown below:

<u>COLUMN 24</u>

Line 19, "$CH_3$." should read --$CH_3$,--.

<u>COLUMN 26</u>

Line 56, "Incorporating" should read --incorporating--.

<u>COLUMN 31</u>

Line 67, "Pigment-Blue" should read --Pigment Blue--.

<u>COLUMN 33</u>

Line 15, "dylene;" should read --dylene,--;
Line 38, "electrostatic-latent" should read --electrostatic latent--; and
Line 53, "-400" should read --400--.

<u>COLUMN 35</u>

Line 2, "9 μm" should read --9 μm.--.

<u>COLUMN 36</u>

Line 48, "stability" should read --stability.--.

<u>COLUMN 39</u>

Line 25, "anhydrous-magnesium" should read --anhydrous magnesium--.

<u>COLUMN 40</u>

Line 23, "methanol-containing" should read --methanol containing--.

<u>COLUMN 43</u>

Line 26, "7'," should read --7,--.

UNITED STATES PATENT AND TRADEMARK OFFICE
CERTIFICATE OF CORRECTION

PATENT NO. : 7,408,017 B2
APPLICATION NO. : 11/155599
DATED : August 5, 2008
INVENTOR(S) : Takeshi Imamura et al.

It is certified that error appears in the above-identified patent and that said Letters Patent is hereby corrected as shown below:

COLUMN 48

Lines 50-62, " 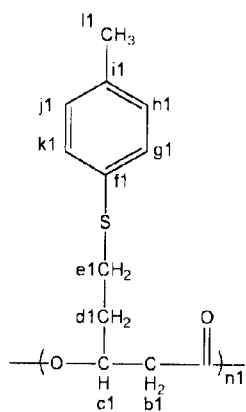 " should read -- 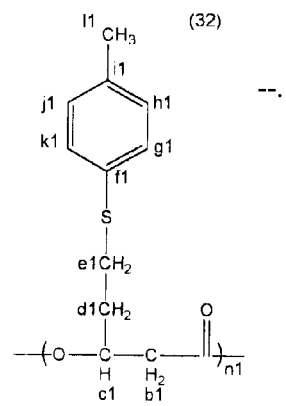 --.

COLUMN 56

Line 7, "added-thereto" should read --added thereto--; and
Line 35, "hydrochloric-acid" should read --hydrochloric acid--.

COLUMN 59

Line 38, "Stirred" should read --stirred--.

COLUMN 60

Line 57, "12" should read --72--.

COLUMN 63

Line 47, "$^{13}C$" should read --$^{13}C.$--.

COLUMN 64

Line 54, "200 mL" should read --200 m-L--.

COLUMN 65

Line 61, "76 mg" should read --70 mg--.

UNITED STATES PATENT AND TRADEMARK OFFICE
CERTIFICATE OF CORRECTION

| | | |
|---|---|---|
| PATENT NO. | : 7,408,017 B2 | |
| APPLICATION NO. | : 11/155599 | |
| DATED | : August 5, 2008 | |
| INVENTOR(S) | : Takeshi Imamura et al. | |

It is certified that error appears in the above-identified patent and that said Letters Patent is hereby corrected as shown below:

COLUMN 66

Line 41, "-60°C." should read --60°C.--.

COLUMN 67

Line 57, "1.25" should read --125--.

COLUMN 71

Line 8, "Tokyo. Kasei" should read --Tokyo Kasei--; and
Line 9, "2-L-vol" should read --2-L-vol.--.

COLUMN 72

Line 1, "Spec-" should read --spec- --; and
Line 23, "sulfonyl)" should read --sulfonyl]--.

COLUMN 73

Line 25, "mold %." should read --mol %.--.

COLUMN 75

Line 22, "polymerizable-monomer" should read --polymerizable monomer--.

COLUMN 78

Line 18, "(DBP-oil" should read --(DBP oil--; and "1.00 g)" should read --100 g)--.

UNITED STATES PATENT AND TRADEMARK OFFICE
CERTIFICATE OF CORRECTION

PATENT NO. : 7,408,017 B2
APPLICATION NO. : 11/155599
DATED : August 5, 2008
INVENTOR(S) : Takeshi Imamura et al.

It is certified that error appears in the above-identified patent and that said Letters Patent is hereby corrected as shown below:

<u>COLUMN 84</u>

Line 26, "less.)" should read --less)--.

Signed and Sealed this

Twenty-fourth Day of February, 2009

JOHN DOLL
*Acting Director of the United States Patent and Trademark Office*